US011344596B2

(12) United States Patent
Doering et al.

(10) Patent No.: US 11,344,596 B2
(45) Date of Patent: May 31, 2022

(54) METHODS FOR MAKING BOTANICAL EXTRACT COMPOSITION

(71) Applicant: CARGILL, INCORPORATED, Wayzata, MN (US)

(72) Inventors: Skye Doering, Minneapolis, MN (US); Dan S. Gaspard, Victoria, MN (US); Kristopher T. Mortenson, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 17/224,847

(22) Filed: Apr. 7, 2021

(65) Prior Publication Data

US 2021/0290717 A1    Sep. 23, 2021

Related U.S. Application Data

(63) Continuation of application No. PCT/US2020/026885, filed on Apr. 6, 2020.

(60) Provisional application No. 62/832,273, filed on Apr. 10, 2019, provisional application No. 62/830,448, filed on Apr. 6, 2019.

(51) Int. Cl.
| *A61K 36/28* | (2006.01) |
| *A23L 33/105* | (2016.01) |
| *A23L 2/52* | (2006.01) |
| *A61K 31/216* | (2006.01) |
| *A61K 36/185* | (2006.01) |
| *B01D 15/12* | (2006.01) |
| *B01D 15/16* | (2006.01) |
| *B01D 15/36* | (2006.01) |
| *B01D 15/42* | (2006.01) |

(52) U.S. Cl.
CPC .......... *A61K 36/28* (2013.01); *A23L 2/52* (2013.01); *A23L 33/105* (2016.08); *A61K 31/216* (2013.01); *A61K 36/185* (2013.01); *B01D 15/125* (2013.01); *B01D 15/161* (2013.01); *B01D 15/363* (2013.01); *B01D 15/426* (2013.01); *A23V 2002/00* (2013.01); *A61K 2236/31* (2013.01); *A61K 2236/331* (2013.01); *A61K 2236/333* (2013.01); *A61K 2236/37* (2013.01); *A61K 2236/39* (2013.01); *A61K 2236/55* (2013.01)

(58) Field of Classification Search
None
See application file for complete search history.

(56) References Cited

U.S. PATENT DOCUMENTS

| 4,872,987 | A | 10/1989 | Kopsch |
| 4,892,938 | A | 1/1990 | Giovanetto |
| 5,888,549 | A | 3/1999 | Buchholz |
| 5,972,120 | A | 10/1999 | Kutowy |
| 6,337,095 | B1 | 1/2002 | Jain |
| 7,279,184 | B2 | 10/2007 | Gow |
| 7,291,352 | B2 | 11/2007 | Gow |
| 7,294,353 | B2 | 11/2007 | Gow |
| 7,651,717 | B2 | 1/2010 | Shioya |
| 7,750,053 | B2 | 7/2010 | Suzuki |
| 7,767,238 | B2 | 8/2010 | Roy |
| 7,838,044 | B2 | 11/2010 | Abelyan |
| 7,939,563 | B2 | 5/2011 | Suzuki |
| 8,088,428 | B2 | 1/2012 | Yamane |
| 8,178,148 | B2 | 5/2012 | Fujii |
| 8,197,875 | B2 | 6/2012 | Chien |
| 8,241,680 | B2 | 8/2012 | Williams |
| 8,293,302 | B2 | 10/2012 | Abelyan |
| 8,337,929 | B2 | 12/2012 | Ogura |
| 8,530,527 | B2 | 9/2013 | Markosyan |
| 8,586,106 | B2 | 11/2013 | Ya |
| 8,728,545 | B2 | 5/2014 | Chabot |
| 9,133,229 | B2 | 9/2015 | Lee |
| 9,358,264 | B2 | 6/2016 | Ibarra |
| 9,457,009 | B2 | 10/2016 | Guthrie |
| 9,510,611 | B2 | 12/2016 | Purkayastha |
| 9,636,373 | B1 | 5/2017 | Akao |
| 9,775,822 | B2 | 10/2017 | Prasad |
| 9,844,576 | B2 | 12/2017 | Brownell |
| 9,848,624 | B2 | 12/2017 | Ley |
| 9,889,107 | B2 | 2/2018 | Guthrie |

(Continued)

FOREIGN PATENT DOCUMENTS

| CN | 1100894 A | 4/1995 |
| CN | 1336333 A | 2/2002 |

(Continued)

OTHER PUBLICATIONS

Ali, Si, "HPLC-Analysis of Polyphenolic Compounds and Free Radical Scavenging Activity of Pomegranate Fruit (*Punica granatum* L.)." International Journal of Pharmaceutical and Clinical Research, vol. 6. No. 4. 2014.

Amberlite™ FPA53 FDA approval letter and Product Data Sheet, DOW, Mar. 5, 2012.

Anonymous, "Stevia production process | Cargill no-calories sweeteners | Cargill", Nov. 4, 2020 (Nov. 4, 2020), Retrieved from the Internet URL:https://www.cargill.com/food-beverage/emea/stevia-based-sweeteners-production-process.

Bartoshuk et al., "Sweet Taste of Water Induced by Artichoke," Dec. 1, 1972, Science, 178 (4064), 988-990.

Berte et al. (2011) J. Agric. Food Chem. 59: 5523-5527. (Year: 2011).

(Continued)

*Primary Examiner* — Russell G Fiebig

(57) ABSTRACT

A method for making a caffeoylquinic composition from a botanical source is disclosed. The method may include chromatographing an extract of biomass on an ion exchange stationary phase and obtaining an eluent comprising a caffeoylquinic composition. The biomass may be *Stevia* or yerba mate, for example. The caffeoylquinic composition includes one or more of monocaffeoylquinic acid, dicaffeoylquinic acid, and salts of the foregoing.

33 Claims, 13 Drawing Sheets

(56) References Cited

U.S. PATENT DOCUMENTS

| | | |
|---|---|---|
| 9,962,356 B2 | 5/2018 | Prasad |
| 10,188,125 B2 | 1/2019 | Ozato |
| 10,376,521 B2 | 8/2019 | Zaworotko |
| 10,420,744 B2 | 9/2019 | Prasad |
| 10,602,758 B2 | 3/2020 | Dubois |
| 10,772,340 B2 | 9/2020 | Hotta |
| 10,798,961 B2 | 10/2020 | Marcq |
| 10,973,794 B2 | 4/2021 | Forbes |
| 11,000,497 B2 | 5/2021 | Prasad |
| 2001/0051195 A1 | 12/2001 | Miljkovic |
| 2002/0187239 A1 | 12/2002 | Miljkovic |
| 2003/0003212 A1 | 1/2003 | Chien |
| 2006/0171938 A1 | 8/2006 | Stock |
| 2010/0099857 A1 | 4/2010 | Evans |
| 2011/0123505 A1 | 5/2011 | Ueda |
| 2012/0295857 A1* | 11/2012 | Goel ............. A61K 36/48 514/26 |
| 2013/0108718 A1 | 5/2013 | Chabot |
| 2014/0004215 A1 | 1/2014 | Brownell |
| 2016/0355456 A1 | 12/2016 | Toyohara |
| 2017/0055548 A1 | 3/2017 | Chakraborty |
| 2017/0095433 A1 | 4/2017 | Carter |
| 2017/0095443 A1 | 4/2017 | Luo |
| 2018/0103670 A1 | 4/2018 | Recenti |
| 2018/0168212 A1 | 6/2018 | Markosyan |
| 2018/0177216 A1 | 6/2018 | Markosyan |
| 2019/0175499 A1 | 6/2019 | Zhang |
| 2019/0274985 A1 | 9/2019 | Hotta |
| 2020/0009208 A1 | 1/2020 | Hwang |
| 2020/0023021 A1 | 1/2020 | Lewis |
| 2020/0085778 A1 | 3/2020 | Yamamoto |
| 2020/0138056 A1 | 5/2020 | Graz |
| 2020/0138765 A1 | 5/2020 | Prasad |
| 2020/0154737 A1 | 5/2020 | Dubois |
| 2020/0196649 A1 | 6/2020 | Mitchell |
| 2020/0197342 A1 | 6/2020 | Russo |
| 2020/0237845 A1 | 7/2020 | Suzuki |
| 2020/0275682 A1 | 9/2020 | Chakraborty |
| 2020/0305483 A1 | 10/2020 | Gan |
| 2020/0345049 A1 | 11/2020 | Galano |
| 2021/0037851 A1 | 2/2021 | Fraser |
| 2021/0051976 A1 | 2/2021 | Fraser |
| 2021/0084949 A1 | 3/2021 | Banavara |
| 2021/0092986 A1 | 4/2021 | Dubois |
| 2021/0128600 A1 | 5/2021 | Rauch |
| 2021/0153536 A1 | 5/2021 | Ozato |
| 2021/0236450 A1 | 8/2021 | Guthrie |
| 2021/0260013 A1 | 8/2021 | Lee |
| 2021/0267243 A1 | 9/2021 | Peterson |

FOREIGN PATENT DOCUMENTS

| | | |
|---|---|---|
| CN | 1326827 A | 8/2005 |
| CN | 1651398 A | 8/2005 |
| CN | 102381974 A | 3/2012 |
| CN | 103040064 A | 4/2013 |
| CN | 102224933 B | 7/2013 |
| CN | 102924544 B | 4/2015 |
| CN | 107027930 A | 8/2017 |
| CN | 107184482 A | 9/2017 |
| DE | 102014016495 A1 | 5/2016 |
| EP | 0730830 A | 9/1996 |
| EP | 1716757 B1 | 7/2009 |
| EP | 2896301 B1 | 6/2016 |
| EP | 2643007 B1 | 8/2016 |
| EP | 3052074 A1 | 8/2016 |
| EP | 2625962 B1 | 6/2017 |
| EP | 3257507 A1 | 12/2017 |
| EP | 3264919 A1 | 1/2018 |
| EP | 2409696 B1 | 6/2018 |
| EP | 2725007 B1 | 10/2018 |
| EP | 2753188 B1 | 1/2019 |
| EP | 2856883 B1 | 3/2019 |
| EP | 3397072 B1 | 7/2019 |
| EP | 3513663 A1 | 7/2019 |
| EP | 3169166 B1 | 8/2019 |
| EP | 3524062 A2 | 8/2019 |
| EP | 2124647 B2 | 12/2019 |
| EP | 3228195 B1 | 1/2020 |
| EP | 3544445 B1 | 5/2020 |
| JP | 58138347 A | 8/1983 |
| JP | 63173531 A | 7/1988 |
| JP | 04145048 A | 5/1992 |
| JP | 0994080 A | 4/1997 |
| JP | 09266767 A | 10/1997 |
| JP | 2009201473 A | 9/2009 |
| JP | 2011168543 A | 9/2011 |
| JP | 2016069324 A | 5/2016 |
| KR | 20070067199 A | 6/2007 |
| KR | 20110043194 A | 4/2011 |
| KR | 101227737 B1 | 1/2013 |
| KR | 101500485 B1 | 3/2015 |
| WO | 1998042209 A1 | 10/1998 |
| WO | 2000030464 A1 | 6/2000 |
| WO | 2002041700 A1 | 5/2002 |
| WO | 2007061795 A1 | 5/2007 |
| WO | 2008147725 A1 | 12/2008 |
| WO | 2011112892 A1 | 9/2011 |
| WO | 2013096420 A1 | 6/2013 |
| WO | 2014060244 A1 | 4/2014 |
| WO | 2014146135 A2 | 9/2014 |
| WO | 2014153000 A1 | 9/2014 |
| WO | 2017196933 A1 | 11/2017 |
| WO | 2019071180 A1 | 4/2019 |
| WO | 2020172276 W | 8/2020 |
| WO | 2020202193 W | 10/2020 |
| WO | 2020210161 A1 | 10/2020 |
| WO | 2020237060 A1 | 11/2020 |
| WO | 2021038830 W | 3/2021 |
| WO | 2021038832 W | 3/2021 |
| WO | 2021049864 W | 3/2021 |
| WO | 2021081417 A1 | 4/2021 |
| WO | 2021090989 A1 | 5/2021 |
| WO | 2021091322 A1 | 5/2021 |
| WO | 2021091327 A1 | 5/2021 |
| WO | 2021125070 A1 | 6/2021 |
| WO | 2021132439 W | 7/2021 |

OTHER PUBLICATIONS

Cilliers, et al., "Total polyphenols in apples and ciders; correlation with chlorogenic acid," Journal of Food Science, vol. 55, No. 5, 1990, pp. 1458-1459.

Clifford, "Chlorogenic acids and other cinnamates—nature, occurance, and dietary burden," Journal of the Science of Food and Agriculture, 79:362-372 (1999).

Craig et al., "Performance review of a fast HPLC-UV method for the quantification of chorogenic acids in green coffee bean extracts," Taianta, 154 (2016) 481-485.

Cros et al., "Solvent Extraction of Oil and Chlorogenic Acid from Green Cofffee Part I: Equilibrium Data," Journal of Food Engineering 10 (1989) 1-11.

Deladino et al. (2013) Food and Nutrition Sciences 4: 154-162 (Year: 2013).

Diaion WA10, Mitsubishi Chemical, commercial product available since at least 1998.

Edgar Naegele, "Determination of Chlorogenic Acid in Coffee Products According to DIN 10767," Sep. 1, 2016, Agilent Technology, Inc.

Fu et al., "Production of chlorogenic acid and its derivatives in hairy root cultures of Stevia rebaudiana," Jan. 14, 2015, Journal of Agriculatural and Food Chemistry, 63(1):262-268.

Gawel-Beben et al., "Stevia rebaudiana Bert. Leaf extracts as a multifunctional source of natural antioxidants," Molecules, Mar. 27, 2015.

Hernandez T et al., "Variations in the phenolic composition of fruit juices with different treatments," European Food Research and Technology, vol. 204, No. 2, 1997, p. 151-155.

International Search Report and Written Opinion dated Sep. 10, 2020 to International Application No. PCT/US2020/026885 (15 pages).

(56) References Cited

OTHER PUBLICATIONS

Kellie P Burris et al, "Composition and Bioactive Properties of Yerba Mate (*Ilex paraguariensis* A. St.-Hil.): A Review", Chilián Jun. 2012 (Jun. 2012), p. 268-275.
Kremr et al., "Unremitting Problems with Chlorogenic Acid Nomenclature: A Review," Quim. Nova, vol. 39, No. 4, 530-533, 2016.
Ky et al., "Camparison of Five Purification Methods for Chlorogenic Acids in Green Coffee Beans (*Coffea* sp.)," J. Agric. Food Chem. 1997, 45, 786-790, obtained from https://horizon.documentation.ird.fr/exl-doc/pleins_textes/pleins_textes_6/b_fdi_47-48/010010457.pdf.
Lee et al., "Chicoric acid: chemistry distribution, and production," Frontiers in Chemistry, 2013, 1(40).
Maietta et al., "Artichoke (*Cynara cardunculus* L. var. *scolymus*) waste as a natural source of carbonyl trapping and antiglycative agents," Food Research International, 100 (2017) 780-790.
Meinhart et al., "Analysis of chlorogenic acids isomers and caffeic acid in 89 herbal infusions (tea)," Journal of Food Composition and Analysis, 73 (2018) 76-82.
Meinhart et al., "Chlorogenic acid isomer contents in 100 plants commercialized in Brazil," Food Research International, 99 (2017) 522-530.
Meireles et al., "Stevia (Stevia rebaudiana Bertoni):—Futuristic view of the sweeter side of life," Floriculture, Ornamental and Plant Biotechnology vol. IV, 2006, Global Science Books.
Moller et al., "Analysis of Quinic Acid Esters of Hydroxycinnamic acids in Plant Material by Capillary Gas Chromatography and High-Performance Liquid Chromatography," Journal of Chromatography, 241(1982) 371-379.
Ohta et al., "Characterization of Novel Steviol Glycosides from Leaves of *Stevia rebaudiana* Morita," 2010, J. Appl. Glycosci., 57, 199-209.
Puangpraphant et al. (2011) Mol. Nutr. Food Res. 55: 1509-1522. (Year: 2011).
Relite RAM2, Resindion Resins for Food Treatments, 2016.
Rogers et al., "Changes to the content of sugars, sugar alcohols, myo-inositol, carboxylic acids and inorganic anions in developing grains from different varieties of Robusta (*Coffea canephora*) and Arabica (*C. arabica*) coffees," Plant Science, 1999, 149, 115-123.
Schmidt J. M. et al., "A New Two-Step Chromatographic Procedure for Fractionation of Potato Proteins with Potato Fruit Juice and Spray-Dried Protein as Source Materials", Food and Bioprocess Technology, an International Journal, Springer-Berlag, New York, vol. 10, No. 11, Jul. 26, 2017, pp. 1946-1958, XP036329673, ISSN: 1935-5130, DOI:10.1007/S11947-017-1966-4.
Sepabeads SP70, Mitsubishi Chemical, commercial product available since at least 2002.
Shibata et al., "Glucosylation of steviol and steviol-glucosides in extracts from Stevia rebaudiana Bertoni," Plant Physiol., 1991, 95, 152-156.
Standard Method Performance Requirements (SMPRs) for Determination of Phenolic Compounds in Dietary Supplements and Dietary Ingredients Containing Echinacea, Sep. 22, 2017, AOAC International.
Suarez-Quiroz et al., "Isolation of green coffee chlorogenic acids using activated carbon," Journal of Food Composition and Analysis, 2014, 33:55-58.
Trugo et al., Chlorogenic Acid Composition of Instant Coffees, Analyst, Mar. 1984, vol. 109, pp. 263-266.
Weidel et al., "A Rapid Method for Quantifying Chlorogenic Acid Levels in Potato Samples," Journal of AOAC International, vol. 97, No. 3, Nov. 3, 2014.
Wildermuth et al., "Chlorogenic acid oxidation and its reaction with sunflower proteins to form green-colored complexes," Comprehensive Reviews in Food Science and Food Safety, 2016, vol. 15, 829-843.
Xing et al. (2012) J. Zhejiang Univ.—Sci. B (Biomed and Biotech) 13(6): 487-493 (Year: 2012).

Abeywardena M. Y., et al. (2010) Acute administration of chlorogenic acid reduces blood pressure in the rat. Hypertension 55, 1493 [abstract 002]. DOI:10.1161/HYP.0b013e3181df4279.
Albas C. S., et al (2014) Avalição da genotoxicidade da *Ilex paraguariensis* (erva mate) pelo teste do micronucleo [Evaluation of the genotoxicity of *Ilex paraguariensis* (yerba mate) by micronucleus test]. Rev. Bras. Plantas Med. 16, 2, Suppl 1, 345-349 [Portuguese, English abstract], DOI:10.1590/1983-084X/12_058.
Alkhatib A. and Atcheson, R. (2017) Yerba maté (*Ilex paraguariensis*) metabolic, satiety, and mood state effects at rest and during prolonged exercise. Nutrients 9, 882 [15pp], DOI:10.3390/nu9080882.
Baeza Gema et al: "Dihydrocaffeic acid, a major microbial metabolite of chlorogenic acids, shows similar protective effect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI:10.1016/J.FOODRES.2016.06.011.
Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI:10.1186/s12937-018-0426-y.
Bariana D. S., et al. (1965) Chlorogenic acid: further evidence for its antigenic and allergenic activity. Nature 207, 1155-1157. DOI:10.1038/2071155a0.
Bidau C. J., et al. (2004) Evaluation of the genotoxicity of aqueous extracts of Ilex paraguariensis St. Hil. (Aquifoliaceae) using the Allium test. Cytologia 69, 109-117. DOI:10.1508/cytologia.69.109.
Boaventura B. C., et al (2012) Association of mate tea (*Ilex paraguariensis*) intake and dietary intervention and effects an oxidative stress biomarkers of dyslipidemic subjects. Nutrition 28, 657-664. DOI:10.1016/j.nut.2011.10.017.
Boaventura B. C., et al (2013) Antioxidant potential of mate tea (Ilex paraguariensis) in type 2 diabetic mellitus and pre-diabetic individuals. J. Funct. Foods 5, 1057-1064. DOI:10.1016/j.jff.2013.03.001.
Boaventura B. C., et al (2015) Effect of yerba mate (*Ilex paraguariensis* A. St. Hil.) infusion obtained by freeze concentration technology on antioxidant status of healthy individuals. LWT Food Sci. Technol. 62, 948-954. DOI:10.1016/j.lwt.2015.02.028.
Boaventura, B. C. B., et al (2013). Enhancement of bioactive compounds content and antioxidant activity of aqueous extract of mate (*Ilex paraguariensis* A. St. Hil.) through freeze concentration technology. Food Research International, 53, 686e692.
Borges M. C., et al. (2013) The effect of mate tea (*Ilex paraguariensis*) on metabolic and inflammatory parameters in nigh-fat diet-fed Wistar rats. Int J. Food Sci. Nutr. 64, 561-569 001:10.3109/09637486.2012.759188.
Bortoluzzi M.-C., et al (2014) Frequency of micronucleus in oral epithelial cells after exposure to mate-tea in healthy humans. Med. Oral Patol. Oral Cir. Bucal. 19, e345-e349. DOI:10.4317/medoral.19570.
Carvalho Ribeiro M., et al (2017) The effects of roasted yerba mate (*Ilex paraguariensis* A. St. Hil.) consumption on glycemia and total serum creatine phosphokinase in patients with traumatic brain injury. J. Funct. Foods 28, 240-245. DOI:10.1016/j.jff.2016.11.
Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.
Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.
Cuesta A., et al (2018) Efecto agudo del consumo de yerba mate (*Ilex paraguariensis*) sobre el ritmo cardíaco en pacientes derivados para estudio Holter [Acute effect of yerba mate (*Ilex paraguariensis*) consumption on heart rhythm in patients referred for Holter study] [epub ahead of print]. Arch. Cardiol. Mex. xxx, Jun. 2, 2018 [1-6] [Spanish, English abstract], DOI:10.1016/j.acmx.2018.05.004.
De Andrade F., Coehlo de Albuquerque C. A., Maraschin M. and da Silva E. L. (2012) Safety assessment of yerba mate (*Ilex paraguariensis*)

(56) References Cited

OTHER PUBLICATIONS dried extract: results of acute and 90 days subchronic toxicity studies in rats and rabbits. Food Chem. Toxicol. 50, 328-334. DOI:10.1016/j.fct.2011.08.028.

De Meneses Fujii et al. (2014) Yerba Mate (*Ilex paraguariensis*) modulates NF-kappaB pathway and AKT expression in the liver of rats fed on a high-fat diet. Int. J. Food Sci. Nutr. 65, 967-976. DOI:10.3109/09637486.2014.945153.

De Morais E. C., et al (2009) Consumption of yerba mate (*Ilex paraguariensis*) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.

Eklund A. (1975) Effect of chlorogenic acid in a casein diet for rats. Nutritional and pathological observations. Nutr. Metab. 18, 258-264. DOI:10.1159/000175603.

Enokuchi Y., et al. (2020) Effects of chlorogenic acids on menopausal symptoms in healthy women: a randomized, placebo-controlled, double-blind, parallel-group trial. Nutrients 12, 3757 [12pp] DOI:10.3390/nu12123757.

Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.

Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.

Fonseca C. A., et al (2000) Nontoxic, mutagenic, and clastogenic activities of mate-chimarrao (*Ilex paraguariensis*). J. Environ. Pathol. Toxicol. Oncol. 19, 333-346.

Frank J., et al. (2003) The dietary hydroxycinnamate caffeic acid and its conjugate chlorogenic acid increase vitamin E and cholesterol concenlialions in Sprague-Dawley rats. J. Agric. Food Chem. 51, 2526-2531. DOI:10.1021/if026127k.

Freedman S. O., et al. (1961) Chlorogenic acid: an allergen in green coffee bean. Nature 192, 241-243. DOI:10.1038/192241a0.

Freedman S. O., et al. (1964) Antigenic and allergenic properties of chlorogenic acid man, rabbit, guinea pig. Can. Med. Assoc. J. 90, 473-474.

Gebara K. S., et al. (2020) A randomized crossover intervention study on the effect a standardized mate extract (*Ilex paraguariensis* A. St.-Hil.) in Men predisposed to cardiovascular risk. Nutrients, 13, 14 [14pp], DOI:10.3390/nu13010014.

Gomez-Juaristi M., Martinez-López S., Sarria B., Bravo L. and Mateos R. (2018) Absorption and metabolism of yerba mate phenolic compounds in humans Food Chem. 240, 1028-1038 DOI:10.1016/j.foodchem.2017.08.003.

Gonthier M.-P., et al. (2006) Microbial metabolism of caffeic acid and its esters chlorogenic and caftaric acids by human faecal microbiota in vitro Biomed. Pharmacother. 60, 536-540 DOI:10.1016/j.biopha.2006.07.084.

Grzesiuk J. D., et al. (2012) Evaluation of mutagenicity and antimutagenicity of Ilex paraguariensi} A. St.-Hil.: Aquifoliaceae infusion de Allium cepa assay. Arq. Cienc. Saude UNIPAR 16, 73-78. DOI:10.25110/arqsaude.v16i2.2012.4840.

Gu R., et al. (2007) Simultaneous determination of 1,5-dicaffeoylquinic acid and its active metabolites in human plasma by liquid chromatography-tandem mass spectrometry for pharmacokinetic studies. J. Chromatogr. B. 852, 85-91. DOI:10.1016/j.jchromb.2006.12.055.

Hernandes L. C., et al. (2016) Cytotoxicity and genotoxicity of chlorogenic acid alone or associated with the demethylating drug 5-azacytidine in Jurkat cells. Toxicol. Lett. 258, Suppl. S, S56 [abstract OSC01-007]. DOI:10.1016/i.toxlet2016.06.1295.

IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).

IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496 Lyon, France: International Agency for Research on Cancer (IARC), Lyon, France.

Jin S., et al. (2015) Chlorogenic acid improves late diabetes through adiponectin receptor signaling pathways in db/db mice. PLoS ONE 10, e0120842 [15pp] DOI:10.1371/journal.pone.0120842.

Kato M., et al. (2018) Effect of chlorogenic acid intake on cognitive function in the elderly: a pilot study. Evid. Based. Complement. Alternat. Med. 2018, Article ID 8608497 [8pp] 001:10.1155/2018/8608497.

Kim H. J., et al. (2012) Effect of green mate in overweight volunteers: a randomised placebo-controlled human study. J. Funct. Foods 4,287-293. DOI:10 1016/j.jff.2011.12.005.

Kim S.-Y., et al. (2015) Anti-obesity effects of Yerba Mate (*Ilex paraguariensis*): a randomized, double-blind, placebo-controlled clinical trial. BMC Complement. Altern. Med. 15, 338 [8pp]. DOI:10.1186/s12906-015-0859-1.

Klein G. A., et al (2011) Mate tea (*Ilex paraguariensis*) improves glycemic and lipid profiles of type 2 diabetes and pre-diabetes individuals: a pilot study. J Am. Coll. Nutr. 30, 320-332.

Kujawska M (2018) Yerba mate (*Ilex paraguariensis*) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.

Laird Layton L., et al. (1964) Pure chlorogenic acid is not allergenic in atopy to green coffee: A specific protein probably is involved. Nature 203,188-189. DOI:10.1038/203188a0.

Leitao A. C. and Braga R. S. (1994) Mutagenic and genotoxic effects of mate (*Ilex paraguariensis*) in prokaryotic organisms. Braz. J. Med. Biol. Res. 27, 1517-1525.

Lin M., et al. (2013) Evaluation of the potential sensitization of chlorogenic Acid: a meta-analysis. Evid. Based. Complement. Alternat. Med. 2013, Article ID 208467 DOI:10.1155/2013/208467.

Liu B., et al. (2017) Preparation, phytochemical investigation, and safety evaluation of chlorogenic acid products from Eupatorium adenophorum. Molecules 22, 67 [12pp]. DOI:10.3390/molecules22010067.

Liu Z., et al. (2010) Evaluation of the immunosensitizing potential of chlorogenic acid using a popliteal lymph node assay in BALB/c mice Food Chem. Toxicol. 48, 1059-1065. DOI:10.1016/j.fct.2010.01.024.

Lorena Deladino et al: "Major Phenolics in Verba Mate Extracts (*Ilex paraguariensis*) and Their Contribution to the Total Antioxidant Capacity", Food and Nutrition Sciences, vol. 04, Aug. 1, 2013 (Aug. 1, 2013), pp. 154-162, XP055588480, ISSN: 2157-944X, DOI: 10.4236/fns.2013.48A019.

Lowell F. C. (1965) Allergenicity of chlorogenic acid. J. Allergy 36, 308. DOI:10.1016/0021-8707(65)90091-2.

Marques V. X. and Farah A. (2010) Urinary excretion of chlorogenic acids and metabolites in humans after green mate (*I. paraguariensis*) consumption. FASEB J. 24, 1, Suppl., [abstract 922 1] DOI:10.1096/fasebj.24.1_supplement.922.1.

Matsumoto R. L. T., et al. (2009) Effects of maté tea (*Ilex paraguariensis*) ingestion on mRNA expression of antioxidant enzymes, lipid peroxidation, and total antioxidant status in healthy young women. J. Agric. Food Chem. 57, 1775-1780. DOI:10.1021/jf803096g.

Mello F. W., et al. (2018) Mate consumption association with upper aerodigestive tract cancers: a systematic review and meta-analysis. Oral Oncol. 82, 37-47 [plus supplementary data]. DOI:10.1016/j.oraloncology.2018.04.023.

Messina D., et al. (2017) Mate tea and lipid profile in overweight women under caloric restriction. Ann Nutr. Metab. 71, 384 [abstract 144-1131] DOI:10.1159/000480486.

Mikulasova M., et al. (2005) Genotoxic effects of the hydroxycinnamic acid derivatives—caffeic, chlorogenic and cichoric acids. Biologia (Bratisl.) 60, 275-279.

Minuzzi Becker A., et al. (2019) Spray-dried yerba mate extract capsules: clinical evaluation and antioxidant potential in healthy

(56) References Cited

OTHER PUBLICATIONS individuals. Plant oods Hum. Nutr. 74, 495-500 [plus supplementary tables], DOI:10.1007/311130-019-00764-4.
Miranda D. D. C., et al. (2008) Protective effects of mate tea (*Ilex paraguariensis*) on H2O2-induced DNA damage and DNA repair in mice. Mutagenesis 23, 261-265. DOI:10.1093/mutage/gen011.
Monteiro M., et al. (2007) Chlorogenic acid compounds from coffee are differentially absorbed and metabolized in humans. J. Nutr. 137, 2196-2201. DOI:10.1093/jn/137.10.2196.
Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.
Nakamura S., et al. (2006) [Pharmacokinetics of chlorogenic acids absorbed in human plasma and their metabolites following oral ingestion of coffee drink]. Yakuri to Chiryo [Jpn. Pharmacol. Ther.] 34, 1239-1246.
Naylor L. H., et al. (2021) Acute dose-response effect of coffee-derived chlorogenic acids on the human vasculature n healthy volunteers: a randomized controlled trial. Am. J. Clin. Nutr. 113, 370-379. DOI:10.1093/ajcn/nqaa312.
Nowacki L. C., et al. (2021) Ilex paraguariensis extract as an alternative to pain medications. Acta Pharm. 71, 383-398 DOI:10.2478/acph-2021-0029.
Ochiai R., et al. (2019) Effect of chlorogenic acids on cognitive function in mild cognitive impairment: a randomized controlled crossover trial. J. Alzheimers Dis. 72, 1209-1216 [plus supplementary tables] DOI:10.3233/jad-190757.
Olthof M. R., et al. (2001a) Consumption of high doses of chlorogenic acid, present in coffee, or of black tea increases plasma total homocysteine concenlialions in humans. Am. J. Clin. Nutr. 73, 532-538. DOI:10.1093/ajcn/73.3.532.
Olthof M. R., et al. (2001b) Chlorogenic acid and caffeic acid are absorbed in humans. J. Nutr. 131, 66-71. DOI:10.1093/jn/131.1.66.
Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.
Onakpoya I. J., et al. (2015) The effect of chlorogenic acid on blood pressure: a systematic review and meta-analysis of randomized clinical trials. J. Hum. Hypertens. 29, 77-81 [plus supplementary data], DOI:10.1038/ihh.2014.46.
Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.
Pereira Panza V., et al. (2019) Effect of mate tea (*Ilex paraguariensis*) on the expression of the leukocyte NADPH oxidase subunit p47phox and on circulating inflammatory cytokines in healthy men: a pilot study. Int. J. Food Sci. Nutr. 70, 212-221 DOI:10.1080/09637486.2018.1486393.
Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390::AID-JSFA258>3.0.CO;2-0.
Renouf M., et al. (2014) Dose-response plasma appearance of coffee chlorogenic and phenolic acids in adults. Mol. Nutr. Food Res. 58, 301-309. DOI:10.1002/mnfr.201300349.
Richling E., et al. (2012) Dose-response relationship of chlorogenic acids in humans. Naunyn Schmiedebergs ArchPharmacol. 385, S75 [abstract 327]. DOI:10.1007/s00210-012-0736-0.
Rocha D. S., et al. (2018) Effect of yerba mate (*Ilex paraguariensis*) extract on the metabolism of diabetic rats. Biomed. Pharmacother. 105, 370-376 [plus supplementary figure]. DOI:10.1016/j.biopha.2018.05.132.
Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/mf.2018.0060.
Sanchez Boado L., et al. (2018) Effects of Ilex paraguariensis polyphenols on magnesium absortion and iron bioavailability: preliminary study. J Food Res. 7, 114-126. DOI:10.5539/jfr.v7n2p114.
Sarria B., et al. (2020a) Yerba mate may prevent diabetes according to a crossover, randomized, controlled study in humans. Proc. Nutr. Soc. 79, OCE2, E245 DOI:10.1017/S0029665120001937.
Sarria B., et al. (2020b) Yerba mate improves cardiovascular health in normocholesterolemic and Typercholesterolemic subjects. Proc. Nutr. Soc. 79, OCE2, E635. DOI: 10.1017/S0029665120005844.
Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.
Simao Do Carmo L., et al. (2013) The effects of yerba maté (*Ilex paraguariensis*) consumption on IL-1, IL-6, TNF-α and IL-10 production by bone marrow cells in Wistar rats fed a high-fat diet. Int J Vitam Nutr Res 83, 26-35. DOI: 10.1024/0300-9831/a000142.
Sirima Puangpraphant et al: "Dicaffeoylquinic acids in Verba mate (*Ilex paraguariensis* St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, Oct. 8, 2011 (Oct. 8, 2011), pp. 1509-1522, XP055175515, ISSN: 1613-4125, DOI: 10.1002/mnfr.201100128.
Song Z., et al. (2014) [Effect of chlorogenic acid at high dose on expression of hepatic inflammatory cytokines mRNA induced by lipopolysaccharides]. Ying Yang Xue Bao [Acta Nutr. Sin. ] 36, 481-485.
Souza S. J., et al. (2017) Effect of chocolate and mate tea on the lipid profile of individuals with HIV/AIDS on antiretroviral therapy: A clinical trial. Nutrition 43-44, 61-68. DOI:10.1016/j.nut.2017.06.017.
Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.
Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.
Stich H. F., et al. (1981) A comparative genotoxicity study of chlorogenic acid (3-0-caffeoylquinic acid). Mutat. Res. 90, 201-212. DOI:10.1016/0165-1218(81)90001-X.
Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.
U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.
U.S. FDA (2018) Part 182—Substances generally recognized as safe. Section §182.20—Essential oils, oleoresins (solvent-free), and natural extractives (including distillates). In: U.S. Code of Federal Regulations (CFR). Title 21: Food and Drugs. (U.S. Food and Drug Administration). U.S. Government Printing Office (GPO), Washington, DC.
Vargas Alves R. J., et al. (2008) The evaluation of maté (*Ilex paraguariensis*) genetic toxicity in human lymphocytes by the cytokinesis-block in the micronucleus assay. Toxicol. In Vitro 22, 695-698. DOI:10.1016/j.tiv.2007.11.005.
Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.
Wantanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.
Wei Z.-M., et al. (2010) [Clinical tolerability of 1,5-dicaffeoylquinic acid tablets]. Zhongguo Xin Yao Za Zhi [Chin. J. New Drugs] 19, 106-108.

(56) References Cited

OTHER PUBLICATIONS

Wnuk M., et al. (2009) Evaluation of the cyto- and genotoxic activity of yerba mate (*Ilex paraguariensis*) in human lymphocytes in vitro Mutat. Res. 679, 18-23. DOI:10.1016/j.mrgentox.2009.07.017.

Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.

Yara Queiroz et al: The Chlorogenic Acid and Caffeine Content of Verba Mate (*Ilex paraguariensis*) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821 pdf [retrieved on Jul. 15, 2020].

Yu S., et al. (2015) *Yerba mate* (Ilex paraguariensis) improves microcirculation of volunteers with high blood viscosity: a randomized, double-blind, placebo-controlled trial. Exp. Gerontol. 62, 14-22 [plus supplementary tables]. DOI:10.1016/j.exger.2014.12.016.

Zhu Y., et al. (2017) [Effect of caffeine and chlorogenic acid on body weight, lipid accumulation and the expression of lipid metabolism-related genes in high-fat diet-fed mice]. Shipin Kexue [Food Sci. ] 38, 162-167 DOI:10.7506/spkx1002-6630-201709026.

Zuniga L. Y., et al. (2018) Effect of chlorogenic acid administration on glycemic control, insulin secretion, and insulin sensitivity in patients with impaired glucose tolerance J. Med. Food 21, 469-473 DOI:10.1089/jmf.2017.0110.

\* cited by examiner

| Peak Name | Ret. Time min | Amount ppm | Rel. Area % |
|---|---|---|---|
|  | 2.149 | 0 | 0.1 |
| Neochlorogenic acid | 2.39 | 0 | 1.8 |
|  | 2.645 | 0 | 0.1 |
|  | 2.751 | 1352 | 10.9 |
|  | 2.855 | 0 | 0.3 |
|  | 2.91 | 0 | 0.4 |
|  | 3.02 | 0 | 0.2 |
|  | 3.145 | 0 | 0.4 |
|  | 3.394 | 0 | 2.5 |
|  | 3.635 | 0 | 0.9 |
|  | 3.767 | 0 | 0.4 |
|  | 3.903 | 0 | 0.2 |
|  | 3.943 | 0 | 0.3 |
| Coumaroylquinic acid 1 | 4.032 | 31 | 0.3 |
|  | 4.173 | 0 | 0.4 |
|  | 4.29 | 0 | 0.3 |
|  | 4.399 | 0 | 0.1 |
| Chlorogenic acid | 4.544 | 1102 | 8.9 |
| Caffeic Acid | 4.693 | 26 | 0.4 |
| Cryptochlorogenic acid | 4.759 | 706 | 5.7 |
|  | 4.952 | 0 | 0.2 |
|  | 5.043 | 0 | 0.1 |
|  | 5.169 | 0 | 0.2 |
| Feruloylquinic acid 1 | 5.257 | 48 | 0.4 |
|  | 5.335 | 0 | 0.1 |
|  | 5.429 | 0 | 0.0 |
|  | 5.551 | 0 | 0.1 |
| Caffeine | 5.671 | 627 | 18.5 |
|  | 5.796 | 0 | 5.5 |
|  | 6.051 | 0 | 0.1 |
|  | 6.128 | 0 | 0.1 |
|  | 6.175 | 0 | 0.0 |
| Coumaroylquinic acid 2 | 6.242 | 12 | 0.1 |
|  | 6.314 | 0 | 0.0 |
|  | 6.49 | 0 | 0.2 |
|  | 6.691 | 0 | 0.1 |
|  | 6.77 | 0 | 0.0 |
|  | 6.971 | 0 | 0.0 |
|  | 7.05 | 0 | 0.1 |
|  | 7.143 | 0 | 0.0 |
|  | 7.23 | 0 | 0.0 |
|  | 7.289 | 0 | 0.1 |
|  | 7.36 | 0 | 0.0 |
| Feruloylquinic acid 2 | 7.45 | 23 | 0.2 |

| Peak Name | Ret. Time min | Amount ppm | Rel. Area % |
|---|---|---|---|
| Feruloylquinic acid 3 | 7.508 | 0 | 0.1 |
|  | 7.575 | 0 | 0.1 |
|  | 7.664 | 23 | 0.2 |
|  | 7.755 | 0 | 0.2 |
|  | 7.905 | 0 | 0.1 |
|  | 7.96 | 0 | 0.1 |
|  | 8.008 | 0 | 0.1 |
|  | 8.105 | 0 | 0.3 |
|  | 8.2 | 0 | 0.1 |
|  | 8.309 | 0 | 0.2 |
|  | 8.397 | 0 | 0.2 |
|  | 8.491 | 0 | 0.1 |
|  | 8.6 | 0 | 1.5 |
|  | 8.665 | 0 | 0.1 |
|  | 8.746 | 0 | 0.1 |
|  | 8.852 | 0 | 0.3 |
|  | 8.937 | 0 | 0.1 |
|  | 9.021 | 0 | 0.1 |
|  | 9.097 | 0 | 0.2 |
|  | 9.209 | 0 | 0.3 |
| Rutin | 9.34 | 364 | 5.0 |
|  | 9.55 | 0 | 0.9 |
|  | 9.6 | 0 | 0.3 |
|  | 9.675 | 0 | 0.1 |
|  | 9.79 | 0 | 0.2 |
|  | 9.865 | 0 | 0.0 |
|  | 9.92 | 0 | 0.1 |
|  | 10.052 | 0 | 0.0 |
|  | 10.162 | 0 | 0.0 |
|  | 10.205 | 0 | 0.0 |
|  | 10.287 | 0 | 0.1 |
|  | 10.326 | 0 | 0.0 |
| 4,5-DCQA | 10.455 | 0 | 0.1 |
|  | 10.562 | 317 | 2.6 |
|  | 10.664 | 0 | 0.1 |
| Cynarin | 10.792 | 114 | 0.9 |
| 3,5-DCQA | 10.902 | 1573 | 12.7 |
|  | 11.025 | 0 | 0.4 |
|  | 11.212 | 0 | 0.1 |
| Cynarin isomer 2 | 11.275 | 16 | 0.1 |
|  | 11.336 | 0 | 0.1 |
|  | 11.413 | 0 | 0.2 |
|  | 11.505 | 0 | 0.0 |
|  | 11.585 | 0 | 0.0 |

| Peak Name | Ret. Time min | Amount ppm | Rel. Area % |
|---|---|---|---|
| Cynarin isomer 3 | 11.761 | 10 | 0.1 |
|  | 11.813 | 0 | 0.3 |
| 3,4-DCQA | 11.965 | 936 | 7.5 |
|  | 12.195 | 0 | 0.1 |
|  | 12.29 | 0 | 0.1 |
|  | 12.367 | 0 | 0.2 |
|  | 12.493 | 0 | 0.1 |
|  | 12.57 | 0 | 0.2 |
|  | 12.644 | 0 | 0.1 |
|  | 12.695 | 0 | 0.1 |
|  | 12.86 | 0 | 0.0 |
|  | 13.087 | 0 | 0.0 |
|  | 13.19 | 0 | 0.2 |
|  | 13.542 | 0 | 0.2 |
|  | 13.656 | 0 | 0.0 |
|  | 13.732 | 0 | 0.2 |
|  | 13.811 | 0 | 0.0 |
|  | 13.909 | 0 | 0.1 |
|  | 13.99 | 0 | 0.1 |
|  | 14.245 | 0 | 0.0 |
|  | 14.377 | 0 | 0.1 |
|  | 14.427 | 0 | 0.3 |
|  | 14.64 | 0 | 0.1 |
|  | 14.75 | 0 | 0.1 |
|  | 14.892 | 0 | 0.1 |
|  | 14.982 | 0 | 0.0 |
|  | 15.145 | 0 | 0.1 |
| Diferuloylquinic acid 1 | 15.55 | 6 | 0.2 |
| Diferuloylquinic acid 2 | 16.1 | 22 | 0.0 |
|  | 16.692 | 0 | 0.0 |
|  | 16.953 | 0 | 0.0 |
|  | 18.76 | 0 | 0.1 |
|  | 18.822 | 0 | 0.2 |
|  | 18.935 | 0 | 0.0 |
|  | 19.027 | 0 | 0.0 |
|  | 19.363 | 0 | 0.2 |
|  | 19.483 | 0 | 0.0 |
|  | 20.013 | 0 | 0.1 |
|  | 20.082 | 0 | 0.0 |
|  | 20.216 | 0 | 0.0 |
|  | 20.267 | 0 | 0.1 |
|  | 20.506 | 0 | 0.0 |
|  | 20.68 | 0 | 0.3 |
|  | 20.779 | 0 | 0.2 |

Fig 8

| Peak Name | Ret.Time min | Amount ppm | Rel.Area % | Peak Name | Ret.Time min | Amount ppm | Rel.Area % |
|---|---|---|---|---|---|---|---|
|  | 2.145 | 0 | 0.1 |  | 8.111 | 0 | 0.2 |
|  | 2.218 | 0 | 0.0 |  | 8.206 | 0 | 0.1 |
|  | 2.276 | 0 | 0.1 |  | 8.271 | 0 | 0.0 |
|  | 2.636 | 0 | 0.1 |  | 8.325 | 0 | 0.2 |
| Neochlorogenic acid | 2.749 | 1759 | 19.3 |  | 8.407 | 0 | 0.1 |
|  | 3.011 | 0 | 0.2 |  | 8.497 | 0 | 0.1 |
|  | 3.121 | 0 | 0.2 |  | 8.558 | 0 | 0.2 |
|  | 3.33 | 0 | 0.0 |  | 8.61 | 0 | 0.5 |
|  | 3.396 | 0 | 0.3 |  | 8.681 | 0 | 0.2 |
|  | 3.685 | 0 | 0.3 |  | 8.762 | 0 | 0.1 |
|  | 3.738 | 0 | 0.4 |  | 8.872 | 0 | 0.3 |
|  | 3.952 | 0 | 0.4 |  | 8.944 | 0 | 0.1 |
| Coumaroylquinic acid 1 | 4.039 | 24 | 0.3 |  | 9.08 | 0 | 0.3 |
|  | 4.173 | 0 | 0.3 |  | 9.215 | 0 | 0.2 |
|  | 4.306 | 0 | 0.1 | Rutin | 9.356 | 8 | 0.2 |
|  | 4.412 | 0 | 0.1 |  | 9.474 | 0 | 0.2 |
|  | 4.461 | 0 | 0.0 |  | 9.551 | 0 | 0.0 |
| Chlorogenic acid | 4.548 | 1467 | 16.1 |  | 9.639 | 0 | 0.2 |
| Caffeic Acid | 4.7 | 29 | 0.6 |  | 9.734 | 0 | 0.0 |
| Cryptochlorogenic acid | 4.763 | 1056 | 11.6 |  | 9.841 | 0 | 0.1 |
|  | 4.957 | 0 | 0.2 |  | 9.942 | 0 | 0.1 |
|  | 5.05 | 0 | 0.1 |  | 10.1 | 0 | 0.1 |
|  | 5.113 | 0 | 0.1 |  | 10.219 | 0 | 0.0 |
|  | 5.173 | 0 | 0.1 |  | 10.343 | 0 | 0.0 |
| Feruloylquinic acid 1 | 5.261 | 42 | 0.5 |  | 10.41 | 0 | 0.0 |
|  | 5.343 | 0 | 0.1 | 4,5-DCQA | 10.432 | 0 | 0.0 |
|  | 5.531 | 0 | 0.0 | Cynarin | 10.573 | 456 | 5.0 |
| Caffeine | 5.683 | 3 | 0.1 | 3,5-DCQA | 10.675 | 7 | 0.1 |
|  | 5.806 | 0 | 1.2 |  | 10.914 | 1789 | 19.6 |
|  | 5.946 | 0 | 0.0 |  | 11.171 | 0 | 0.1 |
|  | 6.051 | 0 | 0.1 | Cynarin isomer 2 | 11.289 | 12 | 0.1 |
|  | 6.185 | 0 | 0.0 |  | 11.346 | 0 | 0.0 |
| Coumaroylquinic acid 2 | 6.249 | 15 | 0.2 |  | 11.486 | 0 | 0.0 |
|  | 6.337 | 0 | 0.0 |  | 11.601 | 0 | 0.0 |
|  | 6.517 | 0 | 0.1 | Cynarin isomer 3 | 11.722 | 3 | 0.0 |
|  | 6.707 | 0 | 0.0 |  | 11.776 | 0 | 0.1 |
|  | 7.003 | 0 | 0.0 |  | 11.828 | 0 | 0.1 |
|  | 7.066 | 0 | 0.1 | 3,4-DCQA | 11.975 | 1341 | 14.7 |
|  | 7.156 | 0 | 0.0 |  | 12.357 | 0 | 0.1 |
|  | 7.294 | 0 | 0.0 |  | 12.506 | 0 | 0.1 |
|  | 7.403 | 0 | 0.0 |  | 12.657 | 0 | 0.3 |
| Feruloylquinic acid 2 | 7.462 | 26 | 0.3 |  | 12.875 | 0 | 0.1 |
|  | 7.522 | 0 | 0.1 |  | 13.204 | 0 | 0.0 |
|  | 7.581 | 0 | 0.1 |  | 13.55 | 0 | 0.3 |
| Feruloylquinic acid 3 | 7.671 | 19 | 0.2 |  | 13.74 | 0 | 0.2 |
|  | 7.721 | 0 | 0.1 |  | 13.997 | 0 | 0.1 |
|  | 7.751 | 0 | 0.0 |  | 14.386 | 0 | 0.1 |
|  | 7.913 | 0 | 0.0 |  | 14.437 | 0 | 0.3 |
|  | 7.966 | 0 | 0.1 |  | 14.761 | 0 | 0.1 |
|  | 8.014 | 0 | 0.2 | Diferuloylquinic acid 2 | 16.109 | 25 | 0.3 |

| Peak Name | Ret.Time min | Amount ppm | Rel.Area % |
|---|---|---|---|
| | 2.154 | 0 | 0.1 |
| | 2.636 | 0 | 0.3 |
| Neochlorogenic acid | 2.764 | 65 | 15.9 |
| | 3.024 | 0 | 0.1 |
| | 3.163 | 0 | 0.2 |
| | 3.412 | 0 | 0.2 |
| | 3.462 | 0 | 0.1 |
| | 3.691 | 0 | 0.1 |
| | 3.764 | 0 | 0.1 |
| | 3.97 | 0 | 0.1 |
| Coumaroylquinic acid 1 | 4.055 | 1 | 0.2 |
| | 4.196 | 0 | 0.1 |
| Chlorogenic acid | 4.564 | 85 | 20.7 |
| Caffeic Acid | 4.714 | 1 | 0.4 |
| Cryptochlorogenic acid | 4.781 | 60 | 14.8 |
| | 4.983 | 0 | 0.1 |
| Feruloylquinic acid 1 | 5.281 | 2 | 0.5 |
| | 5.364 | 0 | 0.1 |
| | 5.549 | 0 | 0.1 |
| Caffeine | 5.699 | 0 | 0.3 |
| | 5.823 | 0 | 0.7 |
| | 5.889 | 0 | 0.1 |
| | 6.066 | 0 | 0.1 |
| Coumaroylquinic acid 2 | 6.261 | 1 | 0.2 |
| | 6.528 | 0 | 0.1 |
| | 6.713 | 0 | 0.1 |
| | 7.244 | 0 | 0.1 |
| Feruloylquinic acid 2 | 7.467 | 2 | 0.5 |
| | 7.612 | 0 | 0.0 |
| Feruloylquinic acid 3 | 7.675 | 1 | 0.3 |
| | 7.73 | 0 | 0.1 |
| | 8.617 | 0 | 0.2 |
| Rutin | 9.351 | 0 | 0.1 |
| | 9.553 | 0 | 0.1 |
| | 9.64 | 0 | 0.1 |
| | 10.203 | 0 | 0.1 |
| 4,5-DCQA | 10.565 | 25 | 6.1 |
| Cynarin | 10.684 | 0 | 0.1 |
| 3,5-DCQA | 10.907 | 78 | 19.0 |
| | 11.205 | 0 | 0.1 |
| Cynarin isomer 2 | 11.279 | 1 | 0.1 |
| | 11.337 | 0 | 0.1 |
| 3,4-DCQA | 11.969 | 66 | 16.2 |
| | 12.351 | 0 | 0.1 |
| | 12.403 | 0 | 0.1 |
| | 12.649 | 0 | 0.3 |
| | 12.863 | 0 | 0.1 |
| | 13.545 | 0 | 0.2 |
| | 13.735 | 0 | 0.1 |
| | 13.998 | 0 | 0.1 |
| | 14.459 | 0 | 0.3 |
| | 14.774 | 0 | 0.1 |

METHODS FOR MAKING BOTANICAL EXTRACT COMPOSITION

CROSS-REFERENCE TO RELATED APPLICATIONS

This application is a Continuation of International Application No. PCT/US2020/026885, filed Apr. 6, 2020 and entitled "Methods for Making Botanical Extract Composition", which claims the benefit of: U.S. Application No. 62/830,448, filed Apr. 6, 2019 and entitled "*Stevia* Processing;" U.S. Application No. 62/832,273, filed Apr. 10, 2019 and entitled "Methods For Making Botanical Extract Composition;" U.S. application Ser. No. 16/373,206, filed Apr. 4, 2019 and entitled "Steviol Glycoside Solubility Enhancers," which was published on Jul. 25, 2019 as U.S. Patent Application Publication No. 2019/0223481; International Application No. PCT/US2018/054691, filed Oct. 5, 2018 and entitled "Steviol Glycoside Solubility Enhancers;" U.S. Provisional Application No. 62/569,279, filed Oct. 6, 2017, and entitled "Steviol Glycoside Solubility Enhancers;" U.S. Provisional Application No. 62/676,722, filed May 25, 2018, and entitled "Methods for Making Yerba Mate Extract Composition;" International Application No. PCT/US2018/054688 filed Oct. 5, 2018 and entitled "Methods for Making Yerba Mate Extract Composition;" and U.S. application Ser. No. 16/374,894, filed Apr. 4, 2019 and entitled "Methods for Making Yerba Mate Extract Composition" which was published on Aug. 1, 2019 as U.S. Patent Application Publication No. 2019/0231834. The entirety of each of those applications is hereby incorporated by reference.

BACKGROUND

Compositions comprising monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof can be prepared from various botanical sources. Compositions comprising monocaffeoylquinic acids, dicaffeoylquinic acids, and salts thereof may be incorporated into edible material to provide beneficial properties, including for example beneficial sensory properties. However, botanical preparations of compositions comprising monocaffeoylquinic acids, dicaffeoylquinic acids, and salts thereof can include compounds with off-tastes or other undesirable properties that limit the use of these botanical preparations.

SUMMARY

Because of the beneficial properties of compositions comprising monocaffeoylquinic acids, dicaffeoylquinic acids and salts thereof, there is an interest in methods for extracting these compounds from botanical biomass, such as botanical biomass from for example yerba mate, *Stevia*, and globe artichoke. These compounds include, but are not limited to, monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

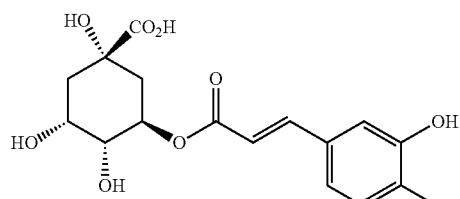

Chlorogenic acid (5-O-caffeoylquinic acid)

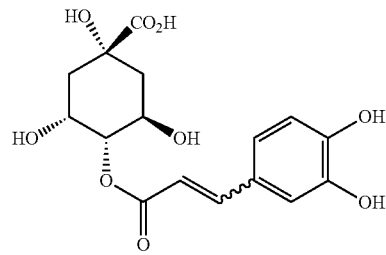

Cryptochlorogenic acid (4-O-caffeoylquinic acid)

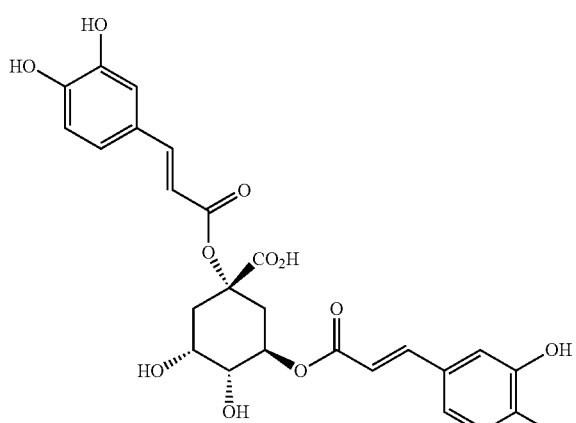

1,5-Dicaffeoylquinic acid

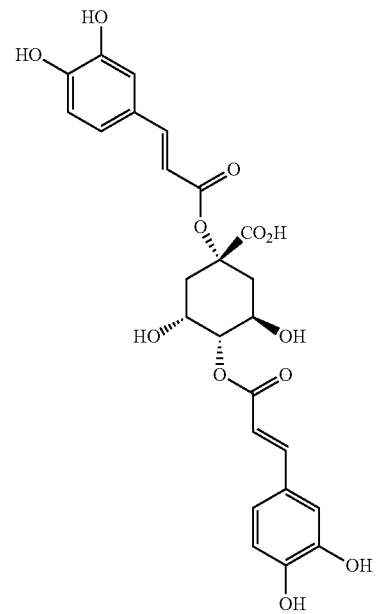

1,4-Dicaffeoylquinic acid

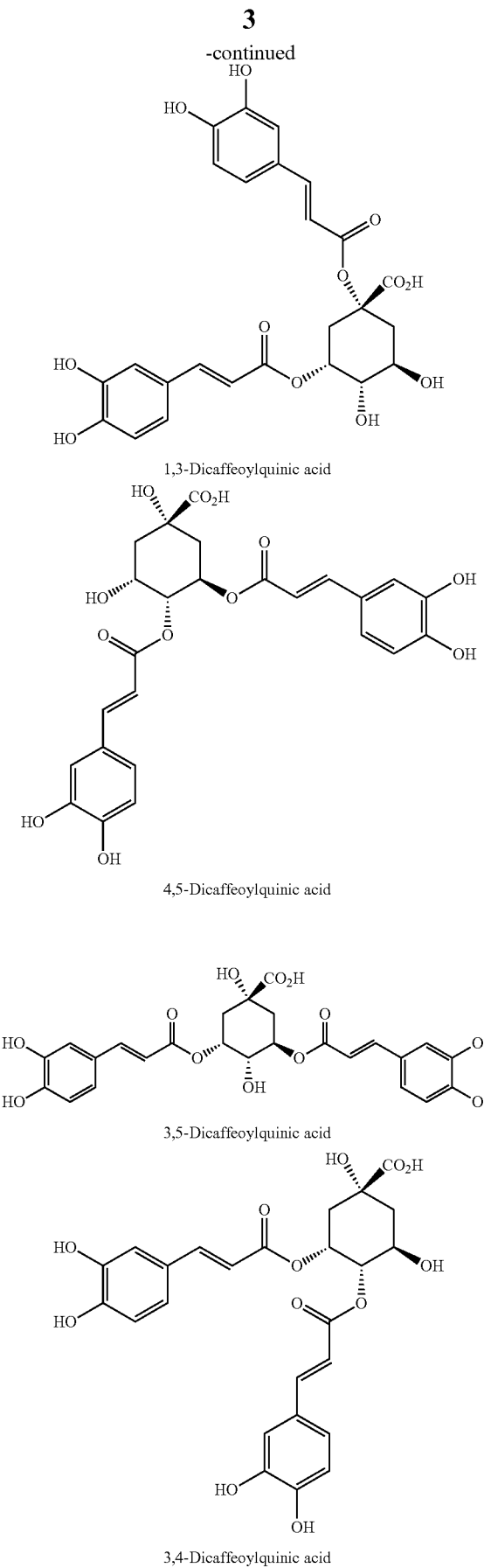

1,3-Dicaffeoylquinic acid 4,5-Dicaffeoylquinic acid 3,5-Dicaffeoylquinic acid 3,4-Dicaffeoylquinic acid

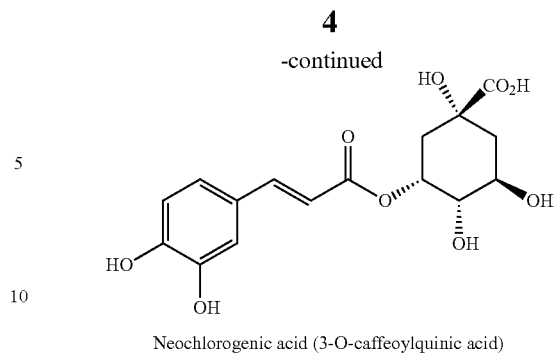

Neochlorogenic acid (3-O-caffeoylquinic acid)

The compounds can each be isolated in high purity (e.g., greater than 50%, greater than 60%, greater than 70%, greater than 80%, greater than 90%, and greater than 99%; or a purity of from about 50% to about 99%; about 60% to about 90%; about 80% to about 95% or about 70% to about 99% or higher). In addition, the methods described herein provide the ability to isolate the compounds of interest such that compositions comprising at least one of monocaffeoylquinic acids and dicaffeoylquinic acids, and salts thereof, obtained by the methods described herein can comprise substantially the same amounts by weight and/or substantially the same ratios by weight of monocaffeoylquinic acids, and dicaffeoylquinic acids, and salts thereof relative to the botanical biomass from which they are isolated.

DESCRIPTION OF THE DRAWINGS

The drawings illustrate generally, by way of example, but not by way of limitation, various embodiments discussed herein.

FIGS. 8-10 are tables showing, in tabular form, the peak name, retention time, and relative area percent data for the UHPLC-UV chromatographs shown in FIGS. 5-7, respectively. FIG. 8 is a table of the data for an initial yerba mate extract. The sum of target compounds is 49.7% purity by UV absorbance at 210 nm. FIG. 9 is a table of the data for a concentrate obtained following chromatographing the adjusted second initial extract on an ion exchange chromatography stationary phase. The sum of target compounds is 87.1% purity by UV absorbance at 210 nm. FIG. 10 is the data after drying, following the process described in steps (a)-(h), described herein, where "DCQA" refers to "dicaffeoylquinic acid." The sum of target compounds is 93.2% purity by UV absorbance at 210 nm.

Figure 1:
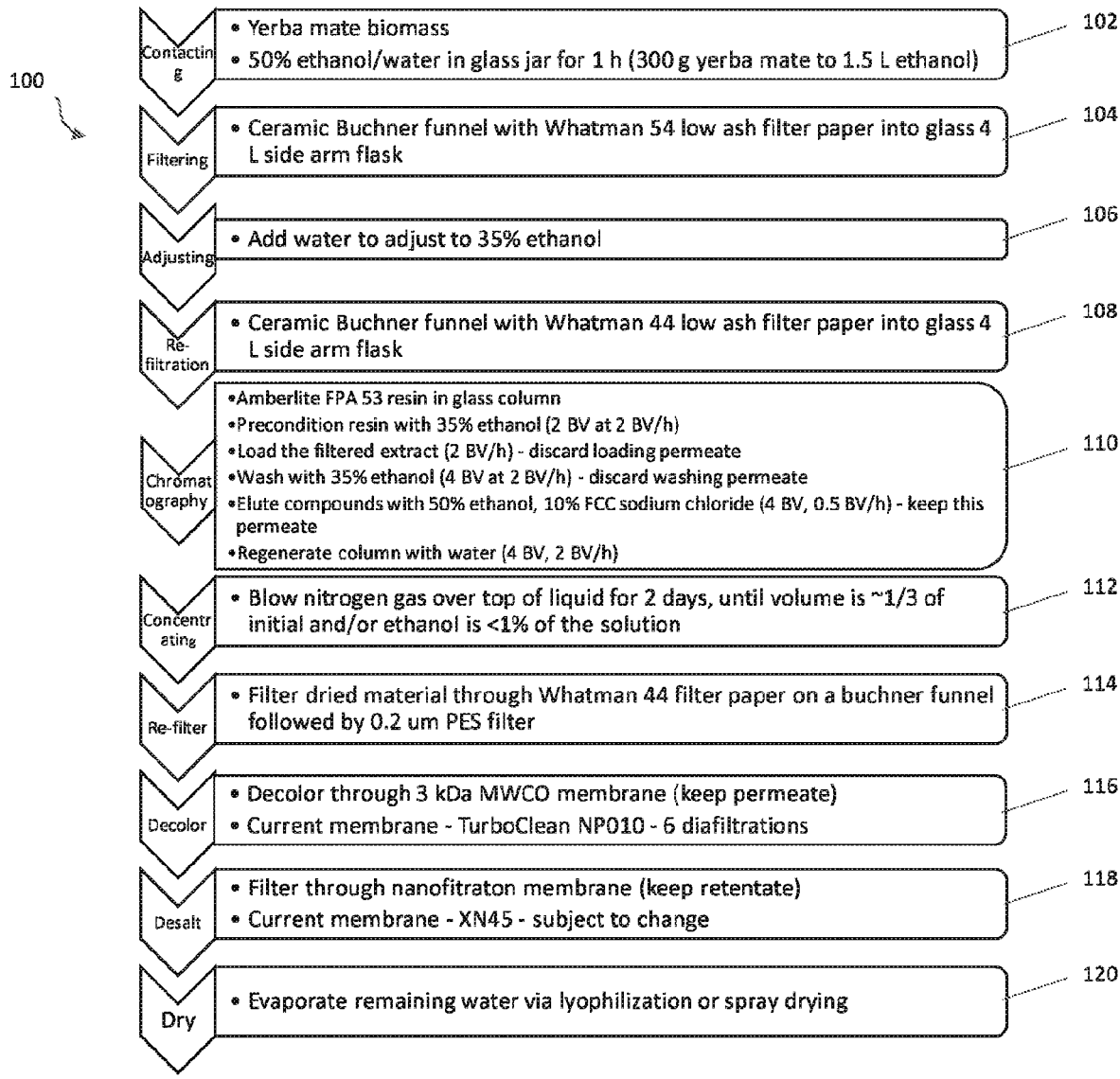
FIG. 1 is a flow diagram of an example of a method for making a composition comprising at least one of monocaffeoylquinic acids, and dicaffeoylquinic acids, and salts thereof.
Figure 2:
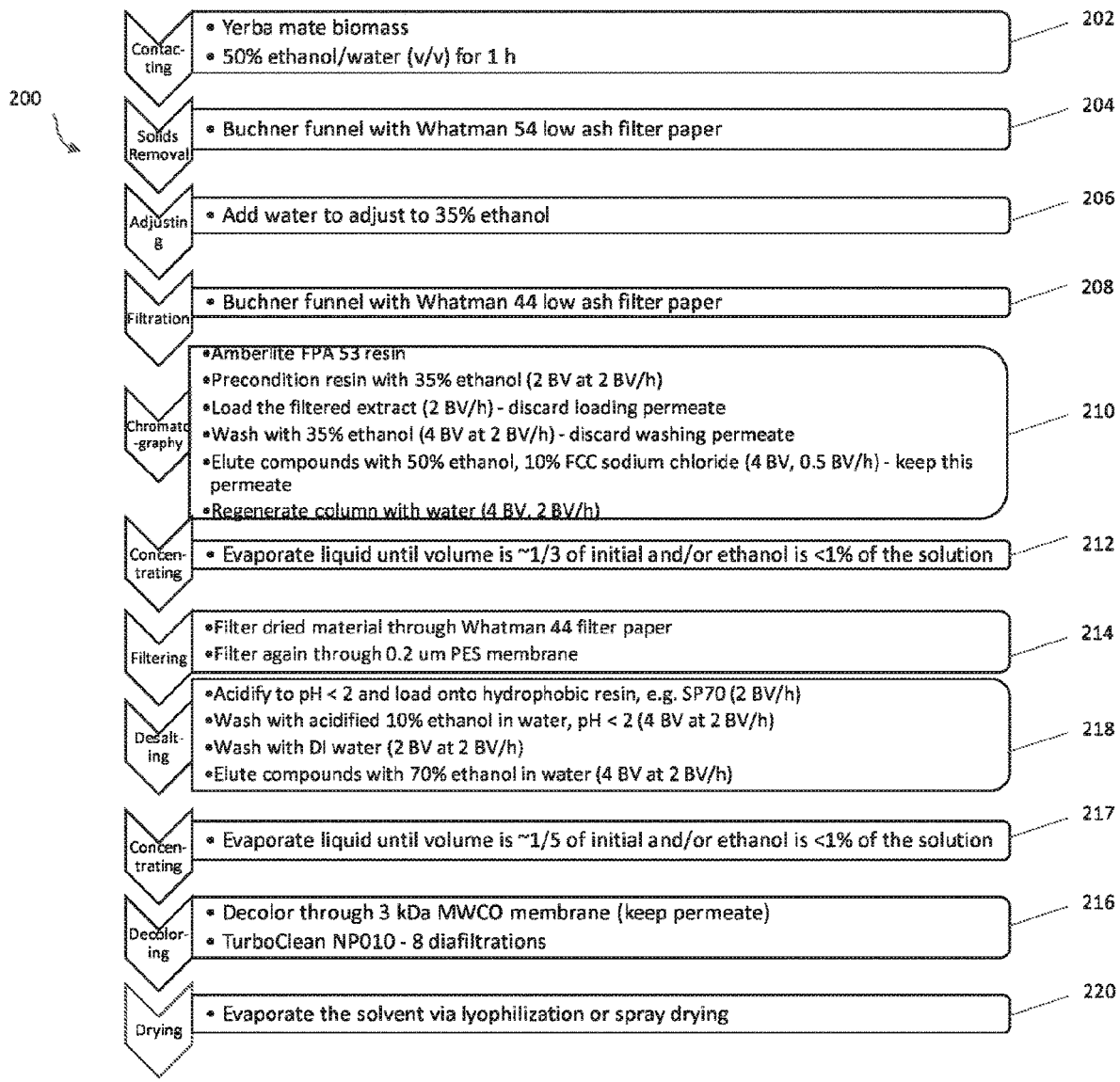
FIG. 2 is a flow diagram of another example of a method for making a composition comprising at least one of monocaffeoylquinic acids, and dicaffeoylquinic acids, and salts thereof.
Figure 3:
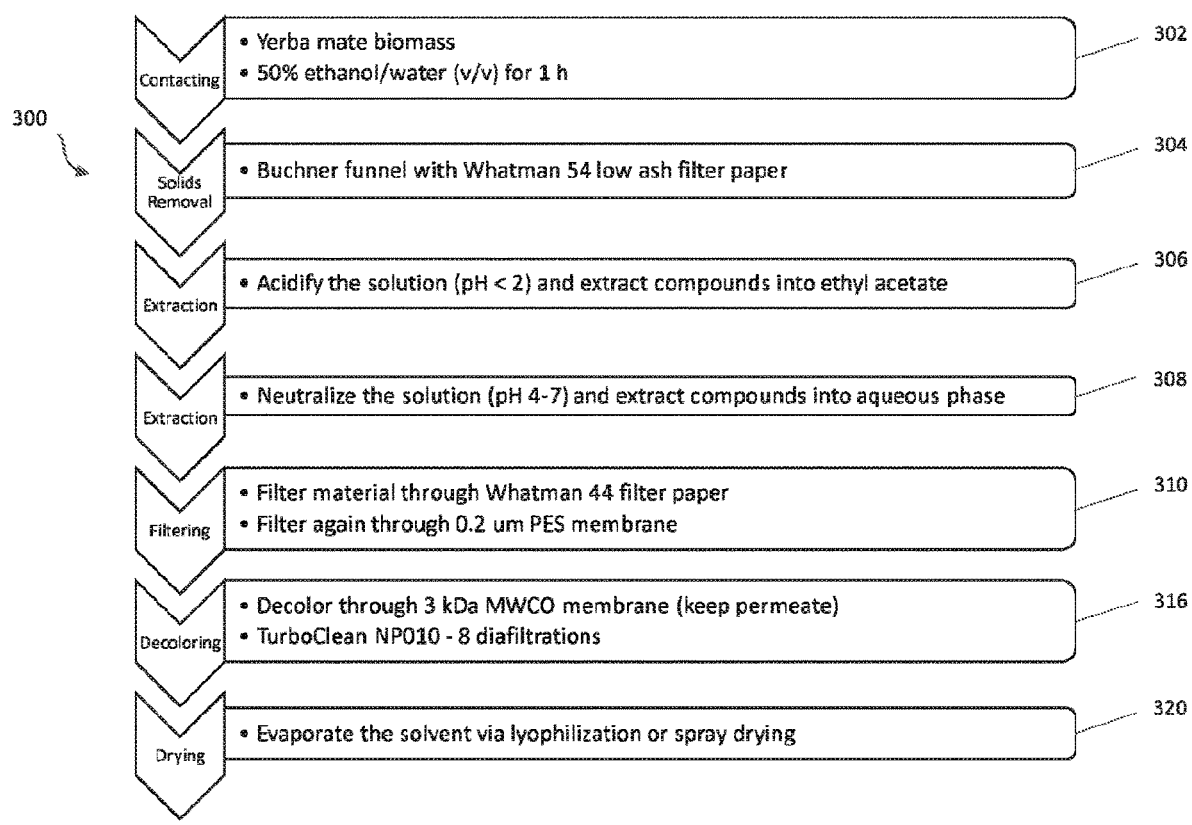
FIG. 3 is a flow diagram of an example of a method for making a composition comprising at least one of monocaffeoylquinic acids, and dicaffeoylquinic acids, and salts thereof.

Repeated use of reference characters in the specification and drawings is intended to represent the same or analogous features or elements of the disclosure, even when the numbers increase by 100 from figure-to-figure (e.g., drying operation 120 in FIG. 1 is analogous to or the same as drying operations 220, 320, and 420 in FIGS. 2-4, respectively). It should be understood that numerous other modifications and examples can be devised by those skilled in the art, which fall within the scope and spirit of the principles of the disclosure.

DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The disclosure relates generally to methods of making compositions comprising at least one of monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid), and salts thereof from botanical biomass. Because the monocaffeoylquinic acids and dicaffeoylquinic acids can be considered weak acids, they can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the monocaffeoylquinic acids, and dicaffeoylquinic acids will depend on various factors, including the pKa of each compound and the pH of the composition.

Examples of salts of monocaffeoylquinic acids, and dicaffeoylquinic acids include, but are not limited to, quaternary ammonium, sodium, potassium, lithium, magnesium, and calcium salts of caffeic acid, monocaffeoylquinic acids, and dicaffeoylquinic acids, and the like.

Exemplary Botanical Sources of Compositions Comprising Monocaffeoylquinic Acids Dicaffeoylquinic Acids and Salts Thereof Compositions comprising monocaffeoylquinic acids, dicaffeoylquinic acids and salts thereof may be prepared and/or isolated from botanical sources including but not limited to plants, e.g., plant leaves and stems. Table 1 provides genera of plants that are examples of botanical sources likely to contain monocaffeoylquinic acids, dicaffeoylquinic acids and salts thereof and that can be employed as biomass to prepare compositions comprising monocaffeoylquinic acids, dicaffeoylquinic acids and salts thereof.

TABLE 1

| Genus | Exemplary species and synonymous species (Syn.) | Exemplary common names |
| --- | --- | --- |
| Stevia | rebaudiana | Stevia |
| Siraitia | grosvenorii | Monkfruit |
| Coffea | C. arabica, C. canephora, C. ambongensis, C. boinensis, C. labatii, C. pterocarpa, C. bissetiae, C. namorokensis, C. charrieriana, C. anthonyi | Coffee, Coffee beans, Green coffee beans |
| Camellia | C. sinensis, C. japonica, C. sasanqua, C. oleifera, C. crapnelliana, C. reticulata, C. cuspidata, C. saluenensis, Camellia × williamsii, C. taliensis, C. rusticana | Tea, White tea, Yellow tea, Green tea, Oolong tea, Black tea, Red tea, Post-fermented tea |
| Phyllostachys | P. edulis, Syn. Bambos moosoo, Syn. Bambusa heterocycle, Syn. Bambusa mitis, Syn. Bambusa pubescens, P. bicolor, P. heterocycla, P. pubescens | Bamboo, moso bamboo, tortoise-shell bamboo, mao zhu |
| Calluna | C. vulgaris | common heather, ling, heather |
| Helianthus | H. annuus, H. tuberosus, H. verticillatus, H. giganteus, H. petiolaris, | Sunflower, Sunflower seeds |
| Vaccinium | V. corymbosum, V. alaskaense, V. angustifolium, V. crassifolium, V. boreale, V. darrowii, V. koreanum, V. myrtillus, V. uliginosum, V. macrocarpon, V. oxycoccos, V. ovatum, V. uliginosum, V. vitis-idaea | Blueberries, cranberries, bilberries, grouseberries, whortleberry, lingonberry, cowberry, huckleberry |

TABLE 1-continued

| Genus | Exemplary species and synonymous species (Syn.) | Exemplary common names |
|---|---|---|
| Vitis | Vitis vinifera | Grapes, Wine, Raisins |
| Cichorium | Cichorium intybus | Chicory |
| Echinacea | E. purpurea, E. angustifolia | Eastern purple coneflower, Echinacea |
| Parietaria | Parietaria officinalis | Eastern pellitory-of-the-wall, Upright pellitory, Lichwort |
| Chelidonium | Chelidonium majus | Greater celandine, Tetterwort, Nipplewort, Swallowwort |
| Sanguinaria | Sanguinaria canadensis | Bloodroot |
| Urtica | Urtica dioica | Common nettle, Stinging nettle |
| Solanum | S. tuberosum, S. stenotomum, S. phureja, S. goniocalyx, S. ajanhuiri, S. chaucha, S. juzepczukii, S. melongena, S. lycopersicum, S. incanum, Syn. Lycopersicon esculentum | Potato, Potato leaves, Eggplant, Aubergine, Tomato, Cherry tomato, Bitter apple, Thorn apple |
| Ipomoea | Ipomoea batatas | Sweet potato |
| Malus | Malus pumila, Malus domestica | Apple, Apple juice |
| Prunus | P. persica, P. dulcis, P. amygdalus, P. avium, P. cerasus, P. domestica, P. salicina | Peach, Nectarine, Cherry, Sour cherry, Wild cherry, Apricot, Almond, Plum, Prune |
| Ilex | I. paraguariensis, I. guayusa, I. kudingcha, I. vomitoria, I. aquifolium, I. latifolia, I. opaca | Holly, Yerba mate, Mate, Guayusa, Yaupon Holly, Kuding |
| Paullinia | Paullinia cupana | Guarana |
| Theobroma | Theobroma cacao | Cocoa, Cocoa bean, Cacao, Cacao bean |
| Cola | C. acuminata, C. Cola nitida, C. elegans, C. reticulate, C. nigerica, C. umbratilis | Kola nut, Kola tree, Cola nut, Cola tree |
| Matteuccia | M. struthiopteris, M. orientalis, M. intermedia, | Ostrich fern, Oriental ostrich fern, Fiddlehead fern, Shuttlecock fern |
| Pentarhizidium | Pentarhizidium orientalis | Oriental ostrich fern |
| Osmunda | Osmunda japonica, Osmunda regalis | Asian royal fern, Royal fern |
| Pteridium | Pteridium aquilinum | Bracken, Brake, Common bracken, Eagle fern, Eastern brakenfern |
| Syzygium | Syzygium aromaticum | Clove |
| Cinnamomum | C. verum, C. cassia, C. tamala | Cinnamon, Indian bay leaf |
| Myristica | M. fragrans, M. argentea, M. malabarica | Nutmeg |
| Laurus | Laurus nobilis | Bay laurel, Bay leaf |
| Ocimum | Ocimum basilicum | Basil, Great basil, Saint-Joseph's-wort |
| Thymus | Thymus vulgaris | Thyme |
| Salvia | Salvia officinalis | Sage, Garden sage, Common sage, Culinary sage |
| Rosmarinus | Rosmarinus officinalis | Rosemary |
| Origanum | O. vulgare, O. majorana, Syn. Majorana hortensis, Syn. Majorana majorana, O. onites, O. pulchellum | Oregano, Wild marjoram, Marjoram, Sweet marjoram, Knotted marjoram, Pot marjoram |
| Anethum | Anethum graveolens | Dill |
| Pimpinella | Pimpinella anisum | Anise |
| Illicium | Illicium verum | Star anise |
| Foeniculum | Foeniculum vulgare | Fennel, Florence fennel |
| Artemisia | Artemisia dracunculus, Artemisia vulgaris | Tarragon, Estragon, Mugwort |
| Glycyrrhiza | Glycyrrhiza glabra | Licorice, Liquorice |
| Glycine | Glycine max | Soy, Soybean, Soyabean, Soya bean |
| Triticum | Triticum aestivum, | Wheat, Common wheat |
| Oryza | Oryza sativa, Oryza glaberrima | Rice |
| Brassica | B. napus, B. rapa, B. campestres, B. juncea, B. oleracea | Canola, Broccoli, Cauliflower, Cabbage, Bok choy, Kale, Collard greens, Brussels sprouts, Kohlrabi |
| Drimys | Drimys winteri | Winter's bark |
| Sambucus | Sambucus nigra | Elderflower |
| Boehmeria | Boehmeria caudata | Assa-Peixe |
| Cynara | Cynara scolymus | Artichoke |
| Arctium | Arctium lappa | Greater burdock |
| Valeriana | Valeriana officinalis | Valerian |
| Matricaria | Matricaria chamomilla | Chamomile |
| Strychnos | Strychnos nux-vomica | strychnine tree, nux vomica, poison nut, semen strychnos, quaker buttons |

In some aspects, compositions comprising monocaffeoylquinic acids, dicaffeoylquinic acids and salts thereof may be isolated from botanical sources, such as those set forth in Table 1. Examples of commercially useful botanical sources from compositions comprising monocaffeoylquinic acids, dicaffeoylquinic acids and salts thereof may be isolated include yerba mate (*Ilex paraguariensis*), Stevia, coffee, tea, chicory, and globe artichoke. Some botanical sources may produce compositions comprising monocaffeoylquinic acids, dicaffeoylquinic acids and salts thereof that is enriched for one or more of monocaffeoylquinic acids and dicaffeoylquinic acids. For example, compositions comprising monocaffeoylquinic acids, dicaffeoylquinic acids and salts thereof isolated from yerba mate plant may be enriched for dicaffeoylquinic acids. In other aspects, compositions comprising monocaffeoylquinic acids, dicaffeoylquinic acids and salts thereof isolated from yerba mate plant that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

An example of a method for making a composition comprising at least one of monocaffeoylquinic acids and dicaffeoylquinic acids, and salts thereof, the method comprising (a) contacting yerba mate biomass with an aqueous composition to obtain an initial extract;

(b) removing solids from the initial extract to obtain a second initial extract;

(c) adjusting the volume of the second initial extract with an aqueous composition to obtain an adjusted second initial extract;

(d) chromatographing the adjusted second initial extract on an ion exchange chromatography stationary phase;

(e) eluting the ion exchange chromatography stationary phase to obtain a first eluent comprising a solvent;

(f) removing the solvent to form a concentrate; and (g) at least one of decoloring and desalting the concentrate to at least one of a filtrate and a retentate.

An example of a method for making a composition comprising at least one of monocaffeoylquinic acids, and dicaffeoylquinic acids, and salts thereof, the method comprising (a) contacting yerba mate biomass with an aqueous composition to obtain an initial extract;

(b) removing solids from the initial extract to obtain a second initial extract;

(c) adjusting the volume of the second initial extract with an aqueous composition to obtain an adjusted second initial extract;

(d) chromatographing the adjusted initial extract on an ion exchange chromatography stationary phase;

(e) eluting the ion exchange stationary phase to obtain a first eluent comprising a solvent;

(f) removing the solvent to form a concentrate;

(g) at least one of decoloring and desalting the concentrate to obtain at least one of a filtrate and a retentate; and (h) drying the at least one of a filtrate and a retentate to obtain the composition comprising at least one of caffeic acid, monocaffeoylquinic acids, and dicaffeoylquinic acids, and salts thereof.

Step (a) of the methods described herein involve contacting yerba mate biomass with an aqueous composition to obtain an initial extract comprising at least one of monocaffeoylquinic acids and dicaffeoylquinic acids, and salts thereof (e.g., quaternary ammonium, sodium, potassium, lithium, magnesium, and calcium salts).

The aqueous composition can comprise water and not contain any co-solvents, such as organic solvents. But the aqueous composition can comprise co-solvents, in addition to water. Suitable co-solvents include organic solvents, such as, (C1-C4)alkanols and mixtures of (C1-C4)alkanols. By "(C1-C4)alkanol" is meant an alcohol of the formula (C1-C4)alkyl-OH, wherein "alkyl" refers to straight chain and branched alkyl groups having from 1 to 4 carbon atoms such as methyl, ethyl, n-propyl, n-butyl, isopropyl, iso-butyl, sec-butyl, and t-butyl, such that the resulting (C1-C4)alkanol is methanol, ethanol, n-propanol, n-butanol, isopropanol, iso-butanol, sec-butanol, and t-butanol. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60%, up to about 70%, up to about 80%, up to about 90% or up to 100% by volume organic solvent the balance being water, except when the aqueous composition comprises 100% by volume organic solvent; or from about 30% to about 100%, about 50% to about 100%, about 60% to about 90%, about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively, pure water made basic to pH 7-11 with hydroxide, such as with sodium or potassium hydroxide, can be useful in the aqueous composition, with or without a co-solvent. In still other instances, it may be suitable to add a suitable non-ionic solute that can help balance the osmotic potential of the aqueous composition.

As used herein, the term "yerba mate biomass" generally refers to any and all parts of the yerba mate plant, such as *Ilex paraguariensis*, including the yerba mate plant leaves, stalks, stems, tops, roots, and the like. The yerba mate biomass can be in any suitable form including in comminuted form resulting from, e.g., from chopping the yerba mate biomass prior to and/or during the contacting with the aqueous composition. For example, the yerba mate biomass can be comminuted in a suitable container and the aqueous composition can be added to the comminuted yerba mate biomass, thus "contacting" the yerba mate biomass. The comminuted yerba mate biomass can then be optionally further comminuted within the suitable container. Or the yerba mate biomass can be placed in a suitable container, to which the aqueous composition is added, thus "contacting" the yerba mate biomass, and the resulting composition can be comminuted.

The yerba mate biomass can be stirred, sonicated or otherwise agitated prior to and/or during the contacting to, among other things, maximize the extraction of the at least one of caffeic acid, monocaffeoylquinic acids, and dicaffeoylquinic acids, and salts thereof.

The initial extract can be carried through to step (c) as-is or bulk solids and or plant solids present, such as comminuted yerba mate plant leaves, stalks, tops, roots, and the like, can be removed in step (b) of the methods described herein. When step (b) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of caffeic acid, monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Step (c) of the methods described herein involves adjusting the volume of the initial extract or second initial extract with a first aqueous composition or a second aqueous composition, respectively, to obtain an adjusted initial extract or adjusted second initial extract. The first and second aqueous compositions can be different or the same. The adjusted initial extract or adjusted second initial extract can be filtered at this point or can be carried through to step (d) as-is. The initial extract or the second initial extract can be filtered using any suitable filtration method, including gravity filtration or vacuum filtration through any suitable filter, so long as the filter does not substantially retain the at least one of monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

The volume of the initial extract or second initial extract can be adjusted with a sufficient amount of an aqueous composition (e.g., water) to obtain an adjusted initial extract or adjusted second initial extract to, among other things, increase the binding of the at least one of monocaffeoylquinic acids, and dicaffeoylquinic acids, and salts thereof, to the ion exchange chromatography column used in step (d) of the methods described herein, relative to an unadjusted initial extract or an unadjusted second initial extract.

The volume of the initial extract or second initial extract can be adjusted to, among other things, adjust the amount of organic solvent, when present, in the initial extract or second initial extract. The volume of the initial extract or second initial extract can be adjusted such that the adjusted initial extract or adjusted second initial extract comprises less than about 60%, less than about 50%, less than about 40%, less than about 30%, less than about 20%, less than about 10%, less than about 5%, less than about 1% or even about 0% by volume organic solvent, the balance being water; or from about 0% to about 40%, about 0% to about 30%, about 10% to about 40%, about 10% to about 30%, about 20% to about 40%, about 30% to about 40%, or about 35% by volume organic solvent, the balance being water.

Step (d) of the methods described herein involves chromatographing the adjusted initial extract or the second initial extract on an ion exchange stationary phase (e.g., a weak anion exchange stationary phase). The chromatographing can be performed in any suitable fashion, including in batch mode or using a column. The chromatographing can be performed with an aqueous composition (e.g., an aqueous composition comprising a (C1-C4)alkanol) as eluent (e.g., an aqueous composition comprising from about 0% to about 40%, about 0% to about 30%, about 10% to about 40%, about 10% to about 30%, about 20% to about 40%, about 30% to about 40%, or about 35% by volume (C1-C4) alkanol, the balance being water), leaving the at least one of caffeic acid, monocaffeoylquinic acids, and dicaffeoylquinic acids, and salts thereof, adsorbed on the weak ion exchange chromatography column, while eluting other compounds including caffeine, quercitrin, hyperoside, astragalin, avicularin, sophoricoside, and rutin (also known as rutoside, quercetin-3-O-rutinoside, and sophorin)

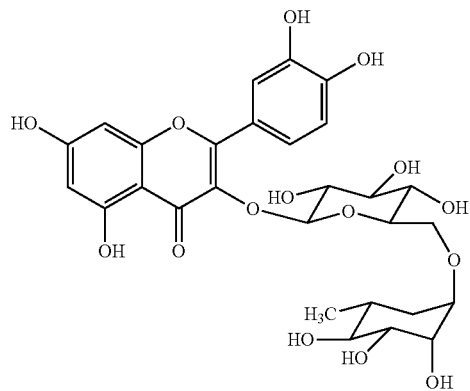 [SMILES: CC1CC(OCC2OC(Oc3c(-c4ccc(O)c(O)c4)oc4cc(O)cc(O)c4c3=O)C(O)C(O)C2O)C(O)C(O)C1O]

and isomers thereof. Step (d) of the methods described herein can decrease the concentration of at least one of caffeine, quercitrin, hyperoside, astragalin, avicularin, sophoricoside, rutin, and rutin isomers to a concentration of less than 1%, less than 0.5%, less than 0.1%, less than 0.05%, less than 0.01% or less than 0.001% by mass. The instant disclosure therefore contemplates yerba mate extracts comprising less than 0.1% of at least one of caffeine, quercitrin, hyperoside, astragalin, avicularin, sophoricoside, rutin, and rutin isomers by mass. The instant disclosure also contemplates yerba mate extracts comprising less than 0.5% by mass of each one of caffeine, quercitrin, hyperoside, astragalin, avicularin, sophoricoside, rutin, and rutin isomers and a less than about 1% by mass of caffeine, quercitrin, hyperoside, astragalin, avicularin, sophoricoside, rutin, and rutin isomers combined. The instant disclosure also contemplates yerba mate extracts that are effectively free of at least one of caffeine, quercitrin, hyperoside, astragalin, avicularin, sophoricoside, rutin, and rutin isomers (e.g., free of caffeine, free of quercitrin, free of hyperoside, free of astragalin, free of avicularin, free of sophoricoside, free of rutin, free of rutin isomers, and/or free of caffeine, rutin, and rutin isomers).

The ion exchange stationary phase is non-limiting and can be any suitable ion exchange chromatography stationary phase. Examples of suitable ion exchange chromatography stationary phases include ANX-SEPHAROSE® fast flow resin, DEAE SEPHAROSE®, DEAE SEPHADEX® A25 resin, AMBERLITE® (FPA 53; FPA 55; CG-50 Type I; IRC-50; IRC-50S; and IRP-64), DIAION WA10, and DOWEX® CCR-3.

The ion exchange chromatography stationary phase can optionally be pre-conditioned with an aqueous composition (e.g., an aqueous composition comprising a (C1-C4)alkanol), such as an aqueous composition comprising from about 0% to about 40%, about 0% to about 30%, about 10% to about 40%, about 10% to about 30%, about 20% to about 40%, about 30% to about 40%, or about 35% by volume (C1-C4)alkanol, the balance being water, prior to the chromatographing of the adjusted initial extract or adjusted second initial extract. For example, the weak ion exchange chromatography column can be pre-conditioned with about 2 or more bed volumes (BV) at a flow rate of about 2 BV/h.

The pH of the weak ion exchange chromatography column can optionally be adjusted prior to the chromatographing of the adjusted initial extract or adjusted second initial extract. For example, the pH of the weak ion exchange chromatography column can be adjusted prior to the chromatographing with any suitable acid (e.g., hydrochloric acid) such that the pH of the weak ion exchange chromatography column (e.g., the pH of the resin/stationary phase) is a pH of less than about 10, about 9 or less, about 8 or less, about 7 or less, about 6 or less, about 5 or less, about 4 or less, about 3 or less; or a pH of about 2 to about 10, about 3 to about 8, about 5 to about 9, about 2 to about 6; about 3 to about 4; or about 3 to about 6. The pH of the weak ion exchange chromatography column can be adjusted before or after the column is optionally pre-conditioned with the aqueous composition comprising a (C1-C4) prior to the chromatographing of the adjusted initial extract or adjusted second initial extract.

After pre-conditioning and/or adjusting of the pH of the weak ion exchange chromatography column, the adjusted initial extract or adjusted second initial extract can be loaded onto the column at any suitable rate, such as at a rate of above 2 BV/h (bed volumes per hour). After loading the adjusted initial extract or adjusted second initial extract, the column can be washed with any suitable volume of an aqueous composition comprising a (C1-C4)alkanol (e.g., at least about 2 BV, at least about 3 BV or at least about 4 BV of an aqueous composition comprising from about 10% to about 40%, about 10% to about 30%, about 20% to about 40%, about 30% to about 40%, or about 35% by volume (C1-C4)alkanol, the balance being water) at any suitable rate, such as at a rate of about 2 BV/h. The volume of aqueous composition comprising a (C1-C4)alkanol can be discarded, as it will contain, among other things, caffeine, quercitrin, hyperoside, astragalin, avicularin, sophoricoside, rutin, and rutin isomers.

Step (e) of the methods described herein involves eluting the adsorbed at least one of monocaffeoylquinic acids, and dicaffeoylquinic acids, and salts thereof, from the weak ion exchange chromatography column to obtain a first eluent comprising the at least one of monocaffeoylquinic acids, and dicaffeoylquinic acids, and salts thereof. The eluting is performed under any conditions suitable to elute the at least one of monocaffeoylquinic acids, and dicaffeoylquinic acids, and salts thereof from the column.

An example of suitable conditions to elute the at least one of monocaffeoylquinic acids, and dicaffeoylquinic acids, and salts thereof from the column include eluting the column with any suitable volume of a solution comprising a salt (e.g., sodium chloride, potassium chloride, ammonium chloride, sodium sulfate, potassium sulfate, sodium phosphate, potassium phosphate, and the like). Examples of solutions comprising a salt include solutions comprising at least one salt (e.g., about 5 wt. % to about 25 wt. %, about 15 wt. % to about 20 wt. % or about 5 wt. % to about 10 wt. % of a salt) dissolved in an aqueous composition comprising a (C1-C4)alkanol (e.g., at least about 2 BV, at least about 3 BV or at least about 4 BV of an aqueous composition comprising from about 10% to about 60%, about 20% to about 50%, about 30% to about 55%, about 40% to about 60%, or about 50% by volume (C1-C4)alkanol).

Another example of suitable conditions to elute the at least one of monocaffeoylquinic acids, and dicaffeoylquinic acids, and salts thereof from the column include eluting the column with any suitable volume of a solution comprising an acid (e.g., hydrochloric acid, sulfuric acid, phosphoric acid, acetic acid, formic acid, and the like). Examples of solutions comprising an acid include solutions comprising hydrochloric acid and the like and optionally acids solutions comprising an aqueous composition comprising from about 10% to about 60%, about 20% to about 50%, about 30% to about 55%, about 40% to about 60%, or about 50% by volume (C1-C4)alkanol).

The first eluent comprising the at least one of monocaffeoylquinic acids, and dicaffeoylquinic acids, and salts thereof, collected from the eluting step is collected and can be subsequently concentrated by removing solvent (e.g., to remove water and (C1-C4)alkanol) by any suitable means to provide a concentrate comprising the at least one of caffeic acid, monocaffeoylquinic acids, and dicaffeoylquinic acids, and salts thereof. The solvent removal can be accomplished under an inert atmosphere (e.g., under a nitrogen gas atmosphere). While not wishing to be bound by any specific theory, it is believed that performing the solvent removal under an inert atmosphere can reduce the formation of highly colored polymeric substances that either natively exist in the yerba mate biomass or form at one or more of the steps described herein.

The first eluent comprising the at least one of monocaffeoylquinic acids, and dicaffeoylquinic acids, and salts thereof comprises a solvent. The solvent can be removed in a step (f) to dryness or it can be removed to a point where a volume of an aqueous composition comprising a (C1-C4) alkanol remains as a solvent (e.g., about 50%, about 40%, about 30% about 20%, about 10% or about 5% of an original, total volume of the eluent) to form a concentrate, though the ratio of components that make up the aqueous composition comprising a (C1-C4)alkanol may or may not be different from the ratio of components that made up the aqueous composition comprising a (C1-C4)alkanol that was used to elute the adsorbed at least one of caffeic acid, monocaffeoylquinic acids, and dicaffeoylquinic acids, and salts thereof. Alternatively, the solvent in the eluent comprising the at least one of caffeic acid, monocaffeoylquinic acids, and dicaffeoylquinic acids, and salts thereof, can be removed to a point where a volume of an aqueous composition comprising a (C1-C4)alkanol remains, wherein the aqueous composition comprising a (C1-C4)alkanol comprises less than about 10%, less than about 5%, less than about 2% or less than about 1% by volume (C1-C4)alkanol.

Suitable conditions for removing solvent from the eluent comprising the at least one of monocaffeoylquinic acids, and dicaffeoylquinic acids, and salts thereof, to form a concentrate comprising the at least one of caffeic acid, monocaffeoylquinic acids, and dicaffeoylquinic acids, and salts thereof include blowing an inert gas (e.g., nitrogen gas) over the surface of the eluent. The eluent can be heated while blowing the nitrogen gas or it can be at room temperature (e.g., 25° C.). Other conditions for removing the solvent in the eluent include applying a vacuum to the container containing the eluent. The vacuum can be applied with the eluent at room temperature or while heating the container. Yet other conditions for removing solvent in the eluent include passing the eluent through a wiped film evaporator or an agitated thin film evaporator.

The pH of the concentrate can be adjusted at this point to obtain a pH-adjusted concentrate, though adjusting the pH at this point is optional. For example, the pH of the concentrate can be adjusted to a pH where the at least one of caffeic acid, monocaffeoylquinic acids, and dicaffeoylquinic acids, and salts thereof are protected from degradation. Suitable pHs include pHs of less than about 6, less than about 5, less than about 4, less than about 3 or less than about 2; such as a pH of from about 2 to about 6, about 2 to about 5, about 2 to about 4, about 3 to about 5 or a pH of about 3.5. The pH of the concentrate can be adjusted by using any suitable acid or base. When an acid is used, the acid can be hydrochloric acid and the like.

The concentrate or the pH-adjusted concentrate can be taken on as-is in the methods described herein or the removing step (f) or they can be filtered. The concentrate or the pH-adjusted concentrate can be filtered using any suitable filter (e.g., low ash filter paper, such as Whatman 44 or 54 low ash filter paper), a nylon filter, a polyethersulfone filter, a glass fiber filter, a pad of diatomaceous earth, and the like. In some instances, the pH-adjusted concentrate can be filtered through a polymeric membrane, such as a polyethersulfone (PES) filter having, e.g., 0.2 m pore size, or a pleated (flat membrane, vacuum filtration) or a pleated PES membrane, depending on the volume of the concentrate or the pH-adjusted concentrate.

The concentrate comprising the at least one of monocaffeoylquinic acids, and dicaffeoylquinic acids, and salts thereof, whether it is pH-adjusted, filtered or both pH-adjusted and filtered, can be taken directly to drying step (h) or can be submitted for desalting/decoloring in step (g) (in either order, including desalting, followed by decoloring; decoloring, followed by desalting; desalting, but not decoloring; or desalting, but not decoloring) of a concentrate that can be highly colored. The desalting/decoloring can be accomplished under an inert atmosphere (e.g., under a nitrogen gas atmosphere). While not wishing to be bound by any specific theory, it is believed that performing the one or more steps under an inert atmosphere can reduce the formation of highly colored polymeric substances that either natively exist in the yerba mate biomass or form at one or more of the steps described herein.

The concentrate, whether it is pH-adjusted, filtered or both pH-adjusted and filtered, can be decolored by any suitable means, including ultrafiltration (e.g., filtering through a molecular weight cutoff membrane, size-exclusion chromatography or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the yerba mate biomass or form at one or more of the steps described herein.

The filtrate from decoloring can be taken on to drying step (h) or it can be desalted in step (g). Alternatively, the concentrate, whether it is pH-adjusted, filtered or both pH-adjusted and filtered, can be desalted without first decoloring. Regardless, the desalting can be accomplished using a nanofiltration membrane and a hydrophobic resin. Those of skill in the art would recognize that when one uses a nanofiltration membrane and a hydrophobic resin one discards the permeate and keeps the retentate. In one example, desalting can be accomplished using a hydrophobic resin (e.g., a porous poly divinylbenzene/ethylvinylbenzene matrix, such as SEPABEADS™ SP70), where one would load a pH-adjusted concentrate (e.g., an acidified concentrate, with a pH of less than about 2) comprising less than about 20% by volume (C1-C4)alkanol. The resin is then washed with dilute alcohol (e.g., less than about 10% by volume (C1-C4)alkanol, the rest being water having a pH of less than about 2) and then eluted with an aqueous composition comprising about 70% by volume (C1-C4)alkanol in water to obtain a desalted second eluent comprising the at least one of monocaffeoylquinic acids, and dicaffeoylquinic acids, and salts thereof.

If desalting precedes decoloring in step (g), the solvent in the permeate from the desalting step can be removed to a point where a volume of an aqueous composition comprising a (C1-C4)alkanol remains as a solvent (e.g., about 50%, about 40%, about 30% about 20%, about 10% or about 5% of an original, total volume of the eluent) to form a first desalted concentrate. Alternatively, the solvent in the permeate from the desalting can be removed, to give a second desalted concentrate, to a point where a volume of an aqueous composition comprising a (C1-C4)alkanol remains, wherein the aqueous composition comprising a (C1-C4) alkanol comprises less than about 10%, less than about 5%, less than about 2% or less than about 1% by volume (C1-C4)alkanol. The first desalted concentrate can also have the attributes of the second desalted concentrate, such that the first desalted concentrate also has less than about 10%, less than about 5%, less than about 2% or less than about 1% by volume (C1-C4)alkanol.

Suitable conditions for removing solvent from the permeate comprising the at least one of monocaffeoylquinic acids, and dicaffeoylquinic acids, and salts thereof, to form a first/second desalted concentrate comprising the at least one of caffeic acid, monocaffeoylquinic acids, and dicaffeoylquinic acids, and salts thereof include blowing an inert gas (e.g., nitrogen gas) over the surface of the eluent. The permeate can be heated while blowing the nitrogen gas or it can be at room temperature (e.g., 25° C.). Other conditions for removing the solvent in the eluent include applying a vacuum to the container containing the permeate. The vacuum can be applied with the permeate at room temperature or while heating the container. Yet other conditions for removing solvent in the permeate include passing the permeate through a wiped film evaporator or an agitated thin film evaporator.

In another example, the concentrate comprising the at least one of monocaffeoylquinic acids, and dicaffeoylquinic acids, and salts thereof can be filtered through filter paper to obtain a first filtrate, the first filtrate is ultrafiltered to obtain a second filtrate, and the second filtrate is nanofiltered using a nanofiltration membrane to obtain a first retentate or the second filtrate is eluted through a hydrophobic resin to obtain a desalted second eluent. In another example, the concentrate comprising the at least one of monocaffeoylquinic acids, and dicaffeoylquinic acids, and salts thereof can be filtered through filter paper to obtain a first filtrate, the first filtrate is nanofiltered using a nanofiltration membrane to obtain a third retentate or the first filtrate is eluted through a hydrophobic resin to obtain a desalted second eluent, and the third retentate or the desalted second eluent is ultrafiltered to obtain a third filtrate.

As mentioned herein, the eluent comprising the at least one of monocaffeoylquinic acids, and dicaffeoylquinic acids, and salts thereof, can be concentrated to dryness or it can be concentrated to a point where a volume of an aqueous composition comprising a (C1-C4)alkanol remains. If the eluent is concentrated to dryness, the dry material can be reconstituted using, for example, an aqueous composition comprising a (C1-C4)alkanol. The reconstituted material can then be filtered as described herein, to among other things, at least one of desalt and decolor.

The methods described herein can include step (h) that involves drying first retentate, desalted second eluent or the third filtrate to obtain the composition comprising the at least one of caffeic acid, monocaffeoylquinic acids, and dicaffeoylquinic acids, and salts thereof. The first retentate, desalted second eluent or the third filtrate can be dried in any suitable manner, including by lyophilization or spray drying.

FIGS. 1-4 set forth processes using yerba mate and *Stevia* as exemplary botanical sources. FIG. 1 is a flow diagram of a method 100 for making a composition comprising at least one of monocaffeoylquinic acids, and dicaffeoylquinic acids, and salts thereof. In operation 102, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 104, the initial extract is filtered using, for example, a ceramic Büchner funnel with Whatman 54 low ash filter paper into glass 4 L side arm flask. In operation 106, the volume of the filtered initial extract is adjusted with an aqueous composition, in this case water, to obtain an adjusted filtered initial extract containing a lower proportion of ethanol, in this case 35% by volume ethanol. In operation 108, the adjusted filtered initial extract can be re-filtered using, for example, a ceramic Büchner funnel with Whatman 44 low ash filter paper into glass 4 L side arm flask. In operation 110, the adjusted filtered initial extract is chromatographed on an ion exchange chromatography stationary phase. For example, AMBERLITE® FPA 53 resin is packed in glass column. The resin is preconditioned with 35% ethanol (2 BV at 2 BV/h). The adjusted filtered initial extract is loaded is loaded (2 BV/h) onto the resin, discarding the loading permeate. The resin is washed with 35% ethanol (4 BV at 2 BV/h) discarding the washing permeate. The at least one of caffeic acid, monocaffeoylquinic acids, and dicaffeoylquinic acids, and salts thereof are eluted with 50% ethanol/water, 10% FCC sodium chloride (4 BV, 0.5 BV/h) and the permeate is kept. The column/resin can optionally be regenerated with water (4 BV, 2 BV/h). In operation 112, the eluent/permeate is concentrated to form a concentrate. In this case, nitrogen gas was blown over the top of the eluent/permeate for 2 days, until volume the volume is approximately one third of the initial volume of eluent/permeate and/or ethanol is less than 1% in the eluent/permeate, thereby obtaining a concentrate. In operation 114, the concentrate is acidified to a pH of approximately 3.5 and then filtered through a Whatman 44 filter paper on a Büchner funnel followed by 0.2 m polyether sulfone (PES) filter. In operation 116, the filtered concentrate is decolored using a molecular weight cutoff membrane (MWCO; e.g., a MWCO membrane that removes materials having a molecular weight of greater than 10 kDA, such as a 3 kDa TURBOCLEAN® NP010) to, among other things, decolor the filtered concentrate and obtain a permeate. In operation 118, the permeate is filtered through a nanofiltration membrane (e.g., TRISEP® XN45 membrane) and the retentate is subsequently dried in operation 120 to obtain the composition comprising at least one of caffeic acid, monocaffeoylquinic acids, and dicaffeoylquinic acids, and salts thereof.

FIG. 2 is a flow diagram of a method 200 for making a composition comprising at least one of monocaffeoylquinic acids, and dicaffeoylquinic acids, and salts thereof. In operation 202, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 204, the initial extract is filtered using, for example, a ceramic Büchner funnel with Whatman 54 low ash filter paper into glass 4 L side arm flask. In operation 206, the volume of the filtered initial extract is adjusted with an aqueous composition, in this case water, to obtain an adjusted filtered initial extract containing a lower proportion of ethanol, in this case 35% by volume ethanol. In operation 208, the adjusted filtered initial extract can be re-filtered using, for example, a ceramic Büchner funnel with Whatman 44 low ash filter paper into glass 4 L side arm flask. In operation 210, the adjusted filtered initial extract is chromatographed on an ion exchange chromatography stationary phase. For example, AMBERLITE® FPA 53 resin is packed in glass column. The resin is preconditioned with 35% ethanol (2 BV at 2 BV/h). The adjusted filtered initial extract is loaded is loaded (2 BV/h) onto the resin, discarding the loading permeate. The resin is washed with 35% ethanol (4 BV at 2 BV/h) discarding the washing permeate. The at least one of caffeic acid, monocaffeoylquinic acids, and dicaffeoylquinic acids, and salts thereof are eluted with 50% ethanol/water, 10% FCC sodium chloride (4 BV, 0.5 BV/h) and the permeate is kept. The column/resin can optionally be regenerated with water (4 BV, 2 BV/h). In operation 212, the eluent/permeate is concentrated to form a concentrate, where the volume is approximately one third of the initial volume of eluent/permeate and/or ethanol is less than 1% in the eluent/permeate, thereby obtaining a concentrate. In operation 214, the concentrate is acidified to a pH of approximately 1 and then filtered through a Whatman 44 filter paper on a Büchner funnel followed by 0.2 m polyether sulfone (PES) filter. In operation 218, the concentrate is desalted using a hydrophobic resin (e.g., a porous poly divinylbenzene/ethylvinylbenzene matrix, such as SEPA-BEADS™ SP70) and the solvent in the retentate is removed in operation 217. In operation 216, the desalted concentrate is decolored using a molecular weight cutoff membrane (MWCO; e.g., a MWCO membrane that removes materials having a molecular weight of greater than 10 kDA, such as a 3 kDa TURBOCLEAN® NP010) to, among other things, decolor the filtered concentrate and obtain a permeate. subsequently dried in operation 220 to obtain the composition comprising at least one of caffeic acid, monocaffeoylquinic acids, and dicaffeoylquinic acids, and salts thereof.

Another example of a method for making a composition comprising at least one of monocaffeoylquinic acids, and dicaffeoylquinic acids, and salts thereof, the method comprising (i) contacting yerba mate biomass with an aqueous composition to obtain an initial extract;

(ii) removing solids from the initial extract to obtain a second initial extract;

(iii) contacting the second initial extract with acidified ethyl acetate to obtain an acidic ethyl acetate extract;

(iv) neutralizing the acidic ethyl acetate extract to obtain neutralized ethyl acetate and an aqueous extract;

(v) decoloring the aqueous extract to obtain a decolored aqueous extract; and (vi) drying the decolored aqueous extract to obtain the composition comprising at least one of monocaffeoylquinic acids, and dicaffeoylquinic acids, and salts thereof.

Steps (i), (ii), and (vi) are performed as described herein for steps (a), (b), and (h). Step (v) is analogous to filtering step (g), except that step (v) involves only decoloring processes, such as ultrafiltration, which includes filtering through a molecular weight cutoff membrane, size-exclusion chromatography, and gel permeation, as discussed herein. Accordingly, the disclosure with regard to steps (a), (b), (g), and (h) applies to steps (i), (ii), (v), and (vi).

Step (i) of the methods described herein involve contacting yerba mate biomass with an aqueous composition to obtain an initial extract comprising at least one of monocaffeoylquinic acids, and dicaffeoylquinic acids, and salts thereof.

The aqueous composition can comprise water and not contain any co-solvents, such as organic solvents. But the aqueous composition can comprise co-solvents, in addition to water. Suitable co-solvents include organic solvents, such as, (C1-C4)alkanols and mixtures of (C1-C4)alkanols. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60% by volume organic solvent, the balance being water; or from about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, phosphoric acid, sulfuric acid, nitric acid or the like can be useful in the aqueous composition, with or without a co-solvent. Alternatively, pure water made basic to pH 7-11 with hydroxide, such as sodium or potassium hydroxide can be useful in the aqueous composition, with or without a co-solvent. In still other instances, it may be suitable to add a suitable non-ionic solute that can help balance the osmotic potential of the aqueous composition.

The yerba mate biomass can be stirred, sonicated or otherwise agitated prior to and/or during the contacting of step (i) to, among other things, maximize the extraction of the at least one of caffeic acid, monocaffeoylquinic acids, and dicaffeoylquinic acids, and salts thereof.

The initial extract can be carried through to step (iii) as-is or bulk solids and or plant solids present, such as comminuted yerba mate plant leaves, stalks, tops, roots, and the like, can be removed in step (ii) of the methods described herein. When step (ii) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of caffeic acid, monocaffeoylquinic acids, and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Prior to carrying out step (iii) one can optionally adjust the pH of the initial or second initial extract with a suitable acid. (e.g., hydrochloric acid and the like) or suitable base (e.g., sodium hydroxide) to a pH of between about 4 and about 7. The pH-adjusted initial or second initial extract is then extracted with ethyl acetate that has not been pre-acidified as described herein. While not wishing to be bound by any specific theory, it is believed that when the pH of the initial or second initial extract is adjusted to between about 4 and about 7, it is possible to extract certain impurities into the ethyl acetate, while keeping compounds of interest (e.g., caffeic acid, monocaffeoylquinic acids, and dicaffeoylquinic acids, and salts thereof) in the aqueous layer.

Step (iii) of the methods described herein involves contacting the first or second initial extract with acidified ethyl acetate to obtain an acidic ethyl acetate extract. The acidified ethyl acetate can be prepared in any suitable manner, including by adding any suitable acid, including hydrochloric acid, sulfuric acid, and glacial acetic acid (e.g., 0.01-1% vol/vol). The acidic ethyl acetate extract is washed with water (e.g., three times, with 1:1 vol/vol water). Under these conditions, the at least one of caffeic acid, monocaffeoylquinic acids, and dicaffeoylquinic acids will substantially be in their conjugate acid form and will reside substantially in the acidic ethyl acetate layer that forms when the acidic ethyl acetate extract is washed with water. The water layers are discarded and the acidic ethyl acetate extract is carried on to step (iv).

Step (iii) of the methods described herein can be carried out in other suitable ways, including by using ethyl acetate that has not been pre-acidified as described herein (e.g., by pre-washing with glacial acetic acid), but instead by adjusting the pH of the initial or second initial extract with a suitable acid. (e.g., hydrochloric acid and the like), then extracting the pH-adjusted initial or second initial extract with ethyl acetate that has not been pre-acidified. Regardless of the acid used to adjust the pH of the initial extract or the second initial extract, the pH of the initial extract or the second initial extract is adjusted to about 4 or less, 3 or less, about 2 or less, or about 1 or less. The water layers are discarded and the acidic ethyl acetate extract that results is carried on to step (iv).

Step (iv) of the methods described herein involves neutralizing the acidic ethyl acetate extract to obtain neutralized ethyl acetate and an aqueous extract. This is accomplished in any suitable way, including washing the acidic ethyl acetate extract with water (e.g., three times, with 1:1 vol/vol water) comprising a suitable base, such as sodium hydroxide, potassium hydroxide, and the like, and combinations thereof. Under these conditions, the at least one of caffeic acid, monocaffeoylquinic acids, and dicaffeoylquinic acids will substantially be in their conjugate base form and will substantially reside in the water layer that forms when the acidic ethyl acetate extract is washed with water comprising a suitable base.

In an alternative, optional step to step (iv), step (iv-a), the acidic ethyl acetate extract that results from step (iii) can be optionally removed, even removed to dryness. Any solid that remains can either be reconstituted with pH neutral water (e.g., deionized water) and the pH of the water can then be adjusted to about 3 to about 7; or the solid that remains can be reconstituted with water having a pH of about 3 to about 7.

The aqueous extract comprising the at least one of caffeic acid, monocaffeoylquinic acids, and dicaffeoylquinic acids, and salts thereof, whether they emanate from step (iv) or step (iv-a), can then be submitted for step (v) to accomplish, among other things, decoloring of aqueous extract, which can be highly colored. Decoloring can be accomplished by any suitable means, including ultrafiltration (e.g., filtering through a molecular weight cutoff membrane, size-exclusion chromatography, or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the yerba mate biomass or form at one or more of the steps described herein.

Another example of modifications to the method described herein comprising steps (i)-(vi) (including the alternative, optional step (iv-a) includes a method for making a composition comprising at least one of monocaffeoylquinic acids, and dicaffeoylquinic acids, and salts thereof, the method comprising contacting yerba mate biomass with an aqueous composition to obtain an initial extract;

removing solids from the initial extract to obtain a second initial extract;

adjusting the pH of the second initial extract to a pH of from about 4 to about 7 to obtain a first pH-adjusted second initial extract;

contacting the first pH-adjusted second initial extract with ethyl acetate to obtain a first ethyl acetate extract and a second aqueous extract;

adjusting the pH of the second aqueous extract to a pH of less than 2 to obtain a pH-adjusted second aqueous extract;

contacting the pH-adjusted second aqueous extract with ethyl acetate to obtain a second ethyl acetate extract;

removing the ethyl acetate from the second ethyl acetate extract to obtain a purified composition;

reconstituting the crude composition with water to obtain a third aqueous extract; and decoloring the third aqueous extract to obtain a decolored aqueous extract.

The "purified composition" will comprise the compounds of interest (e.g., the at least one of monocaffeoylquinic acids, and dicaffeoylquinic acids, and salts thereof) and is purified relative to at least the initial extract and the second initial extract, in that the "purified composition" will not contain certain impurities in the initial extract and the second initial extract, but does contain highly colored polymeric substances that either natively exist in the yerba mate biomass or form at one or more of the steps described herein and that are removed in the decoloring step.

Yet another example of modifications to the method described herein comprising steps (i)-(vi) (including the alternative, optional step (iv-a) includes a method for making a composition comprising at least one of mono-caffeoylquinic acids, and dicaffeoylquinic acids, and salts thereof, the method comprising contacting yerba mate biomass with an aqueous composition to obtain an initial extract;

removing solids from the initial extract to obtain a second initial extract;

adjusting the pH of the second initial extract to a pH of less than about 2 to obtain a second pH-adjusted second initial extract;

contacting the second pH-adjusted second initial extract with ethyl acetate to obtain a third ethyl acetate extract;

neutralizing the third ethyl acetate extract to obtain a first neutralized ethyl acetate extract and a third aqueous extract; and decoloring the third aqueous extract to obtain a decolored aqueous extract.

The methods described herein can include step (vi) that involves drying the decolored aqueous extract to obtain the composition comprising the at least one of mono-caffeoylquinic acids, and dicaffeoylquinic acids, and salts thereof. The first or second retentates or the third filtrate can be dried in any suitable manner, including by lyophilization or spray drying.

FIG. 3 is a flow diagram of a method 300 for making a composition comprising at least one of monocaffeoylquinic acids, and dicaffeoylquinic acids, and salts thereof. In operation 302, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 304, the initial extract is filtered using, for example, a ceramic Büchner funnel with Whatman 54 low ash filter paper into glass 4 L side arm flask to, among other things, remove solids from, e.g., the yerba mate biomass. The filtrate from operation 304 is extracted in operation 306 with acidified ethyl acetate extraction. Following extraction of the at least one of caffeic acid, monocaffeoylquinic acids, and dicaffeoylquinic acids into the acidified ethyl acetate, the acidified ethyl acetate is washed with water comprising a suitable base, such as sodium hydroxide, potassium hydroxide, and the like, in operation 308 to obtain neutralized ethyl acetate and an aqueous extract. Under these conditions, the at least one of caffeic acid, monocaffeoylquinic acids, and dicaffeoylquinic acids will substantially be in their conjugate base form and will substantially reside in the water layer that forms when the acidic ethyl acetate extract is washed with water comprising a suitable base. In operation 310 the water layer is filtered to obtain a filtrate. In operation 316, the filtrate is decolored using a 3 kDa molecular weight cutoff membrane (TURBOCLEAN® NP010; six diafiltrations) to, among other things, decolor the aqueous extract, thereby obtaining a decolored aqueous extract. In operation 320, the decolored aqueous extract is dried to obtain the composition at least one of caffeic acid, monocaffeoylquinic acids, and dicaffeoylquinic acids, and salts thereof.

Figure 4A:
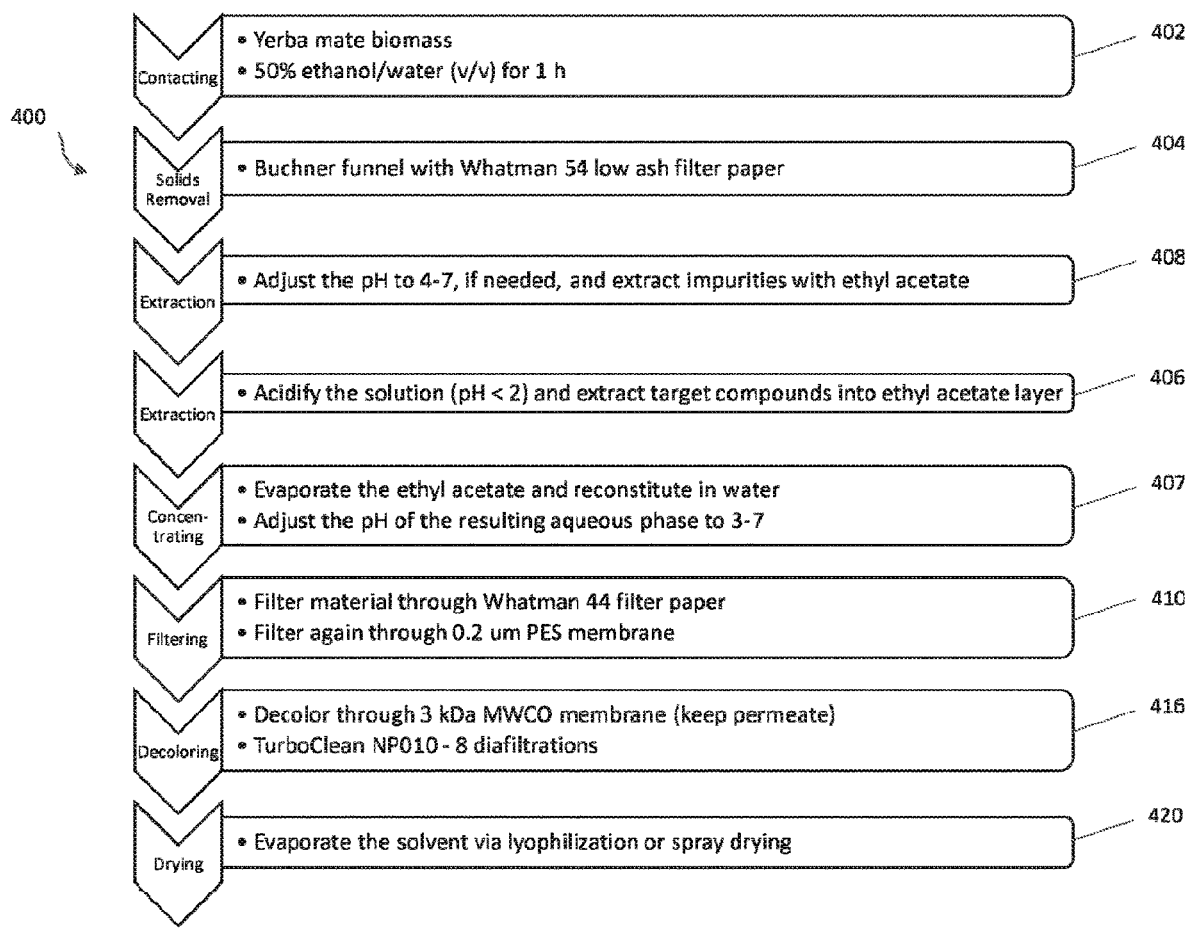
FIG. 4A is a flow diagram of another example of a method for making a composition comprising at least one of monocaffeoylquinic acids, and dicaffeoylquinic acids, and salts thereof.

FIG. 4A is a flow diagram of a method 400 for making a composition comprising at least one of monocaffeoylquinic acids, and dicaffeoylquinic acids, and salts thereof. In operation 402, yerba mate biomass is contacted with an aqueous composition containing 50% ethanol/water in a suitable container (e.g., a glass jar) for 1 h (300 g yerba mate biomass into 1.5 L solvent) to obtain an initial extract. In operation 404, the initial extract is filtered using, for example, a ceramic Büchner funnel with Whatman 54 low ash filter paper into glass 4 L side arm flask to, among other things, remove solids from, e.g., the yerba mate biomass. The filtrate from operation 404 is pH-adjusted to from about 4 to about 7 and the filtrate is extracted in operation 408 with ethyl acetate, while the compounds of interest remain in the aqueous layer. In operation 406, the pH of the aqueous layer is adjusted to less than 2 and the aqueous layer is extracted with ethyl acetate. Following extraction of the at least one of caffeic acid, monocaffeoylquinic acids, and dicaffeoylquinic acids into the ethyl acetate, the ethyl acetate is removed to dryness in operation 407 to obtain a solid. The solid is reconstituted with water and the pH of the water is adjusted to from about 3 to about 7. Under these conditions, the at least one of monocaffeoylquinic acids, and dicaffeoylquinic acids will substantially be in their conjugate base form and will dissolve in the water. In operation 410 the water layer is filtered to obtain a filtrate. In operation 416, the filtrate is decolored using a 3 kDa molecular weight cutoff membrane (TURBOCLEAN® NP010; six diafiltrations) to, among other things, decolor the aqueous extract, thereby obtaining a decolored aqueous extract. In operation 420, the decolored aqueous extract is dried to obtain the composition at least one of monocaffeoylquinic acids, and dicaffeoylquinic acids, and salts thereof.

An example of a method for making a composition comprising at least one of monocaffeoylquinic acids and dicaffeoylquinic acids, and salts thereof, the method comprising (AA) contacting botanical biomass with an aqueous composition to obtain an initial extract;

(BB) removing solids from the initial extract to obtain a second initial extract;

(CC) adjusting the volume of the second initial extract with an aqueous composition to obtain an adjusted second initial extract;

(DD) chromatographing the adjusted second initial extract on an ion exchange chromatography stationary phase;

(EE) eluting the ion exchange chromatography stationary phase to obtain a first eluent comprising a solvent;

(FF) removing the solvent to form a concentrate; and (GG) at least one of decoloring and desalting the concentrate to at least one of a filtrate and a retentate.

An example of a method for making a composition comprising at least one of monocaffeoylquinic acids and dicaffeoylquinic acids, and salts thereof, the method comprising (AA) contacting botanical biomass with an aqueous composition to obtain an initial extract;

(BB) removing solids from the initial extract to obtain a second initial extract;

(CC) adjusting the volume of the second initial extract with an aqueous composition to obtain an adjusted second initial extract;

(DD) chromatographing the adjusted initial extract on an ion exchange chromatography stationary phase;

(EE) eluting the ion exchange stationary phase to obtain a first eluent comprising a solvent;

(FF) removing the solvent to form a concentrate;

(GG) at least one of decoloring and desalting the concentrate to obtain at least one of a filtrate and a retentate; and (HH) drying the at least one of a filtrate and a retentate to obtain the composition comprising at least one of monocaffeoylquinic acids and dicaffeoylquinic acids, and salts thereof.

Step (AA) of the methods described herein involve contacting botanical biomass with an aqueous composition to obtain an initial extract comprising at least one of monocaffeoylquinic acids and dicaffeoylquinic acids, and salts thereof (e.g., quaternary ammonium, sodium, potassium, lithium, magnesium, and calcium salts).

The aqueous composition can comprise water and not contain any co-solvents, such as organic solvents. But the aqueous composition can comprise co-solvents, in addition to water. Suitable co-solvents include organic solvents, such as, (C1-C4)alkanols and mixtures of (C1-C4)alkanols. By "(C1-C4)alkanol" is meant an alcohol of the formula (C1-C4)alkyl-OH, wherein "alkyl" refers to straight chain and branched alkyl groups having from 1 to 4 carbon atoms such as methyl, ethyl, n-propyl, n-butyl, isopropyl, iso-butyl, sec-butyl, and t-butyl, such that the resulting (C1-C4)alkanol is methanol, ethanol, n-propanol, n-butanol, isopropanol, iso-butanol, sec-butanol, and t-butanol. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60%, up to about 70%, up to about 80%, up to about 90% or up to 100% by volume organic solvent the balance being water, except when the aqueous composition comprises 100% by volume organic solvent; or from about 30% to about 100%, about 50% to about 100%, about 60% to about 90%, about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively, pure water made basic to pH 7-11 with hydroxide, such as with sodium or potassium hydroxide, can be useful in the aqueous composition, with or without a co-solvent. In still other instances, it may be suitable to add a suitable non-ionic solute that can help balance the osmotic potential of the aqueous composition.

As used herein, the term "botanical biomass" generally refers to any and all parts of a botanical source comprising one or more of monocaffeoylquinic acids, dicaffeoylquinic acid, and salts thereof, including the botanical source leaves, stalks, stems, tops, roots, and the like. The botanical biomass can be in any suitable form including in comminuted form resulting from, e.g., from chopping the botanical biomass prior to and/or during the contacting with the aqueous composition. For example, the botanical biomass can be comminuted in a suitable container and the aqueous composition can be added to the comminuted botanical biomass, thus "contacting" the botanical biomass. The comminuted botanical biomass can then be optionally further comminuted within the suitable container. Or the botanical biomass can be placed in a suitable container, to which the aqueous composition is added, thus "contacting" the botanical biomass, and the resulting composition can be comminuted.

The botanical biomass can be stirred, sonicated or otherwise agitated prior to and/or during the contacting to, among other things, maximize the extraction of the at least one of monocaffeoylquinic acids and dicaffeoylquinic acids, and salts thereof.

The initial extract can be carried through to step (CC) as-is or bulk solids and or plant solids present, such as comminuted botanical plant leaves, stalks, tops, roots, and the like, can be removed in step (BB) of the methods described herein. When step (BB) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Step (CC) of the methods described herein involves adjusting the volume of the initial extract or second initial extract with a first aqueous composition or a second aqueous composition, respectively, to obtain an adjusted initial extract or adjusted second initial extract. The first and second aqueous compositions can be different or the same. The adjusted initial extract or adjusted second initial extract can be filtered at this point or can be carried through to step (DD) as-is. The initial extract or the second initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

The volume of the initial extract or second initial extract can be adjusted with a sufficient amount of an aqueous composition (e.g., water) to obtain an adjusted initial extract or adjusted second initial extract to, among other things, increase the binding of the at least one of monocaffeoylquinic acids and dicaffeoylquinic acids, and salts thereof, to the ion exchange chromatography column used in step (DD) of the methods described herein, relative to an unadjusted initial extract or an unadjusted second initial extract.

The volume of the initial extract or second initial extract can be adjusted to, among other things, adjust the amount of organic solvent, when present, in the initial extract or second initial extract. The volume of the initial extract or second initial extract can be adjusted such that the adjusted initial extract or adjusted second initial extract comprises less than about 60%, less than about 50%, less than about 40%, less than about 30%, less than about 20%, less than about 10%, less than about 5%, less than about 1% or even about 0% by volume organic solvent, the balance being water; or from about 0% to about 40%, about 0% to about 30%, about 10% to about 40%, about 10% to about 30%, about 20% to about 40%, about 30% to about 40%, or about 35% by volume organic solvent, the balance being water.

Step (DD) of the methods described herein involves chromatographing the adjusted initial extract or the second initial extract on an ion exchange stationary phase (e.g., a weak anion exchange stationary phase). The chromatographing can be performed in any suitable fashion, including in batch mode or using a column. The chromatographing can be performed with an aqueous composition (e.g., an aqueous composition comprising a (C1-C4)alkanol) as eluent (e.g., an aqueous composition comprising from about 0% to about 40%, about 0% to about 30%, about 10% to about 40%, about 10% to about 30%, about 20% to about 40%, about 30% to about 40%, or about 35% by volume (C1-C4) alkanol, the balance being water), leaving the at least one of monocaffeoylquinic acids and dicaffeoylquinic acids, and salts thereof, adsorbed on the weak ion exchange chromatography column, while eluting other compounds including caffeine, quercitrin, hyperoside, astragalin, avicularin, sophoricoside, and rutin (also known as rutoside, quercetin-3-O-rutinoside, and sophorin)

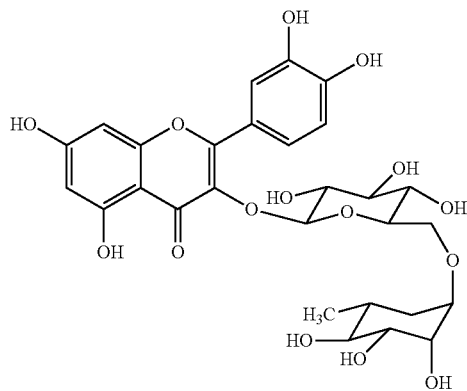 [SMILES: CC1CC(OCC2OC(Oc3c(-c4ccc(O)c(O)c4)oc4cc(O)cc(O)c4c3=O)C(O)C(O)C2O)C(O)C(O)C1O]

and isomers thereof. Step (DD) of the methods described herein can decrease the concentration of at least one of caffeine, quercitrin, hyperoside, astragalin, avicularin, sophoricoside, rutin, and rutin isomers to a concentration of less than 1%, less than 0.5%, less than 0.1%, less than 0.05%, less than 0.01% or less than 0.001% by mass. The instant disclosure therefore contemplates botanical extracts comprising less than 0.1% of at least one of caffeine, quercitrin, hyperoside, astragalin, avicularin, sophoricoside, rutin, and rutin isomers by mass. The instant disclosure also contemplates botanical extracts comprising less than 0.5% by mass of each one of caffeine, quercitrin, hyperoside, astragalin, avicularin, sophoricoside, rutin, and rutin isomers and a less than about 1% by mass of caffeine, quercitrin, hyperoside, astragalin, avicularin, sophoricoside, rutin, and rutin isomers combined. The instant disclosure also contemplates botanical extracts that are effectively free of at least one of caffeine, quercitrin, hyperoside, astragalin, avicularin, sophoricoside, rutin, and rutin isomers (e.g., free of caffeine, free of quercitrin, free of hyperoside, free of astragalin, free of avicularin, free of sophoricoside, free of rutin, free of rutin isomers, and/or free of caffeine, rutin, and rutin isomers).

The ion exchange stationary phase is non-limiting and can be any suitable ion exchange chromatography stationary phase. Examples of suitable ion exchange chromatography stationary phases include ANX-SEPHAROSE® fast flow resin, DEAE SEPHAROSE®, DEAE SEPHADEX® A25 resin, AMBERLITE® (FPA 53; FPA 55; CG-50 Type I; IRC-50; IRC-50S; and IRP-64), DIAION WA10, and DOWEX® CCR-3.

The ion exchange chromatography stationary phase can optionally be pre-conditioned with an aqueous composition (e.g., an aqueous composition comprising a (C1-C4)alkanol), such as an aqueous composition comprising from about 0% to about 40%, about 0% to about 30%, about 10% to about 40%, about 10% to about 30%, about 20% to about 40%, about 30% to about 40%, or about 35% by volume (CJ-C4)alkanol, the balance being water, prior to the chromatographing of the adjusted initial extract or adjusted second initial extract. For example, the weak ion exchange chromatography column can be pre-conditioned with about 2 or more bed volumes (BV) at a flow rate of about 2 BV/h.

The pH of the weak ion exchange chromatography column can optionally be adjusted prior to the chromatographing of the adjusted initial extract or adjusted second initial extract. For example, the pH of the weak ion exchange chromatography column can be adjusted prior to the chromatographing with any suitable acid (e.g., hydrochloric acid) such that the pH of the weak ion exchange chromatography column (e.g., the pH of the resin/stationary phase) is a pH of less than about 10, about 9 or less, about 8 or less, about 7 or less, about 6 or less, about 5 or less, about 4 or less, about 3 or less; or a pH of about 2 to about 10, about 3 to about 8, about 5 to about 9, about 2 to about 6; about 3 to about 4; or about 3 to about 6. The pH of the weak ion exchange chromatography column can be adjusted before or after the column is optionally pre-conditioned with the aqueous composition comprising a (C1-C4) prior to the chromatographing of the adjusted initial extract or adjusted second initial extract.

After pre-conditioning and/or adjusting of the pH of the weak ion exchange chromatography column, the adjusted initial extract or adjusted second initial extract can be loaded onto the column at any suitable rate, such as at a rate of above 2 BV/h (bed volumes per hour). After loading the adjusted initial extract or adjusted second initial extract, the column can be washed with any suitable volume of an aqueous composition comprising a (C1-C4)alkanol (e.g., at least about 2 BV, at least about 3 BV or at least about 4 BV of an aqueous composition comprising from about 10% to about 40%, about 10% to about 30%, about 20% to about 40%, about 30% to about 40%, or about 35% by volume (C1-C4)alkanol, the balance being water) at any suitable rate, such as at a rate of about 2 BV/h. The volume of aqueous composition comprising a (C1-C4)alkanol can be discarded, as it will contain, among other things, caffeine, quercitrin, hyperoside, astragalin, avicularin, sophoricoside, rutin, and rutin isomers.

Step (EE) of the methods described herein involves eluting the adsorbed at least one of monocaffeoylquinic acids and dicaffeoylquinic acids, and salts thereof, from the weak ion exchange chromatography column to obtain a first eluent comprising the at least one of monocaffeoylquinic acids and dicaffeoylquinic acids, and salts thereof. The eluting is performed under any conditions suitable to elute the at least one of monocaffeoylquinic acids and dicaffeoylquinic acids, and salts thereof from the column.

An example of suitable conditions to elute the at least one of monocaffeoylquinic acids and dicaffeoylquinic acids, and salts thereof from the column include eluting the column with any suitable volume of a solution comprising a salt (e.g., sodium chloride, potassium chloride, ammonium chloride, sodium sulfate, potassium sulfate, sodium phosphate, potassium phosphate, and the like). Examples of solutions comprising a salt include solutions comprising at least one salt (e.g., about 5 wt. % to about 25 wt. %, about 15 wt. % to about 20 wt. % or about 5 wt. % to about 10 wt. % of a salt) dissolved in an aqueous composition comprising a (C1-C4)alkanol (e.g., at least about 2 BV, at least about 3 BV or at least about 4 BV of an aqueous composition comprising from about 10% to about 60%, about 20% to about 50%, about 30% to about 55%, about 40% to about 60%, or about 50% by volume (C1-C4)alkanol).

Another example of suitable conditions to elute the at least one of monocaffeoylquinic acids and dicaffeoylquinic acids, and salts thereof from the column include eluting the column with any suitable volume of a solution comprising an acid (e.g., hydrochloric acid, sulfuric acid, phosphoric acid, acetic acid, formic acid, and the like). Examples of solutions comprising an acid include solutions comprising hydrochloric acid and the like and optionally acids solutions comprising an aqueous composition comprising from about 10% to about 60%, about 20% to about 50%, about 30% to about 55%, about 40% to about 60%, or about 50% by volume (C1-C4)alkanol).

The first eluent comprising the at least one of monocaffeoylquinic acids and dicaffeoylquinic acids, and salts thereof, collected from the eluting step is collected and can be subsequently concentrated by removing solvent (e.g., to remove water and (C1-C4)alkanol) by any suitable means to provide a concentrate comprising the at least one of monocaffeoylquinic acids and dicaffeoylquinic acids, and salts thereof. The solvent removal can be accomplished under an inert atmosphere (e.g., under a nitrogen gas atmosphere). While not wishing to be bound by any specific theory, it is believed that performing the solvent removal under an inert atmosphere can reduce the formation of highly colored polymeric substances that either natively exist in the botanical biomass or form at one or more of the steps described herein.

The first eluent comprising the at least one of monocaffeoylquinic acids and dicaffeoylquinic acids, and salts thereof comprises a solvent. The solvent can be removed in a step (FF) to dryness or it can be removed to a point where a volume of an aqueous composition comprising a (C1-C4) alkanol remains as a solvent (e.g., about 50%, about 40%, about 30% about 20%, about 10% or about 5% of an original, total volume of the eluent) to form a concentrate, though the ratio of components that make up the aqueous composition comprising a (C1-C4)alkanol may or may not be different from the ratio of components that made up the aqueous composition comprising a (C1-C4)alkanol that was used to elute the adsorbed at least one of monocaffeoylquinic acids and dicaffeoylquinic acids, and salts thereof. Alternatively, the solvent in the eluent comprising the at least one of monocaffeoylquinic acids and dicaffeoylquinic acids, and salts thereof, can be removed to a point where a volume of an aqueous composition comprising a (C1-C4)alkanol remains, wherein the aqueous composition comprising a (C1-C4)alkanol comprises less than about 10%, less than about 5%, less than about 2% or less than about 1% by volume (C1-C4)alkanol.

Suitable conditions for removing solvent from the eluent comprising the at least one of monocaffeoylquinic acids and dicaffeoylquinic acids, and salts thereof, to form a concentrate comprising the at least one of monocaffeoylquinic acids and dicaffeoylquinic acids, and salts thereof include blowing an inert gas (e.g., nitrogen gas) over the surface of the eluent. The eluent can be heated while blowing the nitrogen gas or it can be at room temperature (e.g., 25° C.). Other conditions for removing the solvent in the eluent include applying a vacuum to the container containing the eluent. The vacuum can be applied with the eluent at room temperature or while heating the container. Yet other conditions for removing solvent in the eluent include passing the eluent through a wiped film evaporator or an agitated thin film evaporator.

The pH of the concentrate can be adjusted at this point to obtain a pH-adjusted concentrate, though adjusting the pH at this point is optional. For example, the pH of the concentrate can be adjusted to a pH where the at least one of monocaffeoylquinic acids and dicaffeoylquinic acids, and salts thereof are protected from degradation. Suitable pHs include pHs of less than about 6, less than about 5, less than about 4, less than about 3 or less than about 2; such as a pH of from about 2 to about 6, about 2 to about 5, about 2 to about 4, about 3 to about 5 or a pH of about 3.5. The pH of the concentrate can be adjusted by using any suitable acid or base. When an acid is used, the acid can be hydrochloric acid and the like.

The concentrate or the pH-adjusted concentrate can be taken on as-is in the methods described herein or the removing step (FF) or they can be filtered. The concentrate or the pH-adjusted concentrate can be filtered using any suitable filter (e.g., low ash filter paper, such as Whatman 44 or 54 low ash filter paper), a nylon filter, a polyethersulfone filter, a glass fiber filter, a pad of diatomaceous earth, and the like. In some instances, the pH-adjusted concentrate can be filtered through a polymeric membrane, such as a polyethersulfone (PES) filter having, e.g., 0.2 µm pore size, or a pleated (flat membrane, vacuum filtration) or a pleated PES membrane, depending on the volume of the concentrate or the pH-adjusted concentrate.

The concentrate comprising the at least one of monocaffeoylquinic acids and dicaffeoylquinic acids, and salts thereof, whether it is pH-adjusted, filtered or both pH-adjusted and filtered, can be taken directly to drying step (HH) or can be submitted for desalting/decoloring in step (GG) (in either order, including desalting, followed by decoloring; decoloring, followed by desalting; decoloring, but not desalting; or desalting, but not decoloring) of a concentrate that can be highly colored. The desalting/decoloring can be accomplished under an inert atmosphere (e.g., under a nitrogen gas atmosphere). While not wishing to be bound by any specific theory, it is believed that performing the one or more steps under an inert atmosphere can reduce the formation of highly colored polymeric substances that either natively exist in the botanical biomass or form at one or more of the steps described herein.

The concentrate, whether it is pH-adjusted, filtered or both pH-adjusted and filtered, can be decolored by any suitable means, including ultrafiltration (e.g., filtering through a molecular weight cutoff membrane, size-exclusion chromatography or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the botanical biomass or form at one or more of the steps described herein.

The filtrate from decoloring can be taken on to drying step (HH) or it can be desalted in step (GG). Alternatively, the concentrate, whether it is pH-adjusted, filtered or both pH-adjusted and filtered, can be desalted without first decoloring. Regardless, the desalting can be accomplished using a nanofiltration membrane and a hydrophobic resin. Those of skill in the art would recognize that when one uses a nanofiltration membrane and a hydrophobic resin one discards the permeate and keeps the retentate. In one example, desalting can be accomplished using a hydrophobic resin (e.g., a porous poly divinylbenzene/ethylvinylbenzene matrix, such as SEPABEADS™ SP70), where one would load a pH-adjusted concentrate (e.g., an acidified concentrate, with a pH of less than about 2) comprising less than about 20% by volume (C1-C4)alkanol. The resin is then washed with dilute alcohol (e.g., less than about 10% by volume (C1-C4)alkanol, the rest being water having a pH of less than about 2) and then eluted with an aqueous composition comprising about 70% by volume (C1-C4)alkanol in water to obtain a desalted second eluent comprising the at least one of monocaffeoylquinic acids and dicaffeoylquinic acids, and salts thereof.

If desalting precedes decoloring in step (GG), the solvent in the permeate from the desalting step can be removed to a point where a volume of an aqueous composition comprising a (C1-C4)alkanol remains as a solvent (e.g., about 50%, about 40%, about 30% about 20%, about 10% or about 5% of an original, total volume of the eluent) to form a first desalted concentrate. Alternatively, the solvent in the permeate from the desalting can be removed, to give a second desalted concentrate, to a point where a volume of an aqueous composition comprising a (C1-C4)alkanol remains, wherein the aqueous composition comprising a (C1-C4) alkanol comprises less than about 10%, less than about 5%, less than about 2% or less than about 1% by volume (C1-C4)alkanol. The first desalted concentrate can also have the attributes of the second desalted concentrate, such that the first desalted concentrate also has less than about 10%, less than about 5%, less than about 2% or less than about 1% by volume (C1-C4)alkanol.

Suitable conditions for removing solvent from the permeate comprising the at least one of, monocaffeoylquinic acids, and dicaffeoylquinic acids, and salts thereof, to form a first/second desalted concentrate comprising the at least one of monocaffeoylquinic acids and dicaffeoylquinic acids, and salts thereof include blowing an inert gas (e.g., nitrogen gas) over the surface of the eluent. The permeate can be heated while blowing the nitrogen gas or it can be at room temperature (e.g., 25° C.). Other conditions for removing the solvent in the eluent include applying a vacuum to the container containing the permeate. The vacuum can be applied with the permeate at room temperature or while heating the container. Yet other conditions for removing solvent in the permeate include passing the permeate through a wiped film evaporator or an agitated thin film evaporator.

In another example, the concentrate comprising the at least one of monocaffeoylquinic acids and dicaffeoylquinic acids, and salts thereof can be filtered through filter paper to obtain a first filtrate, the first filtrate is ultrafiltered to obtain a second filtrate, and the second filtrate is nanofiltered using a nanofiltration membrane to obtain a first retentate or the second filtrate is eluted through a hydrophobic resin to obtain a desalted second eluent. In another example, the concentrate comprising the at least one of monocaffeoylquinic acids and dicaffeoylquinic acids, and salts thereof can be filtered through filter paper to obtain a first filtrate, the first filtrate is nanofiltered using a nanofiltration membrane to obtain a third retentate or the first filtrate is eluted through a hydrophobic resin to obtain a desalted second eluent, and the third retentate or the desalted second eluent is ultrafiltered to obtain a third filtrate.

As mentioned herein, the eluent comprising the at least one of monocaffeoylquinic acids and dicaffeoylquinic acids, and salts thereof, can be concentrated to dryness or it can be concentrated to a point where a volume of an aqueous composition comprising a (C1-C4)alkanol remains. If the eluent is concentrated to dryness, the dry material can be reconstituted using, for example, an aqueous composition comprising a (C1-C4)alkanol. The reconstituted material can then be filtered as described herein, to among other things, at least one of desalt and decolor.

The methods described herein can include step (HH) that involves drying first retentate, desalted second eluent or the third filtrate to obtain the composition comprising the at least one of monocaffeoylquinic acids and dicaffeoylquinic acids, and salts thereof. The first retentate, desalted second eluent or the third filtrate can be dried in any suitable manner, including by lyophilization or spray drying.

Another example of a method for making a composition comprising at least one of monocaffeoylquinic acids and dicaffeoylquinic acids, and salts thereof, the method comprising (1) contacting botanical biomass with an aqueous composition to obtain an initial extract;

(2) removing solids from the initial extract to obtain a second initial extract;

(3) contacting the second initial extract with acidified ethyl acetate to obtain an acidic ethyl acetate extract;

(4) neutralizing the acidic ethyl acetate extract to obtain neutralized ethyl acetate and an aqueous extract;

(5) decoloring the aqueous extract to obtain a decolored aqueous extract; and (6) drying the decolored aqueous extract to obtain the composition comprising at least one of monocaffeoylquinic acids and dicaffeoylquinic acids, and salts thereof.

Steps (1), (2), and (6) are performed as described herein for steps (AA), (BB), and (HH). Step (5) is analogous to filtering step (GG), except that step (5) involves only decoloring processes, such as ultrafiltration, which includes filtering through a molecular weight cutoff membrane, size-exclusion chromatography, and gel permeation, as discussed herein. Accordingly, the disclosure with regard to steps (AA), B(B), (GG), and (HH) applies to steps (1), (2), (5), and (6).

Step (1) of the methods described herein involve contacting botanical biomass with an aqueous composition to obtain an initial extract comprising at least one of monocaffeoylquinic acids and dicaffeoylquinic acids, and salts thereof.

The aqueous composition can comprise water and not contain any co-solvents, such as organic solvents. But the aqueous composition can comprise co-solvents, in addition to water. Suitable co-solvents include organic solvents, such as, (C1-C4)alkanols and mixtures of (C1-C4)alkanols. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60% by volume organic solvent, the balance being water; or from about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, phosphoric acid, sulfuric acid, nitric acid or the like can be useful in the aqueous composition, with or without a co-solvent. Alternatively, pure water made basic to pH 7-11 with hydroxide, such as sodium or potassium hydroxide can be useful in the aqueous composition, with or without a co-solvent. In still other instances, it may be suitable to add a suitable non-ionic solute that can help balance the osmotic potential of the aqueous composition.

The botanical biomass can be stirred, sonicated or otherwise agitated prior to and/or during the contacting of step (1) to, among other things, maximize the extraction of the at least one of monocaffeoylquinic acids and dicaffeoylquinic acids, and salts thereof.

The initial extract can be carried through to step (3) as-is or bulk solids and or plant solids present, such as comminuted leaves, stalks, tops, roots, and the like, can be removed in step (2) of the methods described herein. When step (2) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, a polyethersulfone filter, a glass fiber filter, a pad of diatomaceous earth, and the like.

Prior to carrying out step (3) one can optionally adjust the pH of the initial or second initial extract with a suitable acid. (e.g., hydrochloric acid and the like) or suitable base (e.g., sodium hydroxide) to a pH of between about 4 and about 7. The pH-adjusted initial or second initial extract is then extracted with ethyl acetate that has not been pre-acidified as described herein. While not wishing to be bound by any specific theory, it is believed that when the pH of the initial or second initial extract is adjusted to between about 4 and about 7, it is possible to extract certain impurities into the ethyl acetate, while keeping compounds of interest (e.g., monocaffeoylquinic acids and dicaffeoylquinic acids, and salts thereof) in the aqueous layer.

Step (3) of the methods described herein involves contacting the first or second initial extract with acidified ethyl acetate to obtain an acidic ethyl acetate extract. The acidified ethyl acetate can be prepared in any suitable manner, including by adding any suitable acid, including hydrochloric acid, sulfuric acid, and glacial acetic acid (e.g., 0.01-1% vol/vol). The acidic ethyl acetate extract is washed with water (e.g., three times, with 1:1 vol/vol water). Under these conditions, the at least one of monocaffeoylquinic acids and dicaffeoylquinic acids will substantially be in their conjugate acid form and will reside substantially in the acidic ethyl acetate layer that forms when the acidic ethyl acetate extract is washed with water. The water layers are discarded and the acidic ethyl acetate extract is carried on to step (4).

Step (3) of the methods described herein can be carried out in other suitable ways, including by using ethyl acetate that has not been pre-acidified as described herein (e.g., by pre-washing with glacial acetic acid), but instead by adjusting the pH of the initial or second initial extract with a suitable acid. (e.g., hydrochloric acid and the like), then extracting the pH-adjusted initial or second initial extract with ethyl acetate that has not been pre-acidified. Regardless of the acid used to adjust the pH of the initial extract or the second initial extract, the pH of the initial extract or the second initial extract is adjusted to about 4 or less, 3 or less, about 2 or less, or about 1 or less. The water layers are discarded and the acidic ethyl acetate extract that results is carried on to step (4).

Step (4) of the methods described herein involves neutralizing the acidic ethyl acetate extract to obtain neutralized ethyl acetate and an aqueous extract. This is accomplished in any suitable way, including washing the acidic ethyl acetate extract with water (e.g., three times, with 1:1 vol/vol water) comprising a suitable base, such as sodium hydroxide, potassium hydroxide, and the like, and combinations thereof. Under these conditions, the at least one of monocaffeoylquinic acids and dicaffeoylquinic acids will substantially be in their conjugate base form and will substantially reside in the water layer that forms when the acidic ethyl acetate extract is washed with water comprising a suitable base.

In an alternative, optional step to step (4), step (4-a), the acidic ethyl acetate extract that results from step (3) can be optionally removed, even removed to dryness. Any solid that remains can either be reconstituted with pH neutral water (e.g., deionized water) and the pH of the water can then be adjusted to about 3 to about 7; or the solid that remains can be reconstituted with water having a pH of about 3 to about 7.

The aqueous extract comprising the at least one of monocaffeoylquinic acids and dicaffeoylquinic acids, and salts thereof, whether they emanate from step (4) or step (4-a), can then be submitted for step (5) to accomplish, among other things, decoloring of aqueous extract, which can be highly colored. Decoloring can be accomplished by any suitable means, including ultrafiltration (e.g., filtering through a molecular weight cutoff membrane, size-exclusion chromatography, or gel permeation). One obtains a filtrate from decoloring. Ultrafiltration accomplishes, among other things, decoloration of a concentrate that can be highly colored. While not wishing to be bound by any specific theory, it is believed that ultrafiltration removes highly colored polymeric substances that either natively exist in the botanical biomass or form at one or more of the steps described herein.

Another example of modifications to the method described herein comprising steps (1)-(6) (including the alternative, optional step (4-a) includes a method for making a composition comprising at least one of monocaffeoylquinic acids and dicaffeoylquinic acids, and salts thereof, the method comprising contacting botanical biomass with an aqueous composition to obtain an initial extract;

removing solids from the initial extract to obtain a second initial extract;

adjusting the pH of the second initial extract to a pH of from about 4 to about 7 to obtain a first pH-adjusted second initial extract;

contacting the first pH-adjusted second initial extract with ethyl acetate to obtain a first ethyl acetate extract and a second aqueous extract;

adjusting the pH of the second aqueous extract to a pH of less than 2 to obtain a pH-adjusted second aqueous extract;

contacting the pH-adjusted second aqueous extract with ethyl acetate to obtain a second ethyl acetate extract;

removing the ethyl acetate from the second ethyl acetate extract to obtain a purified composition;

reconstituting the crude composition with water to obtain a third aqueous extract; and decoloring the third aqueous extract to obtain a decolored aqueous extract.

The "purified composition" will comprise the compounds of interest (e.g., the at least one of monocaffeoylquinic acids and dicaffeoylquinic acids, and salts thereof) and is purified relative to at least the initial extract and the second initial extract, in that the "purified composition" will not contain certain impurities in the initial extract and the second initial extract, but does contain highly colored polymeric substances that either natively exist in the botanical biomass or form at one or more of the steps described herein and that are removed in the decoloring step.

Yet another example of modifications to the method described herein comprising steps (1)-(6) (including the alternative, optional step (4-a) includes a method for making a composition comprising at least one of monocaffeoylquinic acids and dicaffeoylquinic acids, and salts thereof, the method comprising contacting botanical biomass with an aqueous composition to obtain an initial extract;

removing solids from the initial extract to obtain a second initial extract;

adjusting the pH of the second initial extract to a pH of less than about 2 to obtain a second pH-adjusted second initial extract;

contacting the second pH-adjusted second initial extract with ethyl acetate to obtain a third ethyl acetate extract;

neutralizing the third ethyl acetate extract to obtain a first neutralized ethyl acetate extract and a third aqueous extract; and decoloring the third aqueous extract to obtain a decolored aqueous extract.

The methods described herein can include step (6) that involves drying the decolored aqueous extract to obtain the composition comprising the at least one of caffeic acid, monocaffeoylquinic acids, and dicaffeoylquinic acids, and salts thereof. The first or second retentates or the third filtrate can be dried in any suitable manner, including by lyophilization or spray drying.

An example of a method for making a composition comprising at least one of monocaffeoylquinic acids and dicaffeoylquinic acids, and salts thereof, the method comprising (A1) contacting botanical biomass with an aqueous composition to obtain an initial extract;

(A2) adjusting a volume of the initial extract to obtain a second initial extract;

(A3) contacting the second initial extract with ethyl acetate to obtain an aqueous fraction;

(A4) acidifying the aqueous fraction and contacting with ethyl acetate to obtain an ethyl acetate fraction;

(A5) drying and reconstituting the ethyl acetate fraction to obtain a decolored fraction;

(A6) chromatographing the decolored fraction on an ion exchange chromatography stationary phase;

(A7) eluting the ion exchange chromatography stationary phase to obtain a first eluent comprising a solvent;

(A8) removing the solvent to form a concentrate;

(A9) desalting the concentrate to form a desalted concentrate; and (A10) drying the desalted concentrate to obtain the composition comprising at least one of monocaffeoylquinic acids and dicaffeoylquinic acids, and salts thereof.

Step (A1) of the methods described herein involve contacting botanical biomass with an aqueous composition to obtain an initial extract comprising at least one of monocaffeoylquinic acids and dicaffeoylquinic acids, and salts thereof (e.g., quaternary ammonium, sodium, potassium, lithium, magnesium, and calcium salts).

The aqueous composition can comprise water and not contain any co-solvents, such as organic solvents. But the aqueous composition can comprise co-solvents, in addition to water. Suitable co-solvents include organic solvents, such as, (C1-C4)alkanols and mixtures of (C1-C4)alkanols. By "(C1-C4)alkanol" is meant an alcohol of the formula (C1-C4)alkyl-OH, wherein "alkyl" refers to straight chain and branched alkyl groups having from 1 to 4 carbon atoms such as methyl, ethyl, n-propyl, n-butyl, isopropyl, iso-butyl, sec-butyl, and t-butyl, such that the resulting (C1-C4)alkanol is methanol, ethanol, n-propanol, n-butanol, isopropanol, iso-butanol, sec-butanol, and t-butanol. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60%, up to about 70%, up to about 80%, up to about 90% or up to 100% by volume organic solvent the balance being water, except when the aqueous composition comprises 100% by volume organic solvent; or from about 30% to about 100%, about 50% to about 100%, about 60% to about 90%, about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively, pure water made basic to pH 7-11 with hydroxide, such as with sodium or potassium hydroxide, can be useful in the aqueous composition, with or without a co-solvent. In still other instances, it may be suitable to add a suitable non-ionic solute that can help balance the osmotic potential of the aqueous composition.

As used herein, the term "botanical biomass" generally refers to any and all parts of a botanical source comprising one or more of monocaffeoylquinic acids, dicaffeoylquinic acid, and salts thereof, including the botanical source leaves, stalks, stems, tops, roots, and the like. The botanical biomass can be in any suitable form including in comminuted form resulting from, e.g., from chopping the botanical biomass prior to and/or during the contacting with the aqueous composition. For example, the botanical biomass can be comminuted in a suitable container and the aqueous composition can be added to the comminuted botanical biomass, thus "contacting" the botanical biomass. The comminuted botanical biomass can then be optionally further comminuted within the suitable container. Or the botanical biomass can be placed in a suitable container, to which the aqueous composition is added, thus "contacting" the botanical biomass, and the resulting composition can be comminuted.

The botanical biomass can be stirred, sonicated or otherwise agitated prior to and/or during the contacting to, among other things, maximize the extraction of the at least one of monocaffeoylquinic acids and dicaffeoylquinic acids, and salts thereof.

The initial extract can be carried through to step (B1) as-is or bulk solids and or plant solids present, such as comminuted botanical plant leaves, stalks, tops, roots, and the like, can be removed in step (A1) of the methods described herein.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Step (A2) of the methods described herein involves adjusting the volume of the initial extract with a first aqueous composition, respectively, to obtain a second initial extract. The second initial extract can be filtered at this point or can be carried through to step (C3) as-is. The second initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

The volume of the initial extract can be adjusted to, among other things, adjust the amount of organic solvent, when present, in the second initial extract. The volume of the initial extract can be adjusted such that the second initial extract comprises less than about 60%, less than about 50%, less than about 40%, less than about 30%, less than about 20%, less than about 10%, less than about 5%, less than about 1% or even about 0% by volume organic solvent, the balance being water; or from about 0% to about 40%, about 0% to about 30%, about 10% to about 40%, about 10% to about 30%, about 20% to about 40%, about 30% to about 40%, or about 35% by volume organic solvent, the balance being water.

Step (A3) of the methods described herein involves contacting the second initial extract with ethyl acetate to obtain an aqueous fraction. The second initial extract is diluted with an equal volume of water followed by an equal volume of ethyl acetate, shaken, and resulting aqueous fraction is retained.

Step (A4) of the methods described herein involves acidifying the aqueous fraction and contacting with ethyl acetate to obtain an ethyl acetate fraction. The aqueous fraction is acidified, an equal volume of ethyl acetate is added, shaken, the ethyl acetate fraction retained and a second aqueous fraction discarded. Optionally, the second aqueous fraction can also be retained and extracted a second time with ethyl acetate to obtain a second ethyl acetate fraction.

Step (A5) of the methods described herein involves drying and reconstituting the ethyl acetate fraction to obtain a decolored fraction. The retained ethyl acetate fraction (and second ethyl acetate fraction) is dried to remove solvent and then reconstituted with water to obtain a decolored fraction.

Step (A6) of the methods described herein involves chromatographing the decolored fraction on an ion exchange stationary phase (e.g., a weak anion exchange stationary phase). The chromatographing can be performed in any suitable fashion, including in batch mode or using a column. The chromatographing can be performed with an aqueous composition (e.g., an aqueous composition comprising a (C1-C4)alkanol) as eluent (e.g., an aqueous composition comprising from about 0% to about 40%, about 0% to about 30%, about 10% to about 40%, about 10% to about 30%, about 20% to about 40%, about 30% to about 40%, or about 35% by volume (C1-C4)alkanol, the balance being water), leaving the at least one of monocaffeoylquinic acids and dicaffeoylquinic acids, and salts thereof, adsorbed on the weak ion exchange chromatography column, while eluting other compounds.

The ion exchange stationary phase is non-limiting and can be any suitable ion exchange chromatography stationary phase. Examples of suitable ion exchange chromatography stationary phases include ANX-SEPHAROSE® fast flow resin, DEAE SEPHAROSE®, DEAE SEPHADEX® A25 resin, AMBERLITE® (FPA 53; FPA 55; CG-50 Type I; IRC-50; IRC-50S; and IRP-64), DIAION WA10, and DOWEX® CCR-3.

The ion exchange chromatography stationary phase can optionally be pre-conditioned with an aqueous composition (e.g., an aqueous composition comprising a (C1-C4)alkanol), such as an aqueous composition comprising from about 0% to about 40%, about 0% to about 30%, about 10% to about 40%, about 10% to about 30%, about 20% to about 40%, about 30% to about 40%, or about 35% by volume (C1-C4)alkanol, the balance being water, prior to the chromatographing of the adjusted initial extract or adjusted second initial extract. For example, the weak ion exchange chromatography column can be pre-conditioned with about 2 or more bed volumes (BV) at a flow rate of about 2 BV/h.

The pH of the weak ion exchange chromatography column can optionally be adjusted prior to the chromatographing of the adjusted initial extract or adjusted second initial extract. For example, the pH of the weak ion exchange chromatography column can be adjusted prior to the chromatographing with any suitable acid (e.g., hydrochloric acid) such that the pH of the weak ion exchange chromatography column (e.g., the pH of the resin/stationary phase) is a pH of less than about 10, about 9 or less, about 8 or less, about 7 or less, about 6 or less, about 5 or less, about 4 or less, about 3 or less; or a pH of about 2 to about 10, about 3 to about 8, about 5 to about 9, about 2 to about 6; about 3 to about 4; or about 3 to about 6. The pH of the weak ion exchange chromatography column can be adjusted before or after the column is optionally pre-conditioned with the aqueous composition comprising a (C1-C4) prior to the chromatographing of the adjusted initial extract or adjusted second initial extract.

After pre-conditioning and/or adjusting of the pH of the weak ion exchange chromatography column, the adjusted initial extract or adjusted second initial extract can be loaded onto the column at any suitable rate, such as at a rate of above 2 BV/h (bed volumes per hour). After loading the adjusted initial extract or adjusted second initial extract, the column can be washed with any suitable volume of an aqueous composition comprising a (C1-C4)alkanol (e.g., at least about 2 BV, at least about 3 BV or at least about 4 BV of an aqueous composition comprising from about 10% to about 40%, about 10% to about 30%, about 20% to about 40%, about 30% to about 40%, or about 35% by volume (C1-C4)alkanol, the balance being water) at any suitable rate, such as at a rate of about 2 BV/h. The volume of aqueous composition comprising a (C1-C4)alkanol can be discarded, as it will contain, among other things, caffeine, quercitrin, hyperoside, astragalin, avicularin, sophoricoside, rutin, and rutin isomers.

Step (A7) of the methods described herein involves eluting the adsorbed at least one of monocaffeoylquinic acids and dicaffeoylquinic acids, and salts thereof, from the weak ion exchange chromatography column to obtain a first eluent comprising the at least one of monocaffeoylquinic acids and dicaffeoylquinic acids, and salts thereof. The eluting is performed under any conditions suitable to elute the at least one of monocaffeoylquinic acids and dicaffeoylquinic acids, and salts thereof from the column.

An example of suitable conditions to elute the at least one of monocaffeoylquinic acids and dicaffeoylquinic acids, and salts thereof from the column include eluting the column with any suitable volume of a solution comprising a salt (e.g., sodium chloride, potassium chloride, ammonium chloride, sodium sulfate, potassium sulfate, sodium phosphate, potassium phosphate, and the like). Examples of solutions comprising a salt include solutions comprising at least one salt (e.g., about 5 wt. % to about 25 wt. %, about 15 wt. % to about 20 wt. % or about 5 wt. % to about 10 wt. % of a salt) dissolved in an aqueous composition comprising a (C1-C4)alkanol (e.g., at least about 2 BV, at least about 3 BV or at least about 4 BV of an aqueous composition comprising from about 10% to about 60%, about 20% to about 50%, about 30% to about 55%, about 40% to about 60%, or about 50% by volume (C1-C4)alkanol).

Another example of suitable conditions to elute the at least one of monocaffeoylquinic acids and dicaffeoylquinic acids, and salts thereof from the column include eluting the column with any suitable volume of a solution comprising an acid (e.g., hydrochloric acid, sulfuric acid, phosphoric acid, acetic acid, formic acid, and the like). Examples of solutions comprising an acid include solutions comprising hydrochloric acid and the like and optionally acids solutions comprising an aqueous composition comprising from about 10% to about 60%, about 20% to about 50%, about 30% to about 55%, about 40% to about 60%, or about 50% by volume (C1-C4)alkanol).

The first eluent comprising the at least one of monocaffeoylquinic acids and dicaffeoylquinic acids, and salts thereof, collected from the eluting step is collected and can be subsequently concentrated by removing solvent (e.g., to remove water and (C1-C4)alkanol) by any suitable means to provide a concentrate comprising the at least one of monocaffeoylquinic acids and dicaffeoylquinic acids, and salts thereof. The solvent removal can be accomplished under an inert atmosphere (e.g., under a nitrogen gas atmosphere). While not wishing to be bound by any specific theory, it is believed that performing the solvent removal under an inert atmosphere can reduce the formation of highly colored polymeric substances that either natively exist in the botanical biomass or form at one or more of the steps described herein.

The first eluent comprising the at least one of monocaffeoylquinic acids and dicaffeoylquinic acids, and salts thereof comprises a solvent. The solvent can be removed in a step (A8) to dryness or it can be removed to a point where a volume of an aqueous composition comprising a (C1-C4) alkanol remains as a solvent (e.g., about 50%, about 40%, about 30% about 20%, about 10% or about 5% of an original, total volume of the eluent) to form a concentrate, though the ratio of components that make up the aqueous composition comprising a (C1-C4)alkanol may or may not be different from the ratio of components that made up the aqueous composition comprising a (C1-C4)alkanol that was used to elute the adsorbed at least one of monocaffeoylquinic acids and dicaffeoylquinic acids, and salts thereof. Alternatively, the solvent in the eluent comprising the at least one of monocaffeoylquinic acids and dicaffeoylquinic acids, and salts thereof, can be removed to a point where a volume of an aqueous composition comprising a (C1-C4)alkanol remains, wherein the aqueous composition comprising a (C1-C4)alkanol comprises less than about 10%, less than about 5%, less than about 2% or less than about 1% by volume (C1-C4)alkanol.

Suitable conditions for removing solvent from the eluent comprising the at least one of monocaffeoylquinic acids and dicaffeoylquinic acids, and salts thereof, to form a concentrate comprising the at least one of monocaffeoylquinic acids and dicaffeoylquinic acids, and salts thereof include blowing an inert gas (e.g., nitrogen gas) over the surface of the eluent. The eluent can be heated while blowing the nitrogen gas or it can be at room temperature (e.g., 25° C.). Other conditions for removing the solvent in the eluent include applying a vacuum to the container containing the eluent. The vacuum can be applied with the eluent at room temperature or while heating the container. Yet other conditions for removing solvent in the eluent include passing the eluent through a wiped film evaporator or an agitated thin film evaporator.

The concentrate comprising the at least one of monocaffeoylquinic acids and dicaffeoylquinic acids, and salts thereof, can be taken directly to drying step (A10) or can be submitted for desalting in step (A9).

The filtrate from decoloring can be taken on to drying step (A10) or it can be desalted in step (A9). The desalting can be accomplished using a hydrophobic resin. In one example, desalting can be accomplished using a hydrophobic resin (e.g., a Diaion SP70), where one would load the concentrate onto the resin. The resin is then washed with dilute alcohol (e.g., less than about 10% by volume (C1-C4)alkanol, the rest being water having a pH of less than about 2) and then eluted with an aqueous composition comprising about 70% by volume (C1-C4)alkanol in water to obtain a desalted concentrate comprising the at least one of monocaffeoylquinic acids and dicaffeoylquinic acids, and salts thereof.

The methods described herein can include step (A10) that involves drying the desalted concentrate to obtain the composition comprising the at least one of monocaffeoylquinic acids and dicaffeoylquinic acids, and salts thereof. The desalted concentrate can be dried in any suitable manner, including by lyophilization or spray drying.

Single Chromatographing Step

In one aspect, a method for making a composition comprising at least one of monocaffeoylquinic acids, dicaffeoylquinic acids, and salts thereof is preferred if the method results in an increased amount of at least one of monocaffeoylquinic acids, dicaffeoylquinic acids and salts at a reduced preferred content level of other off-taste compounds such as caffeine, rutin, rutin isomer, and other off-taste compounds as described below including for example the compounds listed below in Table 2. In one aspect, a method for making a composition comprising at least one of monocaffeoylquinic acids, dicaffeoylquinic acids, and salts thereof is preferred if the method results in an increased amount of at least one monocaffeoylquinic acids, dicaffeoylquinic acids, and salts thereof and a reduced level of other off-taste compounds such as caffeine, rutin, rutin isomers, and other off-taste compounds as described below in Table 2. In one aspect, a method is preferred if the method reduces the number of steps to achieve an acceptably reduced content level of off-taste compounds. In one aspect, a method is preferred if the method reduces the number of steps to achieve a composition of monocaffeoylquinic acids, dicaffeoylquinic acids, and salts thereof that has one or more off-taste compounds as described below in Table 2 at below the respective acceptable cutoff value. For example, such a method that reduces the number of steps to achieve an acceptably reduced content level of off-taste compounds produced is commercially advantageous because it reduces the costs and/or time required to produce an acceptable product. In one aspect, an example of a method that reduces the number of steps to achieve an acceptably reduced content level of off-taste compounds produced comprises a single chromatographing step. For example, a method that reduces the number of steps to achieve an acceptably reduced content level of off-taste compounds produced can comprise a single chromatographing step and can eliminate decoloring and desalting steps while still achieving an acceptably reduced content level of off-taste compounds produced. An example of a method for making a composition comprising at least one of monocaffeoylquinic acids, dicaffeoylquinic acids, and salts thereof while reducing the number of steps to achieve an acceptably reduced content level of off-taste compounds produced, comprises (B1) contacting botanical biomass with an aqueous composition to obtain an initial extract;

(B2) optionally filtering/removing solids from the initial extract;

(B3) chromatographing the initial extract on an ion exchange chromatography stationary phase;

(B4) eluting the stationary phase with a first elution composition to obtain a first eluent;

(B5) eluting the stationary phase with a second elution composition to obtain a second eluent; and (B6) solvent removal and/or drying.

Step (B1) of the methods described herein involves contacting botanical biomass with an aqueous composition to obtain an initial extract comprising at least one of monocaffeoylquinic acids, dicaffeoylquinic acids, and salts thereof (e.g., quaternary ammonium, sodium, potassium, lithium, magnesium, and calcium salts).

The aqueous composition can comprise water and can comprise co-solvents, in addition to water. Suitable co-solvents include organic solvents, such as, (C1-C4)alkanols and mixtures of (C1-C4)alkanols. By "(C1-C4)alkanol" is meant an alcohol of the formula (C1-C4)alkyl-OH, wherein "alkyl" refers to straight chain and branched alkyl groups having from 1 to 4 carbon atoms such as methyl, ethyl, n-propyl, n-butyl, isopropyl, iso-butyl, sec-butyl, and t-butyl, such that the resulting (C1-C4)alkanol is methanol, ethanol, n-propanol, n-butanol, isopropanol, iso-butanol, sec-butanol, and t-butanol. The proportion of organic solvent, such as (C1-C4)alkanol or mixtures of (C1-C4)alkanols, can be any suitable proportion such that the aqueous composition can comprise up to about 30%, up to about 40%, up to about 50% or up to about 60%, up to about 70%, up to about 80%, up to about 90% or up to about 100% by volume organic solvent the balance being water, except when the aqueous composition comprises 100% by volume organic solvent; or from about 30% to about 100%, about 50% to about 100%, about 60% to about 90%, about 30% to about 60%, about 40% to about 60%, about 30% to about 50%, about 40% to about 50%, or about 50% by volume organic solvent, the balance being water.

In some instances, the aqueous composition can be buffered with any suitable buffering system, including, but not limited to, a phosphate, citrate, ascorbate, lactate, acetate, and the like. Buffers can be in the range of 1-1000 mM of the anion. Alternatively, water acidified to pH 5-6 with hydrochloric acid, sulfuric acid, nitric acid or the like can be useful in the aqueous composition, with or without a co-solvent. Alternatively, pure water made basic to pH 7-11 with hydroxide, such as with sodium or potassium hydroxide, can be useful in the aqueous composition, with or without a co-solvent. In still other instances, it may be suitable to add a suitable non-ionic solute that can help balance the osmotic potential of the aqueous composition.

As used herein, the term "botanical biomass" generally refers to any and all parts of a botanical source (e.g. a botanical source as listed in Table t) comprising one or more of monocaffeoylquinic acids, dicaffeoylquinic acid, and salts thereof, including the botanical source leaves, stalks, stems, tops, roots, and the like. The botanical biomass can be in any suitable form including in comminuted form resulting from, e.g., from chopping the botanical biomass prior to and/or during the contacting with the aqueous composition. For example, the botanical biomass can be comminuted in a suitable container and the aqueous composition can be added to the comminuted botanical biomass, thus "contacting" the botanical biomass. The comminuted botanical biomass can then be optionally further comminuted within the suitable container. Or the botanical biomass can be placed in a suitable container, to which the aqueous composition is added, thus "contacting" the botanical biomass, and the resulting composition can be comminuted.

The botanical biomass can be stirred, sonicated or otherwise agitated prior to and/or during the contacting to, among other things, maximize the extraction of the at least one of monocaffeoylquinic acids and dicaffeoylquinic acids, and salts thereof.

The initial extract can be carried through to step (B3) as-is or bulk solids and or plant solids present, such as comminuted botanical plant leaves, stalks, tops, roots, and the like, can be removed in step (B2) of the methods described herein. When step (B2) is carried out, one obtains a second initial extract.

Bulk solids can be removed by any suitable method, including centrifugation, skimming, or filtration. For example, the initial extract can be filtered using any suitable filtration method, including gravity filtration or vacuum filtration through any suitable filter, so long as the filter does not substantially retain the at least one of monocaffeoylquinic acids and dicaffeoylquinic acids, and salts thereof, including a paper filter (e.g., low ash filter paper, such as Whatman 44 or 54 low ash filter paper), a nylon filter, polyethersulfone filter, a glass fiber filter, a pad of diatomaceous earth, and the like.

Step (B3) of the methods described herein involves chromatographing the initial extract or the second initial extract on an ion exchange stationary phase (e.g., a weak anion exchange stationary phase). The chromatographing can be performed in any suitable fashion, including in batch mode or using a column. The chromatographing can be performed with an aqueous composition (e.g., an aqueous composition comprising a (C1-C4)alkanol) as eluent (e.g., an aqueous composition comprising from about 0% to about 40%, about 0% to about 30%, about 10% to about 40%, about 10% to about 30%, about 20% to about 40%, about 30% to about 40%, or about 35% by volume (C1-C4)alkanol, the balance being water), leaving the at least one of monocaffeoylquinic acids and dicaffeoylquinic acids, and salts thereof, adsorbed on the weak ion exchange chromatography column, while eluting other compounds including caffeine, quercitrin, hyperoside, astragalin, avicularin, sophoricoside, and rutin (also known as rutoside, quercetin-3-O-rutinoside, and sophorin)

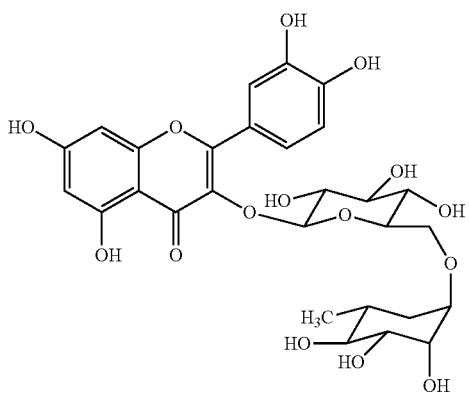 [SMILES: CC1CC(OCC2OC(Oc3c(-c4ccc(O)c(O)c4)oc4cc(O)cc(O)c4c3=O)C(O)C(O)C2O)C(O)C(O)C1O]

and isomers thereof.

Step (B3-B5) of the methods described herein can decrease the concentration of at least one of caffeine, quercitrin, hyperoside, astragalin, avicularin, sophoricoside, rutin, and rutin isomers to a concentration of less than 1%, less than 0.5%, less than 0.1%, less than 0.05%, less than 0.01% or less than 0.001% by mass. The instant disclosure therefore contemplates botanical extracts comprising less than 0.1% of at least one of caffeine, quercitrin, hyperoside, astragalin, avicularin, sophoricoside, rutin, and rutin isomers by mass. The instant disclosure also contemplates botanical extracts comprising less than 0.5% by mass of each one of caffeine, quercitrin, hyperoside, astragalin, avicularin, sophoricoside, rutin, and rutin isomers and a less than about 1% by mass of caffeine, quercitrin, hyperoside, astragalin, avicularin, sophoricoside, rutin, and rutin isomers combined. The instant disclosure also contemplates botanical extracts that are effectively free of at least one of caffeine, quercitrin, hyperoside, astragalin, avicularin, sophoricoside, rutin, and rutin isomers (e.g., free of caffeine, free of quercitrin, free of hyperoside, free of astragalin, free of avicularin, free of sophoricoside, free of rutin, free of rutin isomers, and/or free of caffeine, rutin, and rutin isomers).

Step (B3-B5) of the methods described herein can achieve a composition of monocaffeoylquinic acids, dicaffeoylquinic acids, and salts thereof that has one or more off-taste compounds as described below in Table 2 at below the respective acceptable cutoff value for the off-taste compound.

The ion exchange stationary phase is non-limiting and can be any suitable ion exchange chromatography stationary phase. Examples of suitable ion exchange chromatography stationary phases include ANX-SEPHAROSE® fast flow resin, DEAE SEPHAROSE®, DEAE SEPHADEX® A25 resin, AMBERLITE® (FPA 53; FPA 55; CG-50 Type I; IRC-50; IRC-50S; and IRP-64), DIAION WA10, Sunresin T5, and DOWEX® CCR-3.

The ion exchange chromatography stationary phase can optionally be pre-conditioned with an aqueous composition (e.g., an aqueous composition comprising a (C1-C4)alkanol), such as an aqueous composition comprising from about 0% to about 40%, about 0% to about 30%, about 10% to about 40%, about 10% to about 30%, about 20% to about 40%, about 30% to about 40%, or about 35% by volume (C1-C4)alkanol, the balance being water, prior to the chromatographing of the adjusted initial extract or adjusted second initial extract. For example, the weak ion exchange chromatography column can be pre-conditioned with about 2 or more bed volumes (BV) at a flow rate of about 2 BV/h.

The pH of the weak ion exchange chromatography column can optionally be adjusted prior to the chromatographing of the adjusted initial extract or adjusted second initial extract. For example, the pH of the weak ion exchange chromatography column can be adjusted prior to the chromatographing with any suitable acid (e.g., hydrochloric acid) such that the pH of the weak ion exchange chromatography column (e.g., the pH of the resin/stationary phase) is a pH of less than about 10, about 9 or less, about 8 or less, about 7 or less, about 6 or less, about 5 or less, about 4 or less, about 3 or less; or a pH of about 2 to about 10, about 3 to about 8, about 5 to about 9, about 2 to about 6; about 3 to about 4; or about 3 to about 6. The pH of the weak ion exchange chromatography column can be adjusted before or after the column is optionally pre-conditioned with the aqueous composition comprising a (C1-C4) prior to the chromatographing of the adjusted initial extract or adjusted second initial extract.

After pre-conditioning and/or adjusting of the pH of the weak ion exchange chromatography column, the adjusted initial extract or adjusted second initial extract can be loaded onto the column at any suitable rate, such as at a rate of above 2 BV/h (bed volumes per hour). After loading the adjusted initial extract or adjusted second initial extract, the column can be washed with any suitable volume of an aqueous composition comprising a (C1-C4)alkanol (e.g., at least about 2 BV, at least about 3 BV or at least about 4 BV of an aqueous composition comprising from about 10% to about 40%, about 10% to about 30%, about 20% to about 40%, about 30% to about 40%, or about 35% by volume (C1-C4)alkanol, the balance being water) at any suitable rate, such as at a rate of about 2 BV/h. The volume of aqueous composition comprising a (C1-C4)alkanol can be discarded, as it will contain, among other things, caffeine, quercitrin, hyperoside, astragalin, avicularin, sophoricoside, rutin, and rutin isomers.

Step (B4) of the methods described herein involves eluting the stationary phase with a first elution composition to obtain a first eluent. This first eluting is performed under any conditions suitable to elute other compounds bound to the ion exchange resin but to not elute the at least one of monocaffeoylquinic acids and dicaffeoylquinic acids, and salts thereof adsorbed to the column.

An example of suitable conditions to elute these other compounds from the column include eluting the column with any suitable volume of a first eluent composition comprising about 10% to about 50%, about 20% to about 50%, or about 25% by volume (C1-C4)alkanol (e.g., at least about 2 BV, at least about 3 BV or at least about 4 BV). A suitable first eluent composition comprises 25% ethanol in water. The first eluent can be retained and may contain desirable compounds. For example, *Stevia* biomass processed by this method produces a first eluent comprising steviol glycosides.

Step (B5) of the methods described herein involves eluting the stationary phase with a second elution composition to obtain a second eluent. This second eluting is performed under any conditions suitable to elute the at least one of monocaffeoylquinic acids and dicaffeoylquinic acids, and salts thereof adsorbed to the column. An example of suitable conditions to elute the at least one of monocaffeoylquinic acids and dicaffeoylquinic acids, and salts thereof from the column include eluting the column with any suitable volume of a second eluent composition comprising an acid (e.g., hydrochloric acid, sulfuric acid, phosphoric acid, acetic acid, formic acid, and the like) at a suitable concentration (0.1-1.0%) and from about 50% to about 80%, about 60% to about 80%, or about 70% by volume (C1-C4)alkanol).

Step (B6) of the methods described herein involve processing the second eluent to remove solvent and/or to dry the composition to obtain a composition with at least one of monocaffeoylquinic acids and dicaffeoylquinic acids, and salts thereof. In one aspect, solvent removal can be accomplished under an inert atmosphere (e.g., under a nitrogen gas atmosphere).

Suitable conditions for removing solvent from the second eluent comprising the at least one of monocaffeoylquinic acids and dicaffeoylquinic acids, and salts thereof, to form a concentrate comprising the at least one of monocaffeoylquinic acids and dicaffeoylquinic acids, and salts thereof include blowing an inert gas (e.g., nitrogen gas) over the surface of the eluent. The eluent can be heated while blowing the nitrogen gas or it can be at room temperature (e.g., 25° C.). Other conditions for removing the solvent in the eluent include applying a vacuum to the container containing the eluent. The vacuum can be applied with the eluent at room temperature or while heating the container. Yet other conditions for removing solvent in the eluent include passing the eluent through a wiped film evaporator or an agitated thin film evaporator. The methods described herein can include drying in any suitable manner, including by lyophilization or spray drying.

Figure 4B:
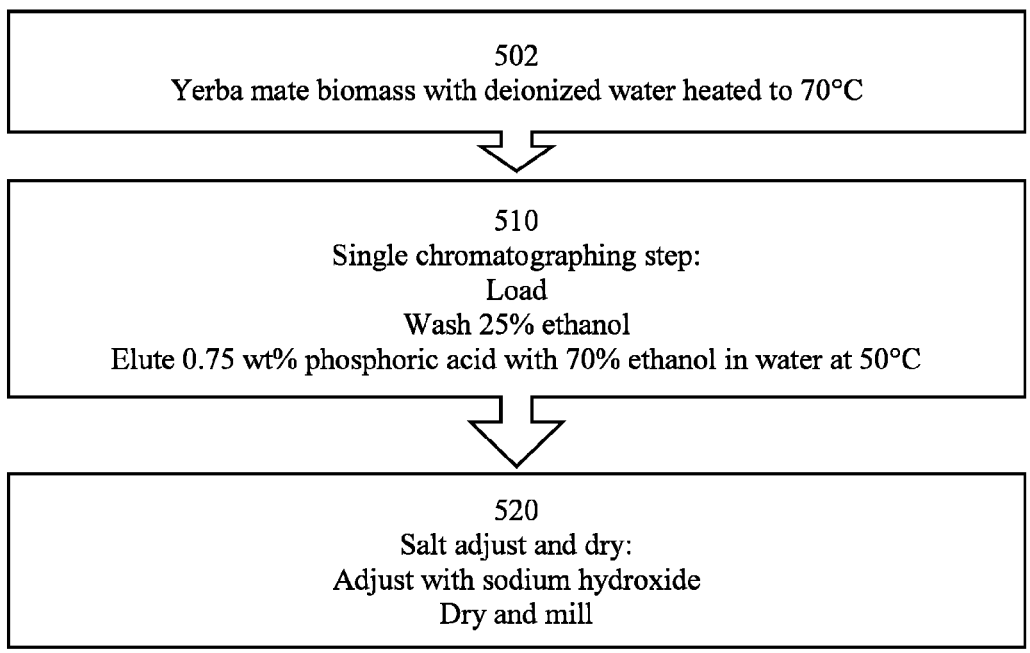
FIG. 4B is a flow diagram of another example of a method for making a composition comprising at least one of monocaffeoylquinic acids, and dicaffeoylquinic acids, and salts thereof from yerba mate biomass.

FIG. 4B is a flow diagram of a method 500 for making a composition comprising at least one of monocaffeoylquinic acids, and dicaffeoylquinic acids, and salts thereof from yerba mate biomass using a single chromatographing step. In operation 502, yerba mate biomass is contacted with deionized water that was heated to 70° C. via heat exchanger. The deionized water that is heated to 70° C. and applied to the bottom of a stainless steel column packed with yerba mate biomass at a flow rate of 2 BV per hour based on the volume of yerba mate biomass. An initial extract is collected from the top of the stainless steel column. The initial extract has a volume that is 10 times the volume of the yerba mate biomass. A 35 ml sample of the initial extract is collected for subsequent analysis. The initial extract is stored at 4° C.

In operation 510, the initial extract is processed with a single chromatographing step. The initial extract is applied to a weak anion exchange stationary phase (Sunresin T5 resin) at a rate of 2 BV per hour. A total amount of initial extract that is loaded is about 40 g caffeoylquinic acids and salt thereof per liter of resin. A 35 ml sample of the loading flow through is collected for analysis.

The stationary phase is then washed with 3 bed volumes of 25% ethanol in water at a 25° C. at a rate of 2 BV per hour. A 35 ml sample of the wash flow through is collected for analysis.

The stationary phase is then eluted with 6 bed volumes of elution composition comprising 0.75 wt % phosphoric acid with 70% ethanol in water. The elution composition is heated to 50° C. via heat exchanger before elution. The elution composition is applied at 1 BV per hour. The eluent is collected such that bed volumes 3, 4, and 5 are pooled and further processed. Bed volumes 1, 2, and 6 are pooled and can be reprocessed by the same process. A 35 ml sample of the pooled bed volumes 3, 4, and 5 is collected for analysis.

In operation 520, the pooled eluent is adjusted for salt content and processed to a dry powder. The caffeoylquinic acids and salts thereof content is calculated and then sodium hydroxide is added until about 70% of the pooled eluent is present as caffeoylquinic salts. The salt adjusted sample is then fed into an evaporator, heated to 40° C., and stripped of ethanol and water until a dissolved solids content of 5-10% DS is reached. The composition is then dried to DS>95% and milled to a fine powder.

Figure 4C:
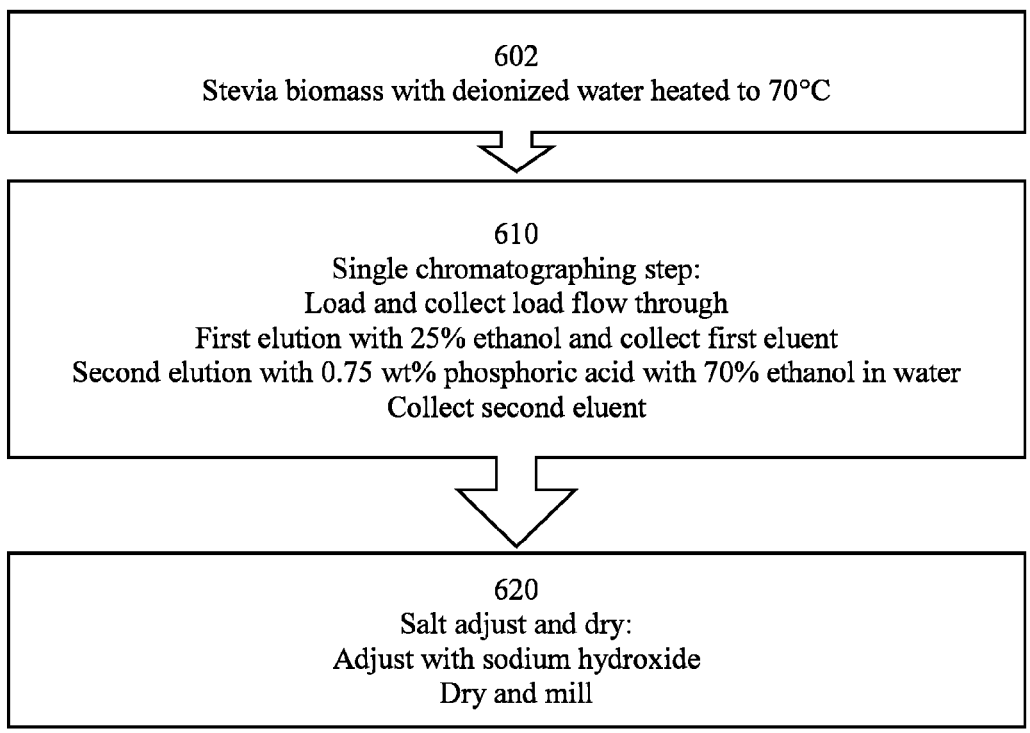
FIG. 4C is a flow diagram of another example of a method for making a composition comprising at least one of monocaffeoylquinic acids, and dicaffeoylquinic acids, and salts thereof from yerba mate biomass.

FIG. 4C is a flow diagram of a method 600 for making a composition comprising at least one of monocaffeoylquinic acids, and dicaffeoylquinic acids, and salts thereof from *Stevia* biomass using a single chromatographing step. Method 600 can also isolate a steviol glycoside composition from *Stevia* biomass. Method 600 can also isolate a separate steviol glycoside composition and a separate caffeoylquinic composition from a single batch of *Stevia* biomass. In operation 602, *Stevia* biomass is contacted with deionized water that was heated to 70° C. via heat exchanger. The deionized water that is heated to 70° C. and applied to the bottom of a stainless steel column packed with *Stevia* biomass at a flow rate of 2 BV per hour based on the volume of *Stevia* biomass. An initial extract is collected from the top of the stainless steel column. The initial extract has a volume that is 10 times the volume of the yerba mate biomass. A 35 mL sample of the initial extract is collected for subsequent analysis. The initial extract is stored at 4° C.

In operation 610, the initial extract is processed with a single chromatographing step. The initial extract is applied to a weak anion exchange stationary phase (Sunresin T5 resin) at a rate of 2 BV per hour. A total amount of initial extract that is loaded is about 40 g caffeoylquinic acids and salt thereof per liter of resin. The loading flow through is collected and pooled and contains steviol glycoside composition. A 35 mL sample of the loading flow through is collected for analysis.

The stationary phase is then eluted with 3 bed volumes of first elution composition (25% ethanol in water) at 25° C. at a rate of 2 BV per hour. This first eluent is collected and contains steviol glycosides. A 35 mL sample of the first eluent is collected for analysis.

The stationary phase is then eluted with 6 bed volumes of second elution composition comprising 0.75 wt % phosphoric acid with 70% ethanol in water. The second elution composition is heated to 40° C. via heat exchanger before elution. The elution composition is applied at 1 BV per hour. The eluent is collected such that bed volumes 3, 4, and 5 are pooled and further processed. Bed volumes 1, 2, and 6 are pooled and can be reprocessed by the same process. A 35 ml sample of the pooled bed volumes 3, 4, and 5 is collected for analysis.

In operation 620, the pooled second eluent is adjusted for salt content and processed to a dry powder. The caffeoylquinic acids and salts thereof content is calculated and then sodium hydroxide is added until about 70% of the second pooled eluent is present as caffeoylquinic salts. The salt adjusted sample is then fed into an evaporator, heated to 40° C., and stripped of ethanol and water until a dissolved solids content of 5-10% DS is reached. The composition is then dried to DS>95% and milled to a fine powder and a composition comprising at least one of monocaffeoylquinic acids, and dicaffeoylquinic acids, and salts thereof is obtained. Likewise, the loading flow through and the first eluent can be dried to obtain a steviol glycoside composition.

Compositions of Monocaffeoylquinic Acids, and Dicaffeoylquinic Acids, and Salts Thereof The composition comprising the at least one of monocaffeoylquinic acids, and dicaffeoylquinic acids, and salts thereof prepared according to the methods described herein can comprise substantially the same amounts by weight and/or substantially the same ratios by weight of caffeic acid, monocaffeoylquinic acids, and dicaffeoylquinic acids, and salts thereof relative to the yerba mate biomass.

The compositions comprising the at least one of monocaffeoylquinic acids, and dicaffeoylquinic acids, and salts thereof prepared according to the methods described herein can comprise a ratio by mass of total dicaffeoylquinic acids to total monocaffeoylquinic acids of about 1:1 to about 10:1 (e.g., from about 3:1 to about 10:1; about 3:2 to about 4:1; or about 3:1 to about 5:1). The compositions comprising the at least one of monocaffeoylquinic acids, dicaffeoylquinic acids, and salts thereof prepared according to the methods described herein can comprise a ratio by mass of total dicaffeoylquinic acids to total monocaffeoylquinic acids of from about 1:1 to about 0.01:1 (e.g., from about 0.5:1 to about 0.1:1).

The composition comprising the at least one of monocaffeoylquinic acids, dicaffeoylquinic acids, and salts thereof prepared according to the methods described herein can comprise a ratio by mass of each one of caffeic acid, monocaffeoylquinic acids, and dicaffeoylquinic acids, and salts thereof, of about 0.01 (e.g., about 0.005 to about 0.05) to about 1 (e.g., 0.5 to about 1.5) to about 1 (e.g., 0.5 to about 1.5), respectively.

In one aspect, the compositions comprising the at least one of monocaffeoylquinic acids, dicaffeoylquinic acids, and salts thereof as prepared according to the methods described herein preferably do not include off-taste compounds above a preferred content level. Table 2 shows off-taste compounds and preferred content levels for the respective off-taste compounds in the dried compositions comprising the at least one of monocaffeoylquinic acids, dicaffeoylquinic acids, and salts thereof. In one aspect, the composition comprising the at least one of monocaffeoylquinic acids, dicaffeoylquinic acids, and salts thereof does not include one or more of the compounds, or any combination thereof, at above the disclosed cutoff wt % as listed below in Table 2. In one aspect, the composition comprising monocaffeoylquinic acids, dicaffeoylquinic acids, and salts thereof as prepared by the methods including steps (B1-B6) does not include one or more of the compounds, or any combination thereof, at above the disclosed cutoff wt % as listed below in Table 2.

TABLE 2

| Class of compounds | Preferred Content Level (% wt) | % wt of compounds in solid (dry) compositions |
|---|---|---|
| Organic acids | <3%, preferably <2%, <1%, or 0% | malonate, malonic acid, oxalate, oxalic acid, lactate, lactic acid, succinate, succinic acid, malate, malic acid, citrate, citric acid |
| | <0.5%, preferably <0.25% or 0% | tartrate, tartaric acid, pyruvate, pyruvic acid, fumarate, fumaric acid, ascorbic acid, sorbate, sorbic acid, acetate, acetic acid |
| Inorganic acids | <1%, preferably <0.5% or 0% | sulfate, sulfuric acid, phosphate, phosphoric acid, nitrate, nitric acid, nitrite, nitrous acid, chloride, hydrochloric acid, ammonia, ammonium |
| Flavanoids, isoflavanoids, and neoflavanoids | <5%, preferably <4%, <3%, or <2%, more preferably <1%, <0.5%, or 0% | quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein |
| Flavanoid glycosides | <5%, preferably <4%, <3%, or <2%, more preferably <1%, <0.5%, or 0% | hesperidin, naringin, rutin, quercitrin, luteolin-glucoside, quercetin-xyloside |
| Anthocyanidins | <5%, preferably <4%, <3%, or <2%, more preferably <1%, <0.5%, or 0% | cyanidin, delphinidin, malvidin, pelargonidin, peonidin, petunidin |
| Tannins | <1%, preferably <0.5%, <0.25%, or 0% | tannic acid |
| Amino acids + total protein | <0.1%, preferably <0.05%, or 0% | alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1%, preferably <0.5%, <0.25%, or 0% | monoglycerides, diglycerides, triglycerides |
| Monosaccharides, disaccharides, and polysaccharides | <1% | glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose |
| Sugar alcohols | <1% | glycerol, sorbitol, mannitol, xylitol, maltitol, lactitol, erythritol, isomalt, inositol |
| Dietary fiber | <0.1%, preferably <0.05% or 0% | acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, psyllium husk mucilage, resistant starches, tara gum, tragacanth gum, xanthan gum, cellulose, chitin, and chitosan |

TABLE 2-continued

| Class of compounds | Preferred Content Level (% wt) | % wt of compounds in solid (dry) compositions |
|---|---|---|
| Saponins | <0.5% | glycosylated ursolic acid and glycosylated oleanolic acid |
| Terpenes | <0.5% | eugenol, geraniol, geranial, alpha-ionone, beta-ionone, epoxy-ionone, limonene, linalool, linalool oxide, nerol, damascenone |
| Lipid oxidation products | <0.5% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.01% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd(pyrene, Naphthalene, Phenanthrene, Pyrene |
| Steviol glycosides | <55% | stevioside; steviolbioside; rubusoside; 13- and 19-SMG; dulcosides A, B, C, D; and rebaudiosides A, B, C, D, E, F, I, M, N, O, T |
| Other compounds | <0.1%, preferably <0.05% or 0% | chlorophyll, furans, furan-containing chemicals, theobromine, theophylline, and trigonelline |

In one aspect, the compositions comprising the at least one of monocaffeoylquinic acids, dicaffeoylquinic acids, and salts thereof as prepared according to the methods described herein when dried comprises less than 3 wt % of a total of malonate, malonic acid, oxalate, oxalic acid, lactate, lactic acid, succinate, succinic acid, malate, malic acid, citrate, and citric acid in the composition.

In one aspect, the compositions comprising the at least one of monocaffeoylquinic acids, dicaffeoylquinic acids, and salts thereof as prepared according to the methods described herein when dried comprises less than when dried comprises less than 0.5 wt % of a total of tartrate, tartaric acid, pyruvate, pyruvic acid, fumarate, fumaric acid, ascorbic acid, sorbate, sorbic acid, acetate, and acetic acid in the composition.

In one aspect, the compositions comprising the at least one of monocaffeoylquinic acids, dicaffeoylquinic acids, and salts thereof as prepared according to the methods described herein when dried comprises less than when dried comprises less than 1 wt % of a total of sulfate, sulfuric acid, phosphate, phosphoric acid, nitrate, nitric acid, nitrite, nitrous acid, chloride, hydrochloric acid, ammonia, and ammonium in the composition.

In one aspect, the compositions comprising the at least one of monocaffeoylquinic acids, dicaffeoylquinic acids, and salts thereof as prepared according to the methods described herein when dried comprises less than 5 wt % of a total of flavonoids, isoflavanoids, and neoflavanoids(quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glyciteinin the composition.

In one aspect, the compositions comprising the at least one of monocaffeoylquinic acids, dicaffeoylquinic acids, and salts thereof as prepared according to the methods described herein when dried comprises less than 5 wt % of a total of hesperidin, naringin, rutin, quercitrin, luteolin-glucoside, and quercetin-xyloside in the composition.

In one aspect, the compositions comprising the at least one of monocaffeoylquinic acids, dicaffeoylquinic acids, and salts thereof as prepared according to the methods described herein when dried comprises less than 5 wt % of a total of cyanidin, delphinidin, malvidin, pelargonidin, peonidin, and petunidin in the composition.

In one aspect, the compositions comprising the at least one of monocaffeoylquinic acids, dicaffeoylquinic acids, and salts thereof as prepared according to the methods described herein when dried comprises less than 1 wt % of a total tannins and tannic acid in the composition.

In one aspect, the compositions comprising the at least one of monocaffeoylquinic acids, dicaffeoylquinic acids, and salts thereof as prepared according to the methods described herein when dried comprises less than 0.1 wt % of a total alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine in the composition.

In one aspect, the compositions comprising the at least one of monocaffeoylquinic acids, dicaffeoylquinic acids, and salts thereof as prepared according to the methods described herein when dried comprises less than 1 wt % of a total monoglycerides, diglycerides, and triglycerides in the composition.

In one aspect, the compositions comprising the at least one of monocaffeoylquinic acids, dicaffeoylquinic acids, and salts thereof as prepared according to the methods described herein when dried comprises less than 1 wt % of a total monosaccharides, disaccharides, polysaccharides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, and panosein the composition.

In one aspect, the compositions comprising the at least one of monocaffeoylquinic acids, dicaffeoylquinic acids, and salts thereof as prepared according to the methods described herein when dried comprises less than 1 wt % of a total of sugar alcohols, glycerol, sorbitol, mannitol, xylitol, maltitol, lactitol, erythritol, isomalt, and inositol in the composition.

In one aspect, the compositions comprising the at least one of monocaffeoylquinic acids, dicaffeoylquinic acids, and salts thereof as prepared according to the methods described herein when dried comprises less than 1 wt % of a total of dietary fiber, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *psyllium* husk mucilage, resistant starches, tara gum, tragacanth gum, xanthan gum, cellulose, chitin, and chitosan in the composition.

In one aspect, the compositions comprising the at least one of monocaffeoylquinic acids, dicaffeoylquinic acids, and salts thereof as prepared according to the methods described herein when dried comprises less than 0.1 wt % of a total of chlorophyll, furans, furan-containing chemicals, theobromine, theophylline, and trigonelline in the composition.

In one aspect, the compositions comprising the at least one of monocaffeoylquinic acids, dicaffeoylquinic acids, and salts thereof as prepared according to the methods described herein when dried comprises less than 1 wt % of a total of caffeine in the composition.

In one aspect, the compositions comprising the at least one of monocaffeoylquinic acids, dicaffeoylquinic acids, and salts thereof as prepared according to the methods described herein when dried comprises less than 1 wt % of a total of rutin in the composition.

In one aspect, the compositions comprising the at least one of monocaffeoylquinic acids, dicaffeoylquinic acids, and salts thereof as prepared according to the methods described herein when dried comprises less than 0.5 wt % of a total of glycosylated ursolic acid and glycosylated oleanolic acid in the composition.

In one aspect, the compositions comprising the at least one of monocaffeoylquinic acids, dicaffeoylquinic acids, and salts thereof as prepared according to the methods described herein when dried comprises less than 0.5 wt % of a total of volatile organic compounds, terpenes, eugenol, geraniol, geranial, alpha-ionone, beta-ionone, epoxy-ionone, limonene, linalool, linalool oxide, nerol, and damascenone in the composition.

In one aspect, the compositions comprising the at least one of monocaffeoylquinic acids, dicaffeoylquinic acids, and salts thereof as prepared according to the methods described herein when dried comprises less than 0.5 wt % of a total of fatty acid oxidation products, decanone, decenal, nonenal, octenal, heptenal, hexenal, pentenal, pentenol, pentenone, hexenone, hydroxynonenal, and malondialdehyde in the composition.

In one aspect, the compositions comprising the at least one of monocaffeoylquinic acids, dicaffeoylquinic acids, and salts thereof as prepared according to the methods described herein when dried comprises less than 0.01 wt % of a total of polycyclic aromatic hydrocarbons (PAHs) (acenaphthene, acenaphthylene, anthracene, benzo(a)anthracene, benzo(a)pyrene, benzo(b)fluoranthene, benzo(ghi)perylene, benzo(k)fluoranthene, chrysene, dibenzo(a,h)anthracene, fluoranthene, fluorene, indeno(1,2,3-cd)pyrene, naphthalene, phenanthrene, pyrene, and others) in the composition.

In one aspect, the compositions comprising the at least one of monocaffeoylquinic acids, dicaffeoylquinic acids, and salts thereof as prepared according to the methods described herein and when dried, have polycyclic aromatic hydrocarbons (PAHs)(acenaphthene, acenaphthylene, anthracene, benzo(a)anthracene, benzo(a)pyrene, benzo(b)fluoranthene, benzo(ghi)perylene, benzo(k)fluoranthene, chrysene, dibenzo(a,h)anthracene, fluoranthene, fluorene, indeno(1,2,3-cd)pyrene, naphthalene, phenanthrene, pyrene, and others) removed to below 0.01% by weight.

In one aspect, the compositions comprising the at least one of monocaffeoylquinic acids, dicaffeoylquinic acids, and salts thereof as prepared according to the methods described herein when dried comprise less than 0.5 wt % of a total of fatty acid oxidation products, nonenal, hexenal, hydroxynonenal, and malondialdehyde in the composition.

In one aspect, the compositions comprising the at least one of monocaffeoylquinic acids, dicaffeoylquinic acids, and salts thereof as prepared according to the methods described herein have color removed such that a % transmittance at 430 nm is >80%.

In one aspect, the compositions comprising the at least one of monocaffeoylquinic acids, dicaffeoylquinic acids, and salts thereof as prepared according to the methods described herein have color removed such that a b value is less than 4 on CIE L*a*b* color space.

In one aspect, the compositions comprising the at least one of monocaffeoylquinic acids, dicaffeoylquinic acids, and salts thereof as prepared according to the methods described herein have color removed such that a % transmittance at 430 nm is >80% without a decoloring and/or desalting step.

In one aspect, the compositions comprising the at least one of monocaffeoylquinic acids, dicaffeoylquinic acids, and salts thereof as prepared according to the methods described herein have color removed such that a b value is less than 4 on CIE L*a*b* color space without a decoloring and/or desalting step.

Ingestible Compositions

The composition comprising the at least one of monocaffeoylquinic acids, and dicaffeoylquinic acids, and salts thereof prepared according to the methods described herein can be incorporated into any ingestible composition, including into beverages and food products.

For example, the ingestible composition can be a comestible composition or noncomestible composition. By "comestible composition", it is meant any composition that can be consumed as food by humans or animals, including solids, gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical compositions, which refers to a noncomestible composition intended to be used by humans or animals for therapeutic purposes. By "animal", it includes any non-human animal, such as, for example, farm animals and pets.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

As used herein, the singular forms "a," "an," and "the" include plural referents unless the context clearly dictates otherwise. For example, reference to "a steviol glycoside" means one or more steviol glycosides.

EXAMPLES

The following examples are provided to illustrate the disclosure, but are not intended to limit the scope thereof. All parts and percentages are by weight unless otherwise indicated.

Example 1

Materials and Methods

A yerba mate biomass that can be used is a commercially-available product sold as ECOTEAS™ Yerba Mate Unsmoked Leaf and Stem Traditional Cut, which is yerba mate tea grown in the state of Misiones in northeastern Argentina. The biomass is obtained already comminuted. A portion of the comminuted yerba mate biomass (300 g) was suspended in 50% ethanol/water (1.5 L) in glass jar and was shaken for 1 hour. After shaking, the resulting mixture was filtered using a ceramic Büchner funnel with Whatman 54 low ash filter paper into glass 4 L side arm flask. The filtered material was diluted to 35% ethanol using water. Upon dilution, some unwanted material precipitates, as it is not soluble at 35% by volume ethanol. The diluted material was therefore re-filtered using a ceramic Büchner funnel with Whatman 44 low ash filter paper into glass 4 L side arm flask.

AMBERLITE® FPA 53 resin in a glass column was prepared for ion exchange chromatography by treating the resin with aqueous hydrochloric acid to protonate amines in the resin. Chloride is then washed off until the pH is greater than 4 with approximately 10 BV of water. The resin is then pre-conditioned with 35% ethanol in water (2 BV at 2 BV/h) prior to loading. The re-filtered material was loaded onto the resin. The loading permeate was discarded. The resin was then washed with 35% ethanol in water (4 BV at 2 BV/h). The permeate was discarded. The resin was then eluted with 50% ethanol in water, comprising 10% FCC sodium chloride (4 BV, 0.5 BV/h). This last permeate was taken to the next step, where the solvent was removed slowly by blowing nitrogen gas over top of the permeate for two days, until volume was approximately ⅓ of initial volume and/or the ethanol concentration was <1% of the solution. The temperature was kept at ambient (about 25° C.) temperature or below, as high temperatures, high oxygen content, and/or high exposure to light can degrade the compounds of interest. If such care is not taken, the compounds will polymerize to form highly colored, hydrophobic polymers, some of the largest of which are insoluble in water.

The concentrated material was filtered through Whatman 44 filter paper on a Büchner funnel followed by filtering through an 0.2 μm polyethersulfone filter. The filtered material was decolored using a 3 kDa molecular weight cutoff membrane TURBOCLEAN® NP010, keeping the permeate, although a GE Osmonic Sepa CF TF (thin film) UF GK membrane can be used. The decolored material will degrade/polymerize over time and can degrade due to oxidation processes, and this will re-introduce color into the system. It is therefore advisable to desalt and dry shortly after decoloring, such as within one to two days. The decolored material was then filtered through a TRISEP® XN45 nanofiltration membrane to desalt. The desalted material was freeze-dried using LABCONCO™ FAST-FREEZE™ 600 mL flasks.

The freeze-dried material was characterized using UHPLC-UV analysis using a C18-based reversed-phase column. The mobile phase A consists of 0.025% TFA in water and mobile phase B is acetonitrile. After an initial hold at 5% B, the compounds are eluted at elevated temperature by a gradient from 5% B to 25% B from 1.2 to 15 minutes at a flow rate of 0.4 mL/min. The column is then washed with 100% acetonitrile and re-equilibrated. The UV detector is set to record data at 210 and 324 nm.

Figure 5:
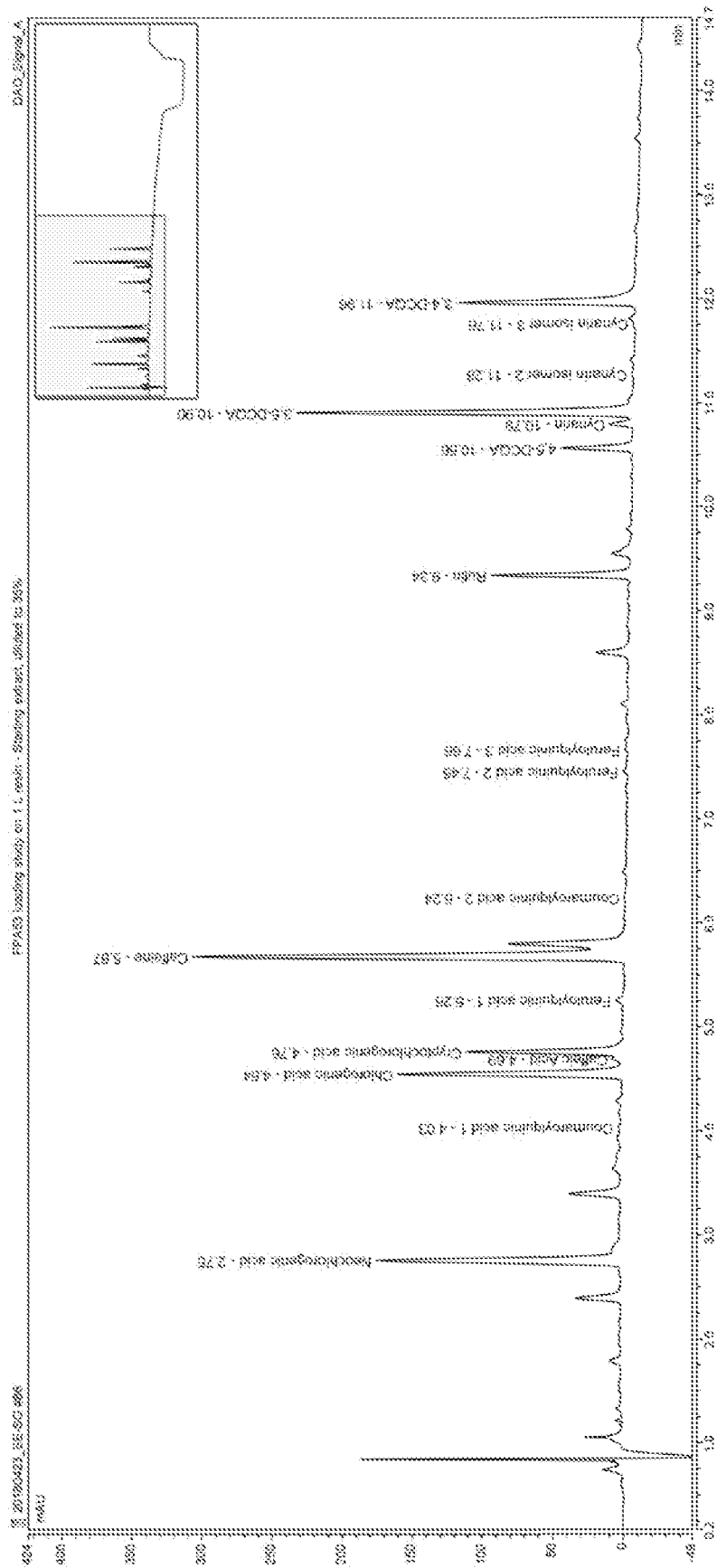
FIGS. 5-7 are UHPLC-UV chromatograms of an initial yerba mate extract, a concentrate obtained following chromatographing the adjusted second initial extract on an ion exchange chromatography stationary phase; and after drying, following the process described in steps (a)-(h), described herein, where "DCQA" refers to "dicaffeoylquinic acid."
Figure 6:
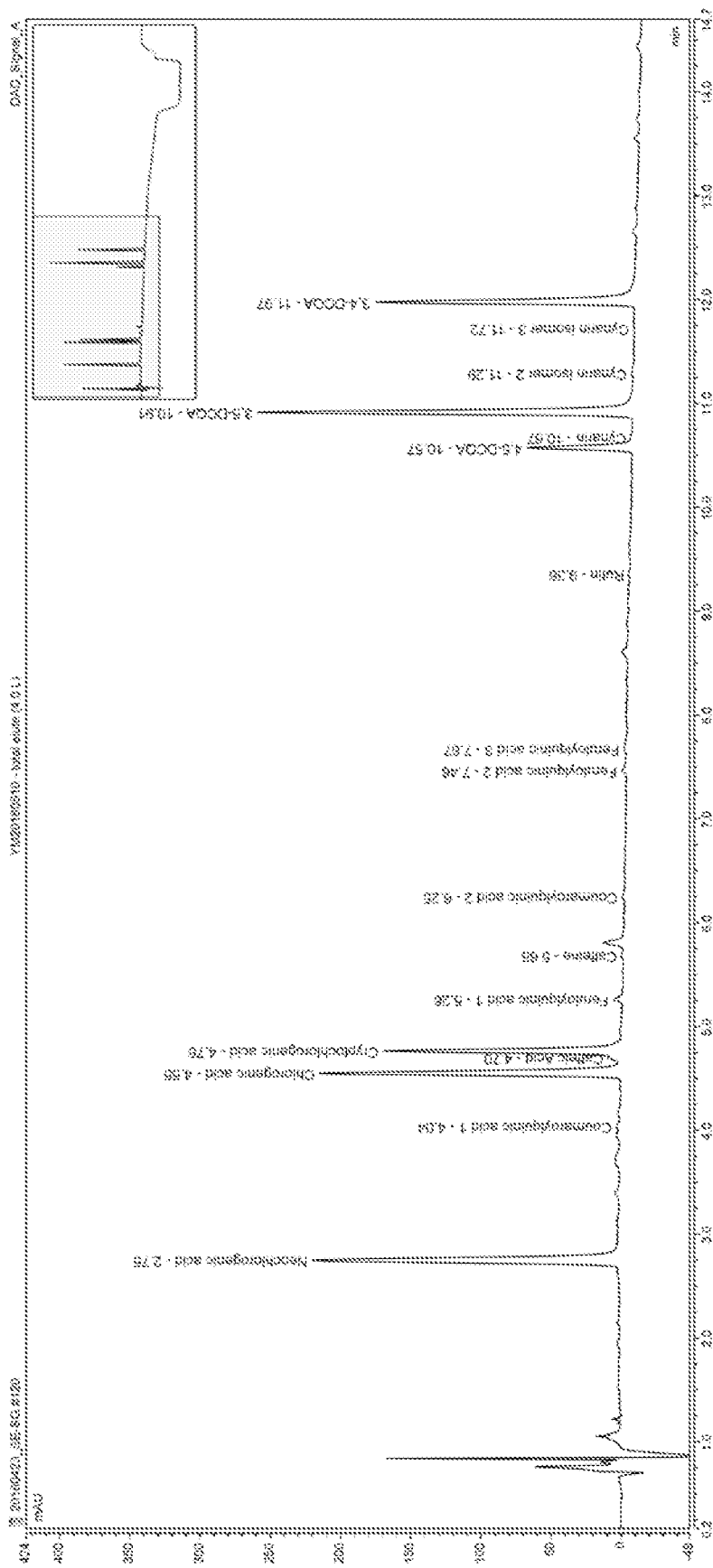
Figure 7:
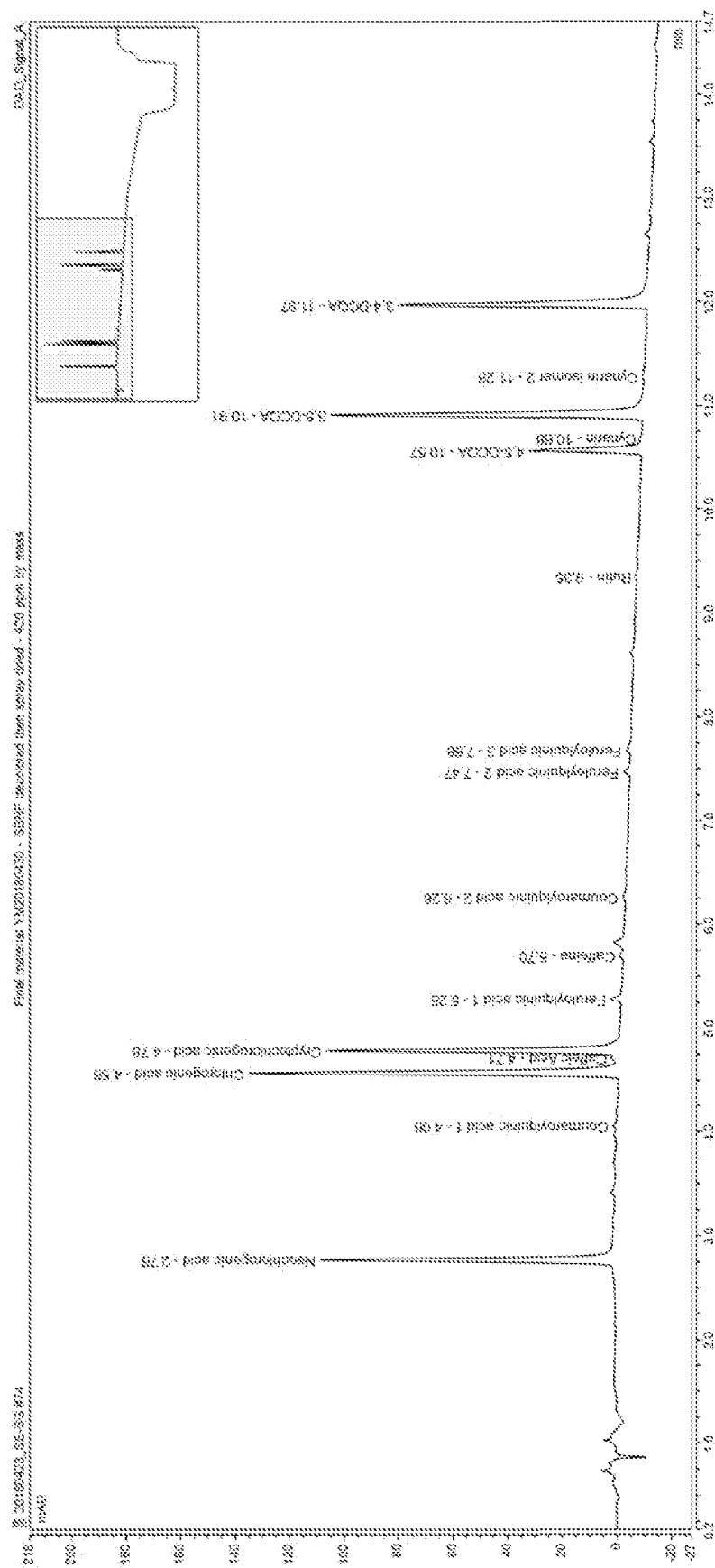

FIGS. 5-7 are UHPLC-UV chromatograms of an initial yerba mate extract, a concentrate obtained following chromatographing the adjusted second initial extract on an ion exchange chromatography stationary phase; and after drying, following the process described in steps (a)-(h), where "DCQA" refers to "dicaffeoylquinic acid." FIG. 5 shows that the initial yerba mate extract contains caffeine and rutin, in addition to the compounds of interest, including chlorogenic acid, neochlorogenic acid, cryptochlorogenic acid, caffeic acid, and the various isomers of dicaffeoylquinic acids, including 3,4-DCQA and 3,5-DCQA. As described herein, and as shown in FIG. 6, the chromatographing removes a large amount of the caffeine and rutin present in the initial yerba mate extract. The peaks at a retention time of approximately 5.67 minutes, corresponding to caffeine, and at approximately 9.36 minutes, corresponding to rutin, present in FIG. 5 are absent in FIG. 6. The same holds true in FIG. 7. It is worth noting that the relative intensities of the peaks for neochlorogenic acid, chlorogenic acid, caffeic acid, cryptochlorogenic acid, and the various isomers of dicaffeoylquinic acid are persevered, thus lending credence to the fact that the compositions obtained using the methods described herein comprises substantially the same amounts by weight or substantially the same ratios by weight of caffeic acid, monocaffeoylquinic acids, and dicaffeoylquinic acids, and salts thereof relative to the yerba mate biomass.

FIGS. 8-10 are tables showing, in tabular form, the peak name, retention time, and relative area percent data for the UHPLC-UV chromatographs shown in FIGS. 5-7, respectively.

Example 2

Stevia Extraction

Stevia biomass was used to prepare a caffeoylquinic (CQA) composition comprising at least one of mono-caffeoylquinic acids, dicaffeoylquinic acids, and salts thereof. Stevia biomass was obtained in the form of dry Stevia leaf. The dry Stevia leaf biomass was extracted using 50% ethanol (v/v) in ultrapure water for 1 hour of contact time to obtain an initial extract. The total mass of the initial extract was 10 times the mass of the Stevia leaf biomass. The initial extract was filtered with a 20 μm filter and the retained solids were washed with an amount of the 50% ethanol extraction composition that was about 5 times the amount of the Stevia leaf biomass.

The initial extract contained significant chlorophyll and other hydrophobic components. An ethyl acetate extraction was carried out to reduce the levels of chlorophyll and other hydrophobic components. The initial extract was transferred to a glass container and an equal volume of ultrapure water was added followed by the same volume of ethyl acetate. The glass container was shaken and liquid phases allowed to separate. The ethyl acetate was remove and an additional volume of ethyl acetate was added. The glass container was shaken again and liquid phases allowed to separate. The ethyl acetate was removed and the remaining aqueous fraction was retained. The remaining aqueous fraction was acidified with $H_2SO_4$ to convert the caffeoylquinics from salt form to acid form. Another volume of ethyl acetate was added, the container shaken, and liquid phases allowed to separate. Because the caffeoylquinics were now present in the ethyl acetate fraction, this first ethyl acetate fraction was retained and further processed. Optionally, a second round of ethyl acetate extraction can increase yields of CQAs to obtain a second ethyl acetate fraction that can be combined with the first ethyl acetate fraction. The ethyl acetate fraction was dried under nitrogen for >24 hours and the compounds were reconstituted in water to obtain a reconstituted fraction.

Ion Exchange Chromatography

A weak anion exchange resin, Dowex 66, served as the ion exchange stationary phase. The resin was packed into a column and regenerated before use in the following manner: the resin was suspended in water to form a slurry and the slurry loaded into a column until the bed volume reached the desired amount. To remove potential voids within the resin and to prevent channeling, 2 bed volumes of deionized water were run through the column from the bottom to the top at a rate of 4 bed volumes per hour. A solution of 7% HCl and 50% ethanol in water (v/v) equal to 4 times the bed volume was prepared and pumped into the column from the top to the bottom. The column was subsequently rinsed with deionized water at a rate of 4 bed volumes per hour until the output of the column reached a pH>4.

The reconstituted fraction was loaded onto the prepared ion exchange column and the column was washed. The column was loaded at 25° C. at a rate of 2 bed volumes per hour. The column was then washed with a 3 bed volume solution of 50% ethanol in water (v/v), at a temperature of 25° C. and at a rate of 2 bed volumes per hour.

The resin was eluted using a solvent solution containing a high concentration of salt. An elution composition containing 50% ethanol (v/v) and 10% (w/w) sodium chloride in water was used to elute the resin. The resin was eluted with 4 bed volumes of the elution composition solution at a rate of 2 bed volumes per hour. The eluent was collected. The resin was then regenerated using the HCl/ethanol method described above.

Evaporation and Desalting Resin

The eluent was evaporated with nitrogen gas to remove organic solvent. A hydrophobic resin, Diaion SP70, was packed and washed with 95% ethanol (v/v) before use. The hydrophobic resin was then washed with 4 bed volumes of water at a rate of 4 bed volumes per hour. The eluent was loaded onto the hydrophobic resin and washed with 2 bed volumes of 10% ethanol in water (v/v) containing 0.1% HCl at a flow rate of 2 bed volumes per hour. The hydrophobic resin was washed with 2 bed volumes of pure water at 2 bed volumes per hour. The hydrophobic resin was eluted with 4 bed volumes of 70% ethanol in water (v/v) and the desalted eluent was dried under nitrogen to remove the ethanol to obtain a desalted fraction. The desalted fraction was adjusted with sodium hydroxide until the pH was >3.0 but <4.0 to (corresponding to a salt fraction of approximately 50%-80%) to obtain the caffeoylquinic (CQA) composition. The caffeoylquinic (CQA) composition was flash-frozen in a dry ice/isopropanol bath and lyophilized to result in the final powder.

Example 3

Yerba Mate Extraction

Yerba mate biomass was used to prepare a caffeoylquinic (CQA) composition comprising at least one of mono-caffeoylquinic acids, dicaffeoylquinic acids, and salts thereof using a single chromatographing step. Yerba mate biomass was obtained in the form of dry yerba mate loose leaf tea. A stainless steel column was packed with the yerba mate biomass. Deionized water that was heated to 70° C. via heat exchanger an applied to the bottom of the stainless steel column. The heated deionized water was applied at a flow rate of 2 BV per hour based on the volume of yerba mate biomass. An initial extract was collected from the top port of the stainless steel column. The initial extract had a volume that was 10 times the volume of the yerba mate biomass. A 35 ml sample of the initial extract was collected for subsequent analysis. The initial extract was stored at 4° C.

A weak anion exchange resin, Sunresin T5, served as the stationary phase and was packed into a column and regenerated before use. The resin was suspended in deionized water to form a slurry which was then loaded into the column until the bed volume reached the desired amount. To remove potential voids within the resin and to prevent channeling, 2 bed volumes of deionized water were run through the column from the bottom to the top at a rate of 4 bed volumes per hour. A solution of 46.7% (v/v) of 15% HCl (w/w) and 50% ethanol (v/v) in water equal to 4 times the bed volume was prepared and applied to the column at the top port of the column. The column was subsequently rinsed with deionized water at a rate of 4 bed volumes per hour until the output of the column reached a pH>4. Additional deionized water, at an increased flow rate of 8 bed volumes per hour, was run through the column to further pack the column.

The initial extract was processed with a single chromatographing step. The initial extract was applied the packed column at a rate of 2 BV per hour. A total amount of initial extract that was loaded was about 33 g caffeoylquinic acids and salt thereof per liter of resin. A 35 mL sample of the loading flow through was collected for analysis.

The column was then washed with 3 bed volumes of 25% ethanol in water at a 25° C. at a rate of 2 BV per hour. A 35 mL sample of the wash flow through was collected for analysis.

The column was then eluted with 6 bed volumes of elution composition containing 70% ethanol (v/v) and 0.88% (v/v) of 85 wt. % phosphoric acid in water. The elution composition was heated to 50° C. via heat exchanger before elution. The elution composition was applied at 1 BV per hour. The eluent was collected such that bed volumes 3, 4, and 5 are pooled and further processed. Bed volumes 1, 2, and 6 were pooled and can be reprocessed. A 35 mL sample of the pooled bed volumes 3, 4, and 5 was collected for analysis. The resin was then regenerated using the method described above.

pH Adjustment and Drying

The pooled eluent was adjusted for salt content and processed to a dry powder. The caffeoylquinic acids and salts thereof content was calculated and then sodium hydroxide was added until about 70% of the pooled eluent was present as caffeoylquinic salts. The salt adjusted sample was then fed into an evaporator, heated to 40° C., and stripped of ethanol and water until a dissolved solids content of 5-10% DS was achieved. The composition was then dried to DS>95% and milled to a fine powder.

Example 4

Stevia Extraction

Stevia biomass was used to prepare a caffeoylquinic (CQA) composition comprising at least one of monocaffeoylquinic acids, dicaffeoylquinic acids, and salts thereof using a single chromatographing step. Stevia biomass was obtained in the form of dried Stevia leaf (Stevia One, Peru). A stainless steel column was packed with the Stevia leaf biomass. Deionized water that was heated to 70° C. via heat exchanger an applied to the bottom of the stainless steel column. The heated deionized water was applied at a flow rate of 2 BV per hour based on the volume of Stevia leaf biomass. An initial extract was collected from the top port of the stainless steel column. The initial extract had a volume that was 10 times the volume of the Stevia leaf biomass. A 35 mL sample of the initial extract was collected for subsequent analysis. The initial extract was stored at 4° C.

A weak anion exchange resin, Sunresin T5, served as the stationary phase and was packed into a column and regenerated before use. The resin was suspended in deionized water to form a slurry which was then loaded into the column until the bed volume reached the desired amount. To remove potential voids within the resin and to prevent channeling, 2 bed volumes of deionized water were run through the column from the bottom to the top at a rate of 4 bed volumes per hour. A solution of 46.7% (v/v) of 15% HCl (w/w) and 50% ethanol (v/v) in water equal to 4 times the bed volume was prepared and applied to the column at the top port of the column. The column was subsequently rinsed with deionized water at a rate of 4 bed volumes per hour until the output of the column reached a pH>4. Additional deionized water, at an increased flow rate of 8 bed volumes per hour, was run through the column to further pack the column.

The initial extract was processed with a single chromatographing step. The initial extract was applied the packed column at a rate of 2 BV per hour. A total amount of initial extract that was loaded was about 33 g caffeoylquinic acids and salt thereof per liter of resin. A 35 mL sample of the loading flow through was collected for analysis.

The column was then washed with 3 bed volumes of 25% ethanol in water at a 25° C. at a rate of 2 BV per hour. A 35 mL sample of the wash flow through was collected for analysis.

The column was then eluted with 6 bed volumes of elution composition containing 70% ethanol (v/v) and 0.88% (v/v) of 85 wt. % phosphoric acid in water. The elution composition was heated to 40° C. via heat exchanger before elution. The elution composition was applied at 1 BV per hour. The eluent was collected such that bed volumes 3, 4, and 5 are pooled and further processed. Bed volumes 1, 2, and 6 were pooled and can be reprocessed. A 35 mL sample of the pooled bed volumes 3, 4, and 5 was collected for analysis. The resin was then regenerated using the method described above.

pH Adjustment and Drying

The pooled eluent was adjusted for salt content and processed to a dry powder. The caffeoylquinic acids and salts thereof content was calculated and then sodium hydroxide was added until about 70% of the pooled eluent was present as caffeoylquinic salts. The salt adjusted sample was then fed into an evaporator, heated to 40° C., and stripped of ethanol and water until a dissolved solids content of 5-10% DS was achieved. The composition was then dried to DS>95% and milled to a fine powder.

Figure 11:
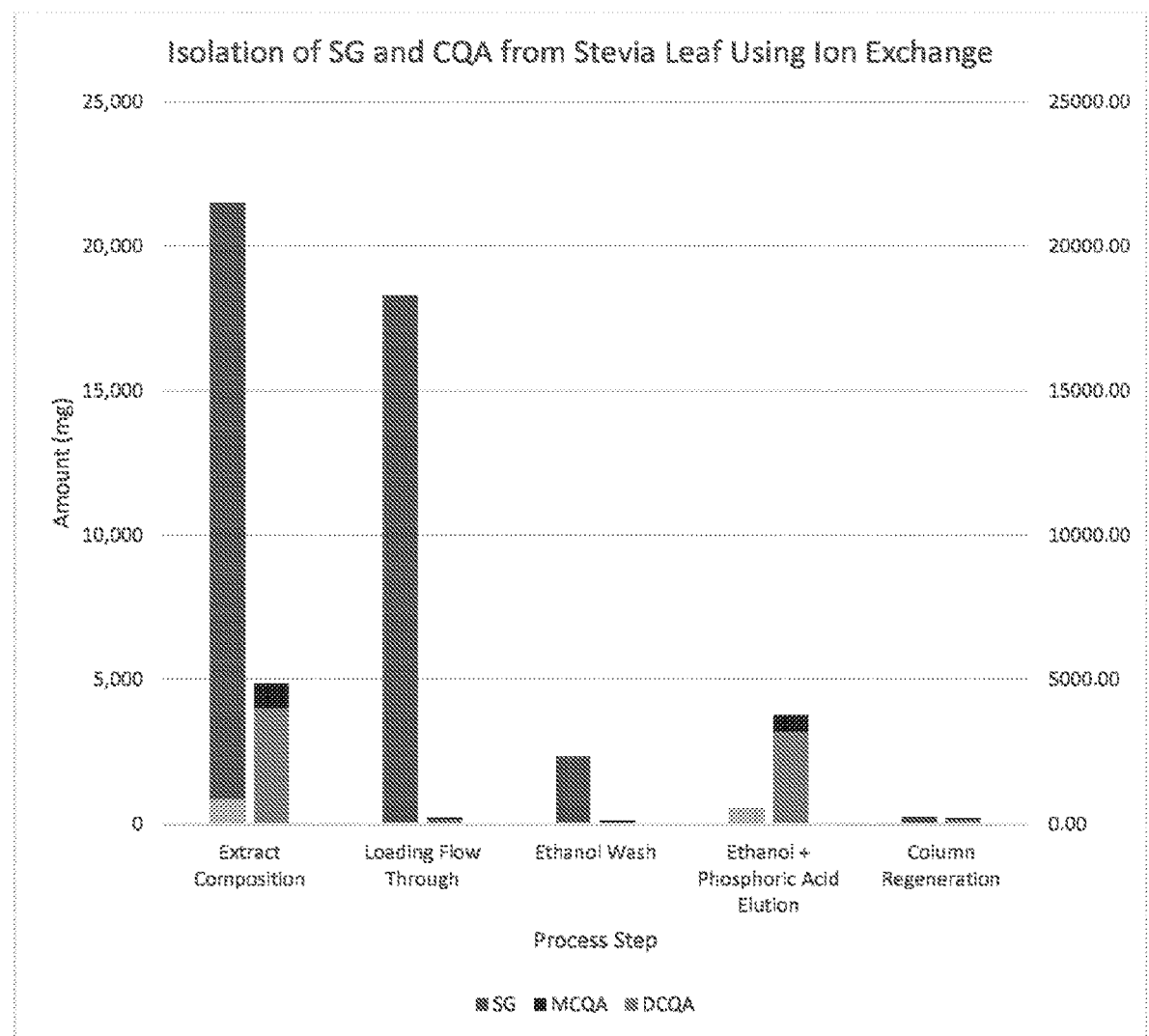
FIG. 11 shows a preparation of *Stevia* biomass. Amounts of steviol glycosides and caffeoylquinic acids in initial extract, in load flow through, wash (first elution), second elution, and column regeneration are shown.

Samples collected during the processing were submitted for UHPLC-UV analysis. A total of six caffeoylquinic acids (CQAs) and seven steviol glycosides (SGs) were quantified. Results indicated the CQAs were able to be isolated from the SGs using this processing method (See FIG. 11). The majority of the SGs were contained in the loading flow through and ethanol wash steps (87% and 11% of total, respectively). This was in contrast to the CQAs, where 80% of the mono-substituted CQAs (MCQAs) and 89% of the di-substituted CQAs (DCQAs) were contained within the elution effluent. The initial extract loaded onto the ion exchange column contained a 4:1 ratio of SGs to CQAs (21.5 g SGs, 4.9 g CQAs), whereas the elution effluent contained a 1:38 ratio of SGs to CQAs (0.1 g SGs, 3.8 g CQAs). These results indicate that a single chromatographing method can be used to provide a dual purification scheme to simultaneously isolate both CQAs and SGs from a single batch of Stevia leaf biomass.

Example 5

Compositions comprising monocaffeoylquinic acids, dicaffeoylquinic acids, and salts thereof prepared by the methods described above were analyzed to assess remaining color in the compositions. Four lots were prepared using yerba mate biomass and were analyzed for color. A sample of the initial extract was also analyzed. The 4 lots were analyzed with a HunterLab Vista spectrophotometer to record the L a* b* values of each lot. If this instrument is not available, a spectrophotometer can be used to measure the transmittance of the sample at 430 nm.

Briefly, a solution of 1% (wt/wt) glacial acetic acid was prepared in ultrapure water to a pH of about 4. An aliquot from each lot was used to prepare individual test samples in the 1% (wt/wt) glacial acetic acid solution. The test samples were prepared to a final concentration of 1.0 mg/ml of total monocaffeoylquinic acids, dicaffeoylquinic acids, and salts thereof. A control sample was prepared with only the 1% (wt/wt) glacial acetic acid solution. The L a* b* values for each test sample was measured using the HunterLab Vista spectrophotometer. Acceptable cutoff values were <3.5 for the b* value (or a transmittance of >85% at 430 nm).

Lots 1, 2, and 4 were prepared with ion exchange chromatography, desalting with hydrophobic column, and decoloring with membrane filtration. Lot 3 was prepared with the methods described above in steps (B1-B6) and Example 3. The sample with the initial extract served as a reference. The b* values for the test samples and control are shown below in Table 3.

TABLE 3

| Lot | b* value | Transmittance at 430 nm |
|---|---|---|
| Lot #1 - good color removal | 1.93 | 95.4% |
| Lot #2 - acceptable color removal | 2.77 | 92.9% |
| Lot #3 - acceptable color removal | 2.87 | 93.1% |
| Lot #4 - poor color removal | 4.37 | 89.2% |
| Initial crude hot-water extract of yerba mate | 17.13 | 40.7% |

Lots 1, 2, and 4 showed acceptable removal of color as evidenced by b* values below the cutoff value of 3.5. Lot 3 also showed acceptable removal of color as evidence by a b* value of 2.87 (below the 3.5 cutoff value). Therefore, surprisingly, the sample corresponding to the methods described above in steps (B1-B6) and Example 3 showed acceptable removal of color even though only a single chromatographing step was used and separate desalting and decoloring steps were not used.

Example 6

Compositions comprising monocaffeoylquinic acids, dicaffeoylquinic acids, and salts thereof prepared by the methods described above were analyzed to assess the presence of polycyclic aromatic hydrocarbons. Liquid chromatography with fluorescence detection was utilized to analyze the presence of polycyclic aromatic hydrocarbons. Methodology was similar to that reported in EPA method 610 for the analysis of PAH content in drinking water. Samples were extracted into acetonitrile, filtered through a 0.2 μm PTFE filter, and injected without further cleanup. The raw material and final product were prepared such that the total CQA content was equivalent between them. An additional sample was prepared the same way containing only the acetonitrile diluent. The results in Table 4 show that the fluorescent material present in the initial leaf is completely removed from the final product such that it is comparable to the blank.

TABLE 4

| Sample | Fluorescent signal (Area LU*min) |
|---|---|
| Control | 0.0415 |
| Dry leaf material | 1.7897 |
| Caffeoylquinic composition from Yerba mate | 0.0554 |

Example 7

Compositions comprising monocaffeoylquinic acids, dicaffeoylquinic acids, and salts thereof prepared by the methods described above were analyzed to assess the presence of saponins. Table 5 below shows saponin compounds that were assayed and their corresponding masses.

TABLE 5

| Compound | Molecular Formula | [M − H]−, [M − H + COOH]2− |
|---|---|---|
| Oleanolic acid or Ursolic acid + 3Glc | $C_{48}H_{78}O_{18}$ | 941.5115, 493.2549 |
| Oleanolic acid or Ursolic acid + 4Glc | $C_{54}H_{88}O_{23}$ | 1103.5644, 574.2813 |
| Oleanolic acid or Ursolic acid + 5Glc | $C_{60}H_{98}O_{28}$ | 1265.6172, 655.3077 |
| Oleanolic acid or Ursolic acid + 6Glc | $C_{66}H_{108}O_{33}$ | 1427.6700, 736.3341 |
| Oleanolic acid or Ursolic acid + 7Glc | $C_{72}H_{118}O_{38}$ | 1589.7228, 817.3605 |

A composition was prepared from yerba mate biomass using the methods described above in steps (B1-B6) and Example 3. Aliquots were taken throughout the process. Samples as described in below in Table 6 were prepared by dilution in 55% methanol/water. The samples were injected onto a high-resolution Orbitrap mass spectrometer collecting full-scan data at 70,000 mass resolution. The exact masses of the saponins were extracted and the area counts are reported in Table 6.

TABLE 6

| Sample | Mass spec area of saponins (combined all masses) |
|---|---|
| Ion Exchange (Sunresin T5) - Initial extract load | 629522 |
| Ion Exchange (Sunresin T5) - Flow through from initial extract load | 336187 |
| Ion Exchange (Sunresin T5) - 25% ethanol wash (first eluent) | 384019 |
| Ion Exchange (Sunresin T5) - 1st bed volume of second elution | 104333 |
| Ion Exchange (Sunresin T5) - 2nd bed volume of second elution | 16100 |
| Ion Exchange (Sunresin T5) - 3rd bed volume of second elution | Not Detected |
| Ion Exchange (Sunresin T5) - 4th bed volume of second elution | 784 |
| Ion Exchange (Sunresin T5) - 5th bed volume of second elution | Not Detected |

The present invention provides for the following embodiments, the numbering of which is not to be construed as designating levels of importance:

EMBODIMENTS

1. A method for making a caffeoylquinic composition, the method comprising:
   contacting biomass with a first aqueous composition to obtain an initial extract;
   chromatographing the initial extract on an ion exchange stationary phase;
   eluting the stationary phase with a first aqueous elution composition to obtain a first eluent; and
   eluting the stationary phase with a second aqueous elution composition to obtain a second eluent,
   wherein the second eluent comprises one or more of monocaffeoylquinic acid, dicaffeoylquinic acid, and salts of the foregoing.

2. The method of embodiment 1, wherein the biomass is selected from the group consisting of yerba mate, *Stevia*, and globe artichoke.

3. The method of embodiment 1, wherein the biomass is comminuted.

4. The method of embodiment 1, further comprising removing solids from the initial extract before chromatographing.

5. The method of embodiment 1, further comprising filtering the initial extract before chromatographing.

6. The method of embodiment 1, wherein monocaffeoylquinic acid comprises one or more of 3-O-caffeoylquinic acid, 4-O-caffeoylquinic acid, and 5-O-caffeoylquinic acid.

7. The method of embodiment 1, wherein dicaffeoylquinic acid comprises one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

8. The method of embodiment 1, wherein the stationary phase is weak anion exchange stationary phase.

9. The method of embodiment 1, wherein the first aqueous composition is water.

10. The method of embodiment 1, wherein the first aqueous composition is heated to 50-70° C. before contacting with the biomass.

11. The method of embodiment 1, wherein the initial extract is contacted with the stationary phase at 20-25° C.

12. The method of embodiment 1, wherein the initial extract is contacted with the stationary phase at 1-2 bed volumes per hour.

13. The method of embodiment 1, wherein the initial extract is contacted with the stationary phase at a ratio of up to 40 g caffeoylquinic composition per liter of resin.

14. The method of embodiment 1, wherein the initial extract is contacted with the stationary phase and the stationary phase is washed with the first aqueous composition to obtain a first wash composition.

15. The method of embodiment 1, wherein the first aqueous elution composition comprises 1-40% (C1-C4)alkanol.

16. The method of embodiment 1, wherein the first aqueous elution composition comprises 20-30% (C1-C4)alkanol.

17. The method of embodiment 1, wherein (CT-C4)alkanol is ethanol.

18. The method of embodiment 1, wherein the first aqueous elution composition comprises 25% ethanol.

19. The method of embodiment 1, wherein the stationary phase is eluted with at least 3 bed volumes of the first aqueous elution composition.

20. The method of embodiment 1, wherein the stationary phase is eluted at 20-25° C. with the first aqueous elution composition.

21. The method of embodiment 1, wherein the stationary phase is eluted at a rate of 1-2 bed volumes per hour with the first aqueous elution composition.

22. The method of embodiment 1, wherein the second aqueous elution composition comprises 50-80% (C1-C4) alkanol.

23. The method of embodiment 1, wherein the second aqueous elution composition comprises 50-80% ethanol.

24. The method of embodiment 1, wherein the second aqueous elution composition comprises 70% ethanol.

25. The method of embodiment 1, wherein the second aqueous elution composition comprises 1-10% salt.

26. The method of embodiment 1, wherein the second aqueous elution composition comprises sodium chloride.

27. The method of embodiment 1, wherein the second aqueous elution composition is acidified.

28. The method of embodiment 1, wherein the second aqueous elution composition is acidified with phosphoric acid.

29. The method of embodiment 1, wherein the second aqueous elution composition is acidified with 0.5-1.0% phosphoric acid.

30. The method of embodiment 1, wherein the stationary phase is eluted with at least 2 bed volumes of the second aqueous elution composition.

31. The method of embodiment 1, wherein the stationary phase is eluted at a rate of 1 bed volumes per hour with the first aqueous elution composition.

32. The method of embodiment 1, wherein the second aqueous elution composition is heated to 40-50° C. before eluting the stationary phase.

33. The method of embodiment 1, wherein the second eluent has a ratio by mass of monocaffeoylquinic acid and salts thereof to dicaffeoylquinic acid and salts thereof, of about 0.01 to about 1 to about 1.

34. The method of embodiment 1, further comprising a decoloring step.

35. The method of embodiment 1, further comprising a desalting step.

36. The method of embodiment 1, further comprising chromatographing the second eluent with a hydrophobic resin stationary phase to desalt the second eluent.

37. The method of embodiment 1, further comprising a drying the first eluent.

38. The method of embodiment 1, further comprising a drying the second eluent.

39. The method of any one of embodiments 1-38, wherein the biomass is yerba mate.

40. The method of embodiment 39, wherein the stationary phase is a weak anion exchange stationary phase.

41. The method of embodiment 39, wherein the first aqueous elution composition comprises 25% ethanol.

42. The method of embodiment 39, wherein the stationary phase is eluted at 25° C. with the first aqueous elution composition.

43. The method of embodiment 39, wherein the stationary phase is eluted at a rate of 2 bed volumes per hour with the first aqueous elution composition.

44. The method of embodiment 39, wherein the second aqueous elution composition comprises 70% (v/v) ethanol and 0.75% (w/v) of phosphoric acid.

45. The method of embodiment 39, wherein the stationary phase is eluted at a rate of 1 bed volumes per hour with the second aqueous elution composition.

46. The method of any one of embodiments 1-38, wherein the biomass is *Stevia*.

47. The method of embodiment 46, wherein the stationary phase is a weak anion exchange stationary phase.

48. The method of embodiment 46, wherein the first aqueous elution composition comprises 25% ethanol.

49. The method of embodiment 46, wherein the stationary phase is eluted at 25° C. with the first aqueous elution composition.

50. The method of embodiment 46, wherein the stationary phase is eluted at a rate of 2 bed volumes per hour with the first aqueous elution composition.

51. The method of embodiment 46, wherein the initial extract is contacted with the stationary phase and the stationary phase is washed with the first aqueous composition to obtain a first wash composition comprising steviol glycoside.

52. The method of embodiment 46, wherein the first eluent comprises steviol glycoside.

53. The method of embodiment 46, wherein the second aqueous elution composition comprises 70% (v/v) ethanol and 0.88% (w/v) of 85 wt % phosphoric acid.

54. The method of embodiment 46, wherein second aqueous elution composition 70% (v/v) ethanol and 0.75% (w/v) of phosphoric acid 55. The method of embodiment 47, wherein the stationary phase is eluted at a rate of 1 bed volumes per hour with the second aqueous elution composition.

56. A method for isolating a caffeoylquinic composition from yerba biomass, the method comprising:
contacting yerba mate biomass with a first aqueous composition to obtain an initial extract;
chromatographing the initial extract on a weak anion exchange stationary phase;
washing the stationary phase with the first aqueous composition;
eluting the weak anion exchange stationary phase with an aqueous 25% ethanol composition to obtain a first eluent; and
eluting the stationary phase with an aqueous acidified 70% ethanol composition to obtain a second eluent comprising one or more of monocaffeoylquinic acids, dicaffeoylquinic acids, and salts of the foregoing.

57. A method for isolating a steviol glycoside composition and a caffeoylquinic composition from *Stevia* biomass, the method comprising:
contacting *Stevia* biomass with a first aqueous composition to obtain an initial *Stevia* extract;
chromatographing the initial *Stevia* extract on a weak anion exchange stationary phase;
washing the stationary phase with the first aqueous composition to obtain a wash solution comprising steviol glycoside composition;
eluting the weak anion exchange stationary phase with an aqueous 25% ethanol composition to obtain a first eluent comprising steviol glycoside composition; and
eluting the stationary phase with an aqueous acidified 70% ethanol composition to obtain a second eluent comprising one or more of monocaffeoylquinic acids, dicaffeoylquinic acids, and salts of the foregoing.

58. The method of any one of embodiments 1-57, wherein the caffeoylquinic composition when dried comprises less than 3 wt % of a total of malonate, malonic acid, oxalate, oxalic acid, lactate, lactic acid, succinate, succinic acid, malate, malic acid, citrate, and citric acid in the composition.

59. The method of any one of embodiments 1-57, wherein the caffeoylquinic composition when dried comprises less than 0.5 wt % of a total of tartrate, tartaric acid, pyruvate, pyruvic acid, fumarate, fumaric acid, ascorbic acid, sorbate, sorbic acid, acetate, and acetic acid in the composition.

60. The method of any one of embodiments 1-57, wherein the caffeoylquinic composition when dried comprises less than 1 wt % of a total of sulfate, sulfuric acid, phosphate, phosphoric acid, nitrate, nitric acid, nitrite, nitrous acid, chloride, hydrochloric acid, ammonia, and ammonium in the composition.

61. The method of any one of embodiments 1-57, wherein the caffeoylquinic composition when dried comprises less than 5 wt % of a total of flavonoids, isoflavanoids, and neoflavanoids (quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glyciteinin the composition.

62. The method of any one of embodiments 1-57, wherein the caffeoylquinic composition when dried comprises less than 5 wt % of a total of hesperidin, naringin, rutin, quercitrin, luteolin-glucoside, and quercetin-xyloside in the composition.

63. The method of any one of embodiments 1-57, wherein the caffeoylquinic composition when dried comprises less than 5 wt % of a total of cyanidin, delphinidin, malvidin, pelargonidin, peonidin, and petunidin in the composition.

64. The method of any one of embodiments 1-57, wherein the caffeoylquinic composition when dried comprises less than 1 wt % of a total tannins and tannic acid in the composition.

65. The method of any one of embodiments 1-57, wherein the caffeoylquinic composition when dried comprises less than 0.1 wt % of a total alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine in the composition.

66. The method of any one of embodiments 1-57, wherein the caffeoylquinic composition when dried comprises less than 1 wt % of a total monoglycerides, diglycerides, and triglycerides in the composition.

67. The method of any one of embodiments 1-57, wherein the caffeoylquinic composition when dried comprises less than 1 wt % of a total monosaccharides, disaccharides, polysaccharides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, and panosein in the composition.

68. The method of any one of embodiments 1-57, wherein the caffeoylquinic composition when dried comprises less than 1 wt % of a total of sugar alcohols, glycerol, sorbitol, mannitol, xylitol, maltitol, lactitol, erythritol, isomalt, and inositol in the composition.

69. The method of any one of embodiments 1-57, wherein the caffeoylquinic composition when dried comprises less than 1 wt % of a total of dietary fiber, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *psyllium* husk mucilage, resistant starches, tara gum, tragacanth gum, xanthan gum, cellulose, chitin, and chitosanin the composition.

70. The method of any one of embodiments 1-57, wherein the caffeoylquinic composition when dried comprises less than 0.1 wt % of a total of chlorophyll, furans, furan-containing chemicals, theobromine, theophylline, and trigonelline in the composition.

71. The method of any one of embodiments 1-57, wherein the caffeoylquinic composition when dried comprises less than 1 wt % of a total of caffeine in the composition.

72. The method of any one of embodiments 1-57, wherein the caffeoylquinic composition when dried comprises less than 1 wt % of a total of rutin in the composition.

73. The method of any one of embodiments 1-57, wherein the caffeoylquinic composition when dried comprises less than 0.5 wt % of a total of glycosylated ursolic acid and glycosylated oleanolic acid in the composition.

74. The method of any one of embodiments 1-57, wherein the caffeoylquinic composition when dried comprises less than 0.5 wt % of a total of volatile organic compounds, terpenes, eugenol, geraniol, geranial, alpha-ionone, beta-ionone, epoxy-ionone, limonene, linalool, linalool oxide, nerol, and damascenone in the composition.

75. The method of any one of embodiments 1-57, wherein the caffeoylquinic composition when dried comprises less than 0.5 wt % of a total of fatty acid oxidation products, decanone, decenal, nonenal, octenal, heptenal, hexenal, pentenal, pentenol, pentenone, hexenone, hydroxynonenal, and malondialdehyde in the composition.

76. The method of any one of embodiments 1-57, wherein the caffeoylquinic composition when dried comprises less than 0.01 wt % of a total of polycyclic aromatic hydrocarbons (PAHs), such as: acenaphthene, acenaphthylene, anthracene, benzo(a)anthracene, benzo(a)pyrene, benzo(b) fluoranthene, benzo(ghi)perylene, benzo(k)fluoranthene, chrysene, dibenzo(a,h)anthracene, fluoranthene, fluorene, indeno(1,2,3-cd)pyrene, naphthalene, phenanthrene, and pyrene in the composition.

77. The method of embodiment 1, wherein polycyclic aromatic hydrocarbons (PAHs) (acenaphthene, acenaphthylene, anthracene, benzo(a)anthracene, benzo(a)pyrene, benzo(b) fluoranthene, benzo(ghi)perylene, benzo(k)fluoranthene, chrysene, dibenzo(a,h)anthracene, fluoranthene, fluorene, indeno(1,2,3-cd)pyrene, naphthalene, phenanthrene, pyrene, and others) are removed to below 0.01% by weight.

78. The method of any one of embodiments 1-57, wherein the caffeoylquinic composition when dried comprises less than 0.5 wt % of a total of fatty acid oxidation products, decanone, decenal, nonenal, octenal, heptenal, hexenal, pentenal, pentenol, pentenone, hexenone, hydroxynonenal, and malondialdehyde in the composition.

79. The method of any one of embodiments 1-57, wherein color is removed such that a % transmittance at 430 nm is >80%.

80. The method of any one of embodiments 1-57, wherein color is removed such that a b value is less than 4 on CIE L*a*b* color space.

81. The method of any one of embodiments 1-33 and 37-57, wherein color is removed such that a % transmittance at 430 nm is >80% without a decoloring and/or desalting step.

82. The method of any one of embodiments 1-33 and 37-57, wherein color is removed such that a b value is less than 4 on CIE L*a*b* color space without a decoloring and/or desalting step 83. A composition comprising at least one of monocaffeoylquinic acid and dicaffeoylquinic acid, and salts thereof made by the method of any one of embodiments 1-82.

84. An ingestible composition comprising the composition of embodiment 83.

85. The ingestible composition of embodiment 84, wherein the ingestible composition is a beverage or a food product.

The invention claimed is:

1. A method for making a caffeoylquinic composition, the method comprising:
i) contacting biomass with a first aqueous composition to obtain an initial extract;
ii) chromatographing the initial extract on an ion exchange stationary phase;
iii) eluting the stationary phase with a first aqueous elution composition comprising 10%-50% (C1-C4)alkanol to obtain a first eluent; and
iv) eluting the stationary phase with an acidified second aqueous elution composition comprising 60% to 80% (C1-C4)alkanol to obtain the caffeoylquinic composition,
wherein the caffeoylquinic composition comprises one or more of monocaffeoylquinic acid, dicaffeoylquinic acid, and salts of the foregoing; and wherein the caffeoylquinic composition comprises less than 1% by weight or caffeine or rutin based on dry weight of the caffeoylquinic composition, and
wherein the caffeoylquinic composition has a percent transmittance at 430 nm of greater than 80% without a decoloring or desalting step following step (iv).

2. The method of claim 1, wherein the biomass is selected from the group consisting of yerba mate, *Stevia*, and globe artichoke.

3. The method of claim 1, further comprising removing solids from the initial extract before chromatographing in step (ii).

4. The method of claim 1, wherein monocaffeoylquinic acid comprises one or more of 3-O-caffeoylquinic acid, 4-O-caffeoylquinic acid, and 5-O-caffeoylquinic acid.

5. The method of claim 1, wherein dicaffeoylquinic acid comprises one or more of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof.

6. The method of claim 1, wherein the stationary phase is weak anion exchange stationary phase.

7. The method of claim 1, wherein the first aqueous composition is heated to 50-70° C. before contacting with the biomass.

8. The method of claim 1, wherein the initial extract is contacted with the stationary phase at 20-25° C.

9. The method of claim 1, wherein, in step (ii), the initial extract is contacted with the ion exchange stationary phase and the contacted ion exchange stationary phase is washed with the first aqueous composition to obtain a first wash composition.

10. The method of claim 1, wherein the first aqueous elution composition comprises 20-30% (C1-C4)alkanol by volume.

11. The method of claim 10, wherein the (C1-C4)alkanol is ethanol.

12. The method of claim 1, wherein the second aqueous elution composition comprises about 70% (C1-C4)alkanol by volume.

13. The method of claim 1, wherein the second aqueous elution composition comprises 1-10% of a salt.

14. The method of claim 1, wherein the second aqueous elution composition is acidified with 0.5-1.0% phosphoric acid.

15. The method of claim 1, wherein the second aqueous elution composition is heated to 40-50° C. before eluting the stationary phase.

16. The method of claim 1, wherein the caffeoylquinic composition has a ratio by mass of monocaffeoylquinic acid and salts thereof to dicaffeoylquinic acid and salts thereof, of about 0.01:1 to about 1:1, about 0.1:1 to about 0.5:1, about 1:1 to about 10:1, about 3:1 to about 10:1, about 3:1 to about 5:1, or about 3:2 to about 4:1.

17. The method of claim 1, further comprising a decoloring step.

18. The method of claim 1, further comprising a desalting step.

19. The method of claim 1, further comprising chromatographing the caffeoylquinic composition with a hydrophobic resin stationary phase to desalt the caffeoylquinic composition.

20. The method of claim 1, further comprising drying the first eluent, drying the caffeoylquinic composition, or drying the first eluent and the caffeoylquinic composition.

21. The method of claim 1, wherein the biomass is yerba mate and the second aqueous elution composition comprises 70% (v/v) ethanol and 0.75% (w/v) of phosphoric acid.

22. A method for isolating a steviol glycoside composition and a caffeoylquinic composition from *Stevia* biomass, the method comprising:
  i) contacting *Stevia* biomass with a first aqueous composition to obtain an initial *Stevia* extract;
  ii) chromatographing the initial *Stevia* extract on a weak anion exchange stationary phase;
  iii) washing the stationary phase with the first aqueous composition to obtain a wash solution comprising steviol glycoside composition;
  iv) eluting the weak anion exchange stationary phase with an aqueous ethanol composition comprising 10% to 50% ethanol to obtain a first eluent comprising steviol glycoside composition; and
  v) eluting the stationary phase with an aqueous acidified ethanol composition comprising 60% to 80% ethanol to obtain the caffeoylquinic composition comprising one or more of monocaffeoylquinic acids, dicaffeoylquinic acids, and salts of the foregoing and comprising less than 1% by weight of caffeine or rutin based on dry weight of the caffeoylquinic composition,
  wherein the caffeoylquinic composition has a percent transmittance at 430 nm of greater than 80% without a decoloring or desalting step following step (v).

23. The method of claim 1, wherein the caffeoylquinic composition comprises
  less than 3 wt % of a total of malonate, malonic acid, oxalate, oxalic acid, lactate, lactic acid, succinate, succinic acid, malate, malic acid, citrate, and citric acid in the composition;
  less than 0.5 wt % of a total of tartrate, tartaric acid, pyruvate, pyruvic acid, fumarate, fumaric acid, ascorbic acid, sorbate, sorbic acid, acetate, and acetic acid in the composition;
  less than 1 wt % of a total of sulfate, sulfuric acid, phosphate, phosphoric acid, nitrate, nitric acid, nitrite, nitrous acid, chloride, hydrochloric acid, ammonia, and ammonium in the composition;
  less than 5 wt % of a total of flavonoids, isoflavanoids, and neoflavanoids(quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glyciteinin the composition;
  less than 5 wt % of a total of hesperidin, naringin, rutin, quercitrin, luteolin-glucoside, and quercetin-xyloside in the composition;
  less than 5 wt % of a total of cyanidin, delphinidin, malvidin, pelargonidin, peonidin, and petunidin in the composition; and/or
  less than 1 wt % of a total tannins and tannic acid in the composition, based on dry weight of the caffeoylquinic composition.

24. The method of claim 1, wherein the caffeoylquinic composition comprises
  less than 0.1 wt % of a total alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine in the composition;
  less than 1 wt % of a total monoglycerides, diglycerides, and triglycerides in the composition;
  less than 1 wt % of a total monosaccharides, disaccharides, polysaccharides, glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, and panosein the composition;
  less than 1 wt % of a total of sugar alcohols, glycerol, sorbitol, mannitol, xylitol, maltitol, lactitol, erythritol, isomalt, and inositol in the composition;
  less than 1 wt % of a total of dietary fiber, acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, hemicellulose, inulin, karaya gum, pectin, polydextrose, *Psyllium* husk mucilage, resistant starches, tara gum, tragacanth gum, xanthan gum, cellulose, chitin, and chitosanin the composition; and/or
  less than 0.1 wt % of a total of chlorophyll, furans, furan-containing chemicals, theobromine, theophylline, and trigonelline in the composition, based on dry weight of the caffeoylquinic composition.

25. The method of claim 1, wherein the caffeoylquinic composition comprises less than 1 wt % of caffeine in the composition, based on dry weight of the caffeoylquinic composition.

26. The method of claim 1, wherein the caffeoylquinic composition comprises less than 1 wt % of rutin in the composition, based on dry weight of the caffeoylquinic composition.

27. The method of claim 1, wherein the caffeoylquinic composition comprises
  less than 0.5 wt % of a total of glycosylated ursolic acid and glycosylated oleanolic acid in the composition;
  less than 0.5 wt % of a total of volatile organic compounds, terpenes, eugenol, geraniol, geranial, alpha-ionone, beta-ionone, epoxy-ionone, limonene, linalool, linalool oxide, nerol, and damascenone in the composition;
  less than 0.5 wt % of a total of fatty acid oxidation products, decanone, decenal, nonenal, octenal, heptenal, hexenal, pentenal, pentenol, pentenone, hexenone, hydroxynonenal, and malondialdehyde in the composition; and/or
  less than 0.01 wt % of a total of polycyclic aromatic hydrocarbons (PAHs), acenaphthene, acenaphthylene, anthracene, benzo(a)anthracene, benzo(a)pyrene, benzo(b)fluoranthene, benzo(ghi)perylene, benzo(k)fluoranthene, chrysene, dibenzo(a,h)anthracene, fluoranthene, fluorene, indeno(1,2,3-cd)pyrene, naphthalene, phenanthrene, and pyrene in the composition, based on dry weight of the caffeoylquinic composition.

28. The method of claim 1, wherein the caffeoylquinic composition has a percent transmittance at 430 nm that is greater than 80%.

29. The method of claim 1, wherein the caffeoylquinic composition has a b value less than 4 on CIE L*a*b* color space.

30. The method of claim 1, wherein the caffeoylquinic composition has a b value less than 4 on CIE L*a*b* color space without a decoloring or desalting step following step (iv).

31. The method of claim 1, wherein the biomass is *Stevia*, the first eluent comprises steviol glycoside, and the second aqueous elution composition comprises 70% (v/v) ethanol and 0.75% (w/v) of phosphoric acid.

32. A method for isolating a caffeoylquinic composition from yerba biomass, the method comprising:

i) contacting yerba mate biomass with a first aqueous composition to obtain an initial extract;
ii) chromatographing the initial extract on a weak anion exchange stationary phase;
iii) washing the stationary phase with the first aqueous composition;
iv) eluting the weak anion exchange stationary phase with an aqueous ethanol composition comprising 10% to 50% ethanol to obtain a first eluent; and
v) eluting the stationary phase with an aqueous acidified ethanol composition comprising 60% to 80% ethanol to obtain the caffeoylquinic composition comprising one or more of monocaffeoylquinic acids, dicaffeoylquinic acids, and salts of the foregoing and comprising less than 1% by weight of caffeine or rutin based on dry weight of the caffeoylquinic composition,
wherein the caffeoylquinic composition has a percent transmittance at 430 nm of greater than 80% without a decoloring or desalting step following step (v).

33. The method of claim 1, wherein the first aqueous composition is free of organic solvent.

* * * * *